US012680062B2

(12) United States Patent
Allbritton et al.

(10) Patent No.: US 12,680,062 B2
(45) **Date of Patent: *Jul. 14, 2026**

(54) FORMATION OF ARRAYS OF PLANAR INTESTINAL CRYPTS POSSESSING A STEM/PROLIFERATIVE CELL COMPARTMENT AND DIFFERENTIATED CELL ZONE

(71) Applicant: The University of North Carolina at Chapel Hill, Chapel Hill, NC (US)

(72) Inventors: Nancy L. Allbritton, Seattle, WA (US); Yuli Wang, Lynnwood, WA (US); Raehyun Kim, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 1040 days.

This patent is subject to a terminal disclaimer.

(21) Appl. No.: 17/044,157

(22) PCT Filed: May 24, 2019

(86) PCT No.: PCT/US2019/033955

§ 371 (c)(1),
(2) Date: Sep. 30, 2020

(87) PCT Pub. No.: WO2019/227012

PCT Pub. Date: Nov. 28, 2019

(65) Prior Publication Data

US 2023/0098968 A1 Mar. 30, 2023

Related U.S. Application Data

(60) Provisional application No. 62/676,418, filed on May 25, 2018.

(51) Int. Cl.

| | |
|---|---|
| ***C12M 3/00*** | (2006.01) |
| ***C12M 1/12*** | (2006.01) |
| ***C12M 1/42*** | (2006.01) |
| ***C12Q 1/08*** | (2006.01) |

(52) U.S. Cl.
CPC ............ *C12M 21/08* (2013.01); *C12M 25/04* (2013.01); *C12M 35/08* (2013.01); *C12Q 1/08* (2013.01)

(58) Field of Classification Search
CPC ...... C12M 21/08; C12M 25/04; C12M 35/08; C12M 35/04; C12Q 1/08; A61L 27/3813
See application file for complete search history.

(56) References Cited

U.S. PATENT DOCUMENTS

| | | | |
|---|---|---|---|
| 8,946,305 | B2 | 2/2015 | Liao et al. |
| 9,040,665 | B2 | 5/2015 | Wnek et al. |
| 9,132,208 | B2 | 9/2015 | Chen et al. |
| 9,200,676 | B2 | 12/2015 | Yamaguchi |
| 9,205,172 | B2 | 12/2015 | Leonard Neethling et al. |
| 9,211,362 | B2 | 12/2015 | Hwang et al. |
| 9,272,004 | B2 | 3/2016 | Nataraj et al. |
| 9,283,301 | B1 | 3/2016 | Simionescu et al. |
| 11,193,110 | B2 | 12/2021 | Allbritton et al. |
| 2003/0017142 | A1 | 1/2003 | Toner et al. |
| 2005/0106717 | A1 | 5/2005 | Wilson et al. |
| 2006/0019389 | A1 | 1/2006 | Yayon et al. |
| 2006/0121609 | A1 | 6/2006 | Yannas et al. |
| 2007/0134790 | A1 | 6/2007 | Gould et al. |
| 2009/0253153 | A1 | 10/2009 | Chu et al. |
| 2010/0047853 | A1 | 2/2010 | Kuo |
| 2010/0075293 | A1 | 3/2010 | Chang |
| 2012/0015003 | A1 | 1/2012 | Gleeson et al. |
| 2012/0089238 | A1 | 4/2012 | Kang et al. |
| 2014/0093478 | A1 | 4/2014 | Turnbaugh et al. |
| 2017/0059555 | A1 | 3/2017 | Iyer et al. |

(Continued)

FOREIGN PATENT DOCUMENTS

| | | |
|---|---|---|
| JP | 2008513159 A | 5/2008 |
| JP | 2009250977 A | 10/2009 |

(Continued)

OTHER PUBLICATIONS

Wang et al. "Formation of Human Colonic Crypt Array by Application of Chemical Gradients Across a Shaped Epithelial Monolayer." Cell Mol Gastroenterol Hepatol . Nov. 3, 2017;5(2):113-130. (Year: 2017).*

Advisory Action and Interview Summary corresponding to U.S. Appl. No. 15/545,456 dated Apr. 10, 2019.

Advisory Action corresponding to U.S. Appl. No. 16/316,139 dated Apr. 4, 2022.

A. DeWard, J. Cramer, and E. Lagasse, Cellular heterogeneity in the mouse esophagus implicates the 30 presence of a nonquiescent epithelial stem cell population, Cell. Rep. 9(2), 701-711 (Oct. 23, 2014).

(Continued)

*Primary Examiner* — Titilayo Moloye
(74) *Attorney, Agent, or Firm* — KDW FIRM PLLC

(57) ABSTRACT

A method for producing tissue constructs comprising two or more distinct regions, each of which comprises a different cell population or lineage is described. The method involves providing a support substrate or substrate assembly comprising two or more physically distinct regions, wherein the two or more physically distinct regions of the support substrate or substrate assembly are different from each other; and depositing/positioning one or more cells on the support substrate or substrate assembly. The cells can form a continuous monolayer with at least two zones, e.g., a proliferative zone and a nonproliferative zone, that can act as in vitro intestinal models. The models are two-dimensional, thus facilitating rapid and facile imaging Systems comprising the tissue constructs and methods of using the constructs to study the effects of pharmaceuticals, uutraceuticais, and metabolites on intestinal cells are also described.

7 Claims, 19 Drawing Sheets

(56) References Cited

U.S. PATENT DOCUMENTS

| | | | | |
|---|---|---|---|---|
| 2017/0191026 | A1* | 7/2017 | Alexander | C12M 47/02 |
| 2017/0306278 | A1 | 10/2017 | Nguyen et al. | |
| 2018/0002672 | A1 | 1/2018 | Allbritton et al. | |
| 2019/0211296 | A1 | 7/2019 | Allbritton et al. | |
| 2019/0382703 | A1 | 12/2019 | Katayama | |
| 2021/0087515 | A1 | 3/2021 | Allbritton et al. | |
| 2021/0395661 | A1 | 12/2021 | Allbritton et al. | |

FOREIGN PATENT DOCUMENTS

| | | | | |
|---|---|---|---|---|
| JP | 2011523355 | A | 8/2011 | |
| JP | 2012500371 | | 1/2012 | |
| JP | 2013510179 | A | 3/2013 | |
| JP | 2014514942 | A | 6/2014 | |
| JP | 2019518443 | A | 7/2019 | |
| JP | 6920203 | B2 | 7/2021 | |
| JP | 7042252 | | 3/2022 | |
| WO | WO/2005/072419 | | 8/2005 | |
| WO | 2005104755 | A2 | 11/2005 | |
| WO | WO/2009/132196 | | 10/2009 | |
| WO | WO/2012/136701 | A1 | 10/2012 | |
| WO | WO 2014/021778 | A1 | 2/2014 | |
| WO | WO/2014/186430 | A1 | 11/2014 | |
| WO | WO 2015/020614 | A1 | 2/2015 | |
| WO | WO-2016123474 | A1 * | 8/2016 | C12N 5/0679 |
| WO | WO 2017/131839 | A2 | 8/2017 | |
| WO | WO/2018/022548 | A1 | 2/2018 | |
| WO | 2018052953 | A1 | 3/2018 | |
| WO | 2018175861 | A1 | 9/2018 | |
| WO | 2018185321 | A1 | 10/2018 | |
| WO | 2018225835 | A1 | 12/2018 | |
| WO | WO/2019/141824 | A1 | 7/2019 | |
| WO | WO/2019/222333 | A1 | 11/2019 | |
| WO | WO/2020102682 | A1 | 5/2020 | |

OTHER PUBLICATIONS

A. Gracz et al., CD24 and CD44 Mark Human Intestinal Epithelial Cell Populations with Characteristics of Active and Facultative Stem Cells, Stem Cells 31(9), 2024-30 (2013).

A. L. Paguirigan and D. J. Beebe, "Protocol for the fabrication of enzymatically crosslinked gelatin microchannels for microfluidic cell culture" Nat Protoc, 2007, 2, 1782-1788.

Alipour et al. Measurement of Vocal Folds Elastic Properties for Continuum Modeling. Journal of Voice (2012), 26(6), 816.e21-816.e29. (Year: 2012).

A. Quaroni. Short-term primary culture of epithelial cells from human colon. Gastroenterology, 1989, 96, 535-536.

Bartsch et al. "Establishment of a Long-Term Culture System for Rat Colon Epithelial Cells," In Vitro Cell. Dev. Biol.—Animal, 2004, vol. 40, pp. 278-284 (Year: 2004).

Belchior. Gustavo Gross et al. Stem cells and biopharmaceuticals: Vital roles in the growth of tissue-engineered small intestine, Seminars in. Pediatric Surgery, 23(3):141-149 (2014).

Bishop et al. Regulation of Caco-2 cell proliferation by basolateral membrane epidermal growth factor receptors. Am J. Physiol (1994), v267(5 Pt. 1), G892-900. (Year: 1994).

Boccellato et al., "Polarised epithelial monolayers of the gastric mucosa reveal insights into mucosal homeostasis and defence against infection," Gut, vol. 68, pp. 400-413 (2019).

Bo Liu et al. Chemistry of Periodate-Mediated Cross-Linking of 3.4-Dihydroxylphenylalanine (DOPA)-Containing Molecules to Proteins, J Am Chem Soc. 2006; 29:15228-15235, p. 8.

C. Booth, S. Patel, G. R. Bennion and C. S. Patten. The isolation and culture of adult mouse colonic epithelium. Epithelial Cell Biol., 1995, 4, 76-86.

C. Kosinski, et al., Gene expression patterns of human colon tops and basal crypts and BMP antagonists as intestinal stem cell niche factors, Proc. Natl. Acad. Sci. U S. A., 2007, 104, 15418-15423.

C. Moon, K. L. VanDussen, H. Miyoshi and T. S. Stappenbeck. Development of a primary mouse intestinal epithelial cell monolayer culture system to evaluate factors that modulate IgA transcytosis. Mucosal Immunol, 2014, 7, 818-828.

C. R. Yang, "Enhance physiocochemical properties of collagen by using EDC/NHS-crosslinking", Bull. Mat. Sci, 2012, 35, 913-918.

Canadian Office Action Corresponding to Canadian Application No. 3,009,153 dated Feb. 2, 2022.

Cell Culture Inserts, 0.4um, Falcon®. MG Scientific, internet article (2014). (Year: 2014).

Corrected Notice of Allowance corresponding to U.S. Appl. No. 15/545,456 dated Aug. 2, 2021.

Costello et al., "Synthetic Small Intestinal Scaffolds for Improved Studies of Intestinal Differentiation," Biotechnology and Bioengineering, vol. 111, No. 6, Jun. 2014. pp. 1222-1232.

Cummings et al. "Properties of engineered vascular constructs made from collagen, fibrin, and collagen-fibrin mixtures," Biomaterials 25, 3699-3706 (2003).

D.R. Donohoe, N. Garge, X. X. Zhang, W. Sun, T. M. O'Connell, M. K. Bunger and S. J. Bultman, Cell Metabolism, 2011, 13, 517-526.

Donohoe et al., "The Warburg Effect Dictates the Mechanism of Butyrate-Mediated Histone Acetylation and Cell Proliferation," Molecular Cell, vol. 48 pp. 612-626 (2012).

Deveney et al. Establishment of Human Colonic Epithelial Cells in Long-Term Culture. Journal of Surgical Research (1996), 64, 161.

Fuchs et al. "A matter of life and death: self-renewal in stem cells," Embo Reports, vol. 14, No. 1, pp. 39-48 (2013).

E. J. Formeister, A. L. Sionas, D. K. Lorance, C. L. Barkley, G. H. Lee and S. T. Magness, Distinct SOX9 levels differentially mark stem/progenitor populations and enteroendocrine cells of the small intestine epithelium, Am. J Physiol.-Gastroint. Liver Physiol., 2009, 296, G 1108-G1118.

Song et al. "Collagen scaffolds derived from a marine source and their biocompatibility," Biomaterials, 27, 2951-2961 (2006).

Elamin et al., "Effects of Ethanol and Acetaldehyde on Tight Junction Integrity: In Vitro Study in a Three Dimensional Intestinal Epithelial Cell Culture Model." PLoS One, vol. 7, Article ID e35008 (2012).

Extended European Search Report corresponding to European Application No. 16744178.1, dated Jul. 2, 2018, 7 pages.

Extended European Search Report corresponding to European Patent Application No. 17835084.9 dated Mar. 5, 2020.

Extended European Search Report corresponding to European Application No. 19806626.8-1132 dated Feb. 4, 2022.

Extended European Search Report corresponding to European Application No. 19804471.1-1132 dated Feb. 28, 2022.

F. Wang et al., Isolation and Characterization of Intestinal Stem Cells Based on Surface Marker Combinations and Colony-Formation Assay Gastroenterology 145(2), 383-95 (2013a).

Ferruzza et al. A protocol for differentiation of human intestinal Caco-2 cells in asymmetricserum-containing medium. Toxicology in Vitro (2012), v26, p. 1252-1255. (Year: 2012).

Frantz et al. The extracellular matrix at a glance. Journal of Cell Science (2010), 123, 4195-4200. (Year: 2010).

Gaudier et al., "Butyrate specifically modulates MUC gene expression in intestinal epithelial goblet cells deprived of glucose," Am J. Physiol Gastrointest Liver Physiol., vol. 287: G1168-G1174 (2004).

G. L. Eastwood and J. S. Trier. Organ culture of human rectal mucosa. Gastroenterology, 1973, 64(3), 375-382.

Gracz et al., "Identification, Isolation, and Culture of Intestinal Epithelial Stem Cells from Murine Intestine," Methods Mol Biol.,; vol. 879, pp. 89-107, 23 page author manuscript. (Year: 2012).

Gonzalez S et al. A 3D Culture System Enhances the Ability of Human Bone Marrow Stromal Cells to Support the Growth of Limbal Stem/Progenitor Cells, Stem Cell Res. 2016, 16(2):358-364, p. 2,3.

H. Autrup, L. A. Barrett, F. E. Jackson, M. L. Jesudason, G. Stoner, P. Phelps, B. F. Trump and C. C. Harris. Explant culture of human colon. Gastroenterology, 1978, 74, 1248-1257.

Sundararaghavan et al. "Genipin-induced changes in collagen gels: Correlation of mechanical properties to fluorescence," Journal of Biomedical Materials Research Part A, 87A, 308-320 (2008).

(56) References Cited

OTHER PUBLICATIONS

Yoo et al. "Effects of Schisandra Lignans on P-Glycoprotein-Mediated Drug Efflux in Human Intestinal Caco-2 Cells," Planta Med., 73, 444-450 (2007).
H. J. Kim, D. Huh, G. Hamilton and D. E. Ingber. Human gut-on-a-chip inhabited by microbial flora that experiences intestinal peristalsis-like motions and flow. Lab Chip, 2012, 12, 2165-2174.
Hai-Long Li et al. The Effect of Amino Density on the Attachment, Migration, and Differentiation of Rat Neural Stem Cells In Vitro, Mol Cells. 2013; 35:436-443. pp. 436, 437, 441.
Hass et al. Lack of Butyrate Is Associated With Induction of Bax and Subsequent Apoptosis in the Proximal Colon of Guinea Pig. Gastroenterology (1997), 112:875-881. (Year: 1997).
International Preliminary Report on Patentability corresponding to International Application No. PCT/US2016/015631 dated Aug. 1, 2017.
International Preliminary Report on Patentability corresponding to International Application No. PCT/US2017/043601 dated Jan. 29, 2019.
International Preliminary Report on Patentability corresponding to International Application No. PCT/US2019/032393 dated Nov. 17, 2020.
International Preliminary Report on Patentability corresponding to International Application No. PCT/US2019/033955 dated Dec. 1, 2020.
International Preliminary Report on Patentability corresponding to International Application No. PCT/US2019/061743 dated May 18, 2021.
International Search Report corresponding to International Application No. PCT/US2016/015631 dated May 26, 2016.
International Search Report corresponding to International Application No. PCT/US2017/043601 dated Nov. 16, 2017.
International Search Report corresponding to International Application No. PCT/US2019/032393 dated Jul. 23, 2019.
International Search Report corresponding to International Application No. PCT/US2019/033955 dated Aug. 15, 2019.
International Search Report corresponding to International Application No. PCT/US2019/061743 dated Feb. 11, 2020.
Interview Summary corresponding to U.S. Appl. No. 15/545,456 dated Mar. 15, 2019.
J. B. Seidelin, T. Horn and 0. H. Nielsen. Simple and efficient method for isolation and cultivation of endoscopically obtained human colonocytes. Am. J. Physiol.-Gastroint. Liver Physiol., 2003, 285, G1122-G1128.
J. H. Sung, J. J. Yu, D. Luo, M. L. Shuler and J. C. March. Microscale 3-D hydrogel scaffold for biomimetic gastrointestinal (GI) tract model. Lab Chip, 2011, 11, 389-392.
J. H. Sung, M. B. Esch, J. M. Prat, C. J. Long, A. Smith, J. J. Hickman and M. L. Shuler, Microfabricated mammalian organ systems and their integration into models of whole animals and humans. Lab Chip, 2013, 13(7), 1201-1212.
Orban et al. "Crosslinking of collagen gels by transglutaminase," Journal of Biomedical Materials Research Part A, 68A, 756-762 (2004).
J. Mills and R. Shivdasani, Gastric epithelial stem cells, Gastroenterology 140(2), 412-424 (Feb. 2011).
J. R. Davie, "Inhibition of Histone Deacetylase Activity by Butyrate", Journal of Nutrition, 2003, 133, 2485S-2493S.
Jones, S. P. et al., "Inhibition of Histone Deacetylase Activity by Butyrate", Ecotoxicology 23, 802-808 (2014).
VanDussen et al. "Development of an enhanced human gastrointestinal epithelial culture system to facilitate patient-based assays," Gut, vol. 64, pp. 911-920 (2015).
Kaminsky et al. "Small Intestinal Cytochromes P450," Critical Reviews in Toxicology 21, 407-422 (1992).
Kharkar et al. (2013), "Designing degradable hydrogels for orthogonal control of cell microenvironments," Chem. Soc. Rev., vol. 42, pp. 7335-7372. (Year: 2013).
Damink et al. "Glutaraldehyde as a crosslinking agent for collagen-based biomaterials," Journal of Materials Science: Materials in Medicine, 6, 460-472 (1995).
Lancaster, M. A. et al. "Organogenesis in a dish: Modeling development and disease using organoid technologies", Science, 345(6194):283 (2014).
Levenberg S, et al. Differentiation of human embryonic stem cells on three-dimensional polymer scaffolds, PNAS. 2003, 100(22): 12741-12746, p. 12741.
M. A. Cayo, A. K. Cayo, S. M. Jarjour and H. Chen, "Sodium butyrate activates Notch1 signaling, reduces tumor markers, and induces cell cycle arrest and apoptosis in pheochromocytoma", American Journal of Translational Research, 2009, 1, 178-183.
M. Brittan and N. A. Wright, "Stem Cell in Gastrointestinal Structure and Neoplastic Development", Gut, 2004, 53, 899-910.
M. Hovakimyan, R. F. Guthoff and O. Stachs, "Collagen Cross-Linking: Current Status and Future Directions", Journal of Ophthalmology, 2012, 2012, Article ID 406850.
M. Stelzner, M. Helmrath, J. C. Y. Dunn, S. J. Henning, C. W. Houchen, C. Kuo, J. Lynch, L. H. Li, S. T. Magness, M. G. Martin, M. H. Wong, J. Yu and N. I. H. I. S. C. Consortiu,Am. J Physiol.-Gastroint. Liver Physiol., 2012, 302, G1359-G1363.
Maenosono et al. "A Transparent Polyimide Film as a Biological Cell Culture Sheet with Microstructures,". Journal of Biomaterials and Nanobiotechnology, vol. 5, pp. 17-23.(Year: 2014).
Maina JN. Structure, function and evolution of the gas exchangers: comparative perspectives, J Anat. 2002, 201:281-304, p. 300.
Martignoni et al., Abstract of "An in vivo and in vitro comparison of CYP induction in rat liver and intestine using slices and quantitative RT-PCR," Chemico-Biological Interactions, vol. 151, Iss. 1, pp. 1-11 (2004), 19 pages.
Martignoni "Species and strain differences in drug metabolism in liver and intestine," University of Groningen/UMCG, 1-136 (2006).
Matsuzawa A et al. Construction of three-dimensional liver tissue models by cell accumulation technique and maintaining their metabolic functions for long-term culture without medium change, J Biomed Mater Res Part A. 2014, p. 1, Apr. 2015:103(4):1554-64.
Muñoz-Pinto et al. Lamina Propria Cellularity and Collagen Composition: An Integrated Assessment of Structure in Humans. Annals of Otology, Rhinology, and Laryngology (2009), 118(4), 299-306. (Year: 2009).
Barker, M. van de Wetering and H. Clevers, "The intestinal stem cell", Genes & Development, 2008, 22, 1856-1864.
Vrana et al. "EDC/NHS cross-linked collagen foams as scaffolds for artificial corneal stroma," Journal of Biomaterials Science-Polymer Edition, vol. 18, No. 12, pp. 1527-1545 (2007).
N. Seyedhassantehrani, Y. Li and L. Yao, Dynamic behaviours of astrocytes in chemically modified fibrin and collagen hydrogels Integrative Biology, 2016.
Notice of Allowance corresponding to U.S. Appl. No. 15/545,456 dated Jul. 21, 2021.
Notice of Publication corresponding to European Patent Application No. 17835084.9-1120 dated May 8, 2019.
Notice of Publication corresponding to European Patent Application No. 19804471.1 dated Feb. 24, 2021.
Notice of Publication corresponding to European Patent Application No. 19806626.8-1111 dated Mar. 17, 2021.
Notice of Publication corresponding to European Patent Application No. 19884975.4-1132 dated Aug. 25, 2021.
Notice of Allowance corresponding to Japanese Patent Application No. 2019-504019 dated Mar. 8, 2022.
Office Action (Restriction Requirement) corresponding to U.S. Appl. No. 15/545,456 dated Jul. 5, 2018.
Office Action corresponding to U.S. Appl. No. 15/545,456 dated Aug. 28, 2018.
Office Action corresponding to European Patent Application No. 16744178.1 dated Nov. 11, 2020.
Office Action corresponding to Japanese Patent Application No. 2017540628 dated Nov. 4, 2020.
Office Action corresponding to Japanese Patent Application No. 2017540628 dated Jan. 7, 2020.
Office Action corresponding to Japanese Patent Application No. 2019504019 dated Feb. 28, 2022.

(56) References Cited

OTHER PUBLICATIONS

Office Action corresponding to U.S. Appl. No. 15/545,456 dated Jan. 29, 2019.
Office Action corresponding to U.S. Appl. No. 15/545,456 dated Dec. 16, 2019.
Office Action corresponding to U.S. Appl. No. 15/545,456 dated Mar. 13, 2020.
Office Action corresponding to U.S. Appl. No. 15/545,456 dated Oct. 19, 2020.
Office Action (Restriction Requirement) corresponding to U.S. Appl. No. 16/316,139 dated Feb. 4, 2021.
Office Action corresponding to U.S. Appl. No. 16/316,139 dated Apr. 28, 2021.
Office Action corresponding to U.S. Appl. No. 16/316,139 dated Jan. 26, 2022.
P. Jung, T. Sato, A. Merlos-Suarez, F. M. Barriga, M. Iglesias, D. Rossell, H. Auer, M. Gallardo, M. A. Blasco, E. Sancho, H. Clevers and E. Batlle. Isolation and in vitro expansion of human colic stem cells. Nature Medicine, 2011, 17, 1225-1227.
Shah et al. "Role of Caco-2 cell monolayers in prediction of intestinal drug absorption," Biotechnol. Prog. 22: 186-198 (2006).
Szpak, "Fish bone chemistry and ultrastructure: implications for taphonomy and stable isotope analysis," J. Archaeol. Sci, 38, 3358-3372 (2011).
Paine et al. "Cytochrome P-450 1A1 Expression in Human Small Bowel: Interindividual Variation and Inhibition by Ketoconazole," Drug Metabolism and Disposition, vol. 27, No. 3, pp. 360-364 (1999).
Park YB et al. Alterations of proliferative and differentiation potentials of human embryonic stem cells during long-term culture, Exp Mol Med. 2008, 40(1):98-108, p. 1.
Pedron S et al. Microfluidic approaches for the fabrication of gradient crosslinked networks based on poly(ethylene glycol) and hyperbranched polymers for manipulation of cell interactions, J Biomed Mat Res. 2011; 96(1):196-203, p. 197.
Petersen et al. Generation of L Cells in Mouse and Human Small Intestine Organoids. Diabetes, 63(2), pp. 410-420.
Q. Ramadan, H. Jafarpoorchekab, C. B. Huang, P. Silacci, S. Carrara, G. Koklu, J. Ghaye, J. Ramsden, C. Ruffert, G. Vergeres and M. A. M. Gijs. NutriChip: nutrition analysis meets microfliudics. Lab Chip, 2013, 13, 196-203.
R. H. Whitehead, A. Brown and p. S. Bhathal. A method for the isolation and culture of human colonic crypts in collagen gels. In Vitro Cellular & Developmental Biology, 1987, vol. 23, No. 6, pp. 436-442.
Ramanujan et al. Diffusion and Convection in Collagen Gels: Implications for Transport in the Tumor Interstitium. Biophysical Journal (2002), 83, 1650-1660. (Year: 2002).
Roeder et al. "Compliance, elastic modulus, and burst pressure of small-intestine submucosa (SIS), small-diameter vascular grafts," J Biomed Mater Res. 47, 65-70 (1999).
Rodriguez-Serrano et al., "Differentiation of Intestinal Epithelial Cells Mediated by Cell Confluence and/or Exogenous Nucleoside Supplementation." Cell Tissues Organs, vol. 191, pp. 478-488 (2010).
Rosa ACP et al. Interaction of *Escherichia coli* strains of non-EPEC serogroups that carry eae and lack the EAF and stx gene sequences with undifferentiated and differentiated intestinal human Caco-2 cells, FEMS Microbiology Letters. 2001, 200: 117-122, p. 118.
S. Umar, Intestinal Stem Cells, Curr. Gastroenterol Rep. 12(5), 340-348 (Oct. 2010).
S. Yui, T. Nakamura, T. Sato, Y. Nemoto, T. Mizutani, X. Zheng, S. Ichinose, T. Nagaishi, R. Okamoto, K. Tsuchiya, H. Clevers and M. Watanabe. Functional engraftment of colon epithelium expanded in vitro from a single adult Lgr5+ stem cell. Nature Medicine, 2012, 18, 618-623.
Seo JB et al. Epithelial monolayer culture system for real-time single-cell analyses, Phys Rep. 2014, 2(4):e12002, p. 1-3.
Simon AK et al. Polymer-Based Mesh as Supports for Multi-layered 3D Cell Culture and Assays, Biomaterials. 2014; 35(1):1-21, abstract.
Soofi, S.S. et al., "The elastic modulus of Matrigel™ as determined by atomic force microscopy" Journal of Structural Biology 167, 216-219 (2009).
Speer et al., "Molecular transport through primary human small intestinal monolayers by culture on a collagen scaffold with a gradient of chemical cross-linking", Joumal of Biological Engineering (Apr. 27, 2019).
Spence, Jason el al. "Directed differentiation of human pluripotent stem cells into intestinal tissue in vitro", Nature, 470(7332):105-109 (2011).
Szymanski P et al. Adaptation of High-Throughput Screening in Drug Discovery—Toxicological Screening Tests, Int J Mol Sci. 2012, 13:427-452, abstract.
Sträter et al. Rapid Onset of Apoptosis In Vitro Follows Disruption of beta 1-Integrin/Matrix Interactions in Human Colonic Crypt Cells. Gastroenterology (1996), 110, 1776-1784. (Year: 1996).
T. Sato, D. E. Stange, M. Ferrante, R. G. Vries, J. H. Van Es, S. Van den Brink, W. J. Van Houdt, A. Pronk, J. Van Gorp, P. D. Siersema and H. Clevers. Long-term expansion of epithelial organoids from human colon, adenoma, adenocarcinoma, and Barrett's epitheiuum. Gastroenterology, 2011, 141, 1762-1772.
Sato, et. al. "Paneth Cells constitute the niche for Lgr5 stem cells in intestinal crypts," Nature, 469(7330), pp. 415-418 (2011).
T. Sato, R. G. Vries, H. J. Snippert, M. van de Wetering, N. Barker, D. E. Stange, J. H. van Es, A. Abo, P. Kujala, P. J. Peters and H. Clevers. Single Lgr5 stem cells build crypt-villus structures in vitro without a mesenchymal niche. Nature, 2009, 459, 262-U147.
T. Yen and N. Wright, The gastrointestinal tract stem cell niche, Stem Cell Rev. 2(3), 203-212 (2006).
Tang et al. Utilization of a Human Intestinal Epithelial Cell Culture System (Caco-2) for Evaluating Cytoprotective Agents. Pharm Res (1993), v10(11), p. 1620-1626. (Year: 1993).
Transwell® permeable supports (2007), 8 pages. (Year: 2007).
Wang et al., "Formation of Human Colonic Crypt Array by Application of Chemical Gradients Across a Shaped Epithelial Monolayer", Cellular and Molecular Gastroenterology and Hepatology. vol. 5, No. 2, pp. 113-130 (2018).
Wang et al. Influence of micro-well biomimetic topography on intestinal epithelial Caco-2 cell phenotype. Biomaterials (2009), v30, p. 6825-6834. (Year: 2009).
Wang et al., "Synergic effects of crypt-like topography and ECM proteins on intestinal cell behavior in collagen based membranes," Biomaterials, vol. 31, Iss. 29, pp. 7586-7598 (2010).
Wang, Yuli et al. "A microengineered collagen scaffold for generating a polarized crypt-vilus architecture of human small intestinal epithelium", Biomaterials, 128:44-45 (2017).
Wang et al., "Building a Thick Mucus Hydrogel Layer to Improve the Physiological Relevance of In Vitro Primary Colonic Epithelial Models," Cellular and Molecular Gastroenterology and Hepatology, Jul. 26, 2019 (Jul. 26, 2019), vol. 8, Iss. 4, pp. 653-655.
Watson, Carey et al. "An in vivo model of human small intestine using pluripotent stem cells", Nature Medicine, 20(11)1310-1314 (2014).
Written Opinion and International Search Report corresponding to International Application No. PCT/US2016/015631 dated May 26, 2016.
Written Opinion and International Search Report corresponding to International Application No. PCT/US2017/043601 dated Nov. 16, 2017.
Written Opinion of the International Searching Authority corresponding to International Application No. PCT/US2019/032393 dated Jul. 23, 2019.
Written Opinion of the International Searching Authority corresponding to International Application No. PCT/US2019/033955 dated Aug. 15, 2019.
Written Opinion of the International Searching Authority corresponding to International Application No. PCT/US2019/061743 dated Feb. 11, 2020.
Yeste et al., "Engineering and monitoring cellular barrier models," Journal of Biological Engineering, Sep. 12, 2018 (Sep. 12, 2018), vol. 12, No. 18, pp. 1-19.

(56) References Cited

OTHER PUBLICATIONS

X. Yin, H. F. Farin, J. H. van Es, H. Clevers, R. Langer and J. M. Karp. Niche-independent high-purity cultures of Lgr5+ intestinal stem cells and their progeny. Nature Methods, 2014, 11, 106-112.
Di et al. "Collagen stabilization and modification using a polyepoxide, triglycidyl isocyanurate," Polymer Degradation and Stability, 94, 1684-1692 (2009).
Y. L. Wang, A. A. Ahmad, C. E. Sims, S. T. Magness and N. L. Allbritton. In vitro generation of colonic epithelium from primary cells guided by microstructures. Lab Chip, 2014, 14, 1622-1631.
Y. W. Liu, L. H. Gan, D. J. Carlsson, P. Fagerholm, N. Lagali, M. A. Watsky, R. Munger, W. G. Hodge, D. Priest and M. Griffith, "A Simple, Cross-linked Collagen Tissue Substitute for Corneal Implantation", Invest. Ophthalmol Invest. Ophthalmol. Vis. Sci., 2006, 47, 1869-1875.
Anonye, B. O. et al. Probing host-anaerobe interactions in innovative human gut cellular models. bioRxiv, doi:10.1101/269035, 43 pages (2018).
Anonye et al. Probing Clostridium difficule infection in innovative human gut cellular models, bioRxiv, 269035, 28 pages (2018).
Bertout, J. A., Patel, S. A. & Simon, M. C. The impact of O2 availability on human cancer. Nature reviews. Cancer 8, 967, 22 pages (2008).
Blouin, J. M. et al. Butyrate elicits a metabolic switch in human colon cancer cells by targeting the pyruvate dehydrogenase complex. International journal of cancer 128, 2591-2601 (2011).
Boccellato et al. "Polarised epithelial monolayers of the gastric mucosa reveal insights into mucosa! homeostasis and defence against infection," Gut, Feb. 7, 2018 (Feb. 7, 2018), vol. 68, pp. 400-413.
Brennan, M. D., Rexius-Hall, M. L. & Eddington, D. T. A 3D-printed oxygen control insert for a 24-well plate. PloS one 10, e0137631, 9 pages (2015).
Buchwald, P. FEM-based oxygen consumption and cell viability models for avascular pancreatic islets. Theoretical Biology and Medical Modelling 6, 5, 13 pages (2009).
Byrne, M. B., Leslie, M. T., Gaskins, H. R. & Kenis, P. J. "Methods to study the tumor microenvironment under controlled oxygen conditions," Author manuscript, 19 pages, published in final edited form as: Trends in biotechnology 32, 556-563 (2014).
Cani, P. D. "Gut microbiota—at the intersection of everything?" Abstract of Nature Reviews Gastroenterology & Hepatology 14, 321-322 (2017) [6 pages].
Chen, Y. et al. "Robust bioengineered 3D functional human intestinal epithelium," Scientific reports 5, 13708, 11 pages (2015).
Chen, Y.-A. et al. "Generation of oxygen gradients in microfluidic devices for cell culture using spatially confined chemical reactions," Abstract of Lab on a Chip 11, 3626-3633, 6 pages (2011).
Colgan, S. P. & Taylor, C. T. "Hypoxia: an alarm signal during intestinal inflammation," Author Manuscript, published in final edited form as: Nature Reviews Gastroenterology and Hepatology 7, 281-287 (2010) [16 pages].
Colgan, S.P., Dzus, A.L. & Parkos, C.A. "Epithelial exposure to hypoxia modulates neutrophil transepithelial migration," Journal of Experimental Medicine 184, 1003-1015 (1996).
Eveillard, M. et al. "Identification and characterization of adhesive factors of Clostridium difficile involved in adhesion to human colonic enterocyte-like Caco-2 and mucus-secreting HT29 cells in culture," Molecular microbiology 7, pp. 371-381 (1993).
Gersemann, M. et al. "Differences in goblet cell differentiation between Crohn's disease and ulcerative colitis," Abstract of Differentiation 77, pp. 84-94 (2009)[3 pages].
Gibson et al. "Isolation of Colonic Crypts That Maintain Structural and Metabolic Viability In Vitro," Gastroenterology, 1989, vol. 96, pp. 283-291 (Year: 1989).
Gross, M. W., Karbach, U., Groebe, K., Franko, A. J. & Mueller-Klieser, W. "Calibration of misonidazole labeling by simultaneous measurement of oxygen tension and labeling density in multicellular spheroids," International journal of cancer 61, 567-573 (1995).
Huang, Y., Zitta, K., Bein, B., Steinfath, M. & Albrecht, M. An insert-based enzymatic cell culture system to rapidly and reversibly induce hypoxia: investigations of hypoxia-induced cell damage, protein expression and phosphorylation in neuronal IMR-32 cells. Disease models & mechanisms 6, 1507-1514 (2013).
Hubbi, M.E. & Semenza, G.L. Regulation of cell proliferation by hypoxia-inducible factors. American Journal of Physiology-Cell Physiology 309, C775-C782 (2015).
Ivanovic, Z. Hypoxia or in situ normoxia: The stem cell paradigm. Journal of cellular physiology 219, 271-275 (2009).
JanssenDuijghuijsen, L.M. et al. Mitochondrial ATP Depletion Disrupts Caco-2 Monolayer Integrity and Internalizes Claudin 7. Frontiers in Physiology 8 (2017).
Janvilisri, T., Scaria, J. & Chang, Y.-F. Transcriptional profiling of Clostridium difficile and Caco-2 cells during infection. The Journal of infectious diseases 202, 282-290 (2010).
Kaidi, A., Williams, A.C. & Paraskeva, C. Interaction between B-catenin and HIF-1 promotes cellular adaptation to hypoxia. Nature cell biology 9, 210-217 (2007).
Kaiko, G. E. & Stappenbeck, T. S. Host-microbe interactions shaping the gastrointestinal environment. Trends in immunology 35, 538-548 (2014).
Kelly, C.J. et al. Fundamental role for HIF-1$\alpha$in constitutive expression of human $\beta$ defensin-1. Mucosal Immunology 6, 1110 (2013).
Kim, H. J., Li, H., Collins, J. J. & Ingber, D. E. Contributions of microbiome and mechanical deformation to intestinal bacterial overgrowth and inflammation in a human gut-on-a-chip. Proceedings of the National Academy of Sciences 113, E7-E15 (2016).
Kim, Y.-G. et al. Neonatal acquisition of *Clostridia* species protects against colonization by bacterial pathogens. Science 356, 315-319, doi:10.1126/science.aag2029 (2017).
Koh, M. Y. & Powis, G. Passing the baton: the HIF switch. Trends in biochemical sciences 37, 364-372 (2012).
Lamberti, A., Marasso, S. L. & Cocuzza, M. PDMS membranes with tunable gas permeability for microfluidic applications. Rsc Advances 4, 61415-61419 (2014).
LeBlanc, J. G. et al. Bacteria as vitamin suppliers to their host: a gut microbiota perspective. Current opinion in biotechnology 24, 160-168 (2013).
Leffler, D.A. & Lamont, J.T. Clostridium difficile Infection. New England Journal of Medicine 372, 1539-1548 (2015).
Lynch, S.V. & Pedersen, O. The Human Intestinal Microbiome in Health and Disease. N Engl J Med 375, 2369-2379 (2016).
Markov, D. A., Lillie, E. M., Garbett, S. P. & McCawley, L. J. Variation in diffusion of gases through PDMS due to plasma surface treatment and storage conditions. Biomedical microdevices 16, 91-96 (2014).
Marzorati, M. et al. The HMI™ module: a new tool to study the Host-Microbiota Interaction in the human gastrointestinal tract in vitro. BMC microbiology 14, 133 (2014).
Nagpal, R., Yadav, H. & Marotta, F. Gut microbiota: the next-gen frontier in preventive and therapeutic medicine? Frontiers in medicine 1 (2014).
Oppegard, S. C. & Eddington, D. T. A microfabricated platform for establishing oxygen gradients in 3-D constructs. Biomedical microdevices 15, 407-414 (2013).
Oppegard, S. C., Blake, A. J., Williams, J. C. & Eddington, D. T. Precise control over the oxygen conditions within the Boyden chamber using a microfabricated insert. Lab on a chip 10, 2366-2373 (2010).
Oppegard, S. C., Nam, K.-H., Carr, J. R., Skaalure, S. C. & Eddington, D. T. Modulating temporal and spatial oxygenation over adherent cellular cultures. PloS one 4, e6891 (2009).
Peery, A.F. et al. Burden of gastrointestinal disease in the United States: 2012 update. Gastroenterology 143, 1179-1187. e1173 (2012).
Quaroni et al. "Epithelioid Cell Cultures From Rat Small Intestine," J. Cell Biology, 1979, vol. 80, pp. 248-265 (Year: 1979).
Ex Parte Quayle Action and Interview Summary corresponding to U.S. Appl. No. 15/545,456 dated Mar. 16, 2021.
Rexius-Hall, M. L., Mauleon, G., Malik, A. B., Rehman, J. & Eddington, D. T. Microfluidic platform generates oxygen landscapes for localized hypoxic activation. Lab on a chip 14, 4688-4695 (2014).

(56) References Cited

OTHER PUBLICATIONS

Sampson, T. R. et al. Gut microbiota regulate motor deficits and neuroinflammation in a model of Parkinson's disease. Cell 167, 1469-1480. e1412 (2016).
Schneeberger, K., Roth, S., Nieuwenhuis, E.E. & Middendorp, S. Intestinal epithelial cell polarity defects in disease: lessons from microvillus inclusion disease. Disease models & mechanisms 11, dmm031088 (2018).
Schuijers, J. & Clevers, H. Adult mammalian stem cells: the role of Wnt, Lgr5 and R-spondins. The EMBO journal 31, 2685-2696 (2012).
Shah, P. et al. A microfluidics-based in vitro model of the gastrointestinal human-microbe interface. Nature communications 7 (2016).
Shimamura, S. et al. Relationship Between Oxygen Sensitivity and Oxygen Metabolism of *Bifidobacterium* Species. Journal of Dairy Science 75, 3296-3306 (1992).
Simon, M. C. & Keith, B. The role of oxygen availability in embryonic development and stem cell function. Nature reviews. Molecular cell biology 9, 285 (2008).
Skolimowski, M. et al. Microfluidic dissolved oxygen gradient generator biochip as a useful tool in bacterial biofilm studies. Lab on a Chip 10, 2162-2169 (2010).
Sommer, F., Anderson, J.M., Bharti, R., Raes, J. & Rosenstiel, P. The resilience of the intestinal microbiota influences health and disease. Nat Rev Microbiol 15, 630-638 (2017).
Tsujii, M. et al. Colonic mucosal hemodynamics and tissue oxygenation in patients with ulcerative colitis: Investigation by organ reflectance spectrophotometry. Journal of Gastroenterology 30, 183-188 (1995).
Uchida, H., Sato, A., Miyayama, A. & Tsukada, K. Generation of an oxygen gradient in a microfluidic device and cellular analysis in hypoxia. Advanced Biomedical Engineering 2, 143-149 (2013).
Ulluwishewa, D. et al. Live Faecalibacterium prausnitzii in an apical anaerobic model of the intestinal epithelial barrier. Cellular microbiology 17, 226-240 (2015).
Varia, M.A. et al. Pimonidazole: a novel hypoxia marker for complementary study of tumor hypoxia and cell proliferation in cervical carcinoma. Gynecologic oncology 71, 270-277 (1998).
Wagner, B.A., Venkataraman, S. & Buettner, G.R. The rate of oxygen utilization by cells. Free radical biology & medicine 51, 700-712 (2011).
Waligora, A.J., Barc, M.C., Bourlioux, P., Collignon, A. & Karjalainen, T. Clostridium difficile cell attachment is modified by environmental factors. Applied and environmental microbiology 65, 4234-4238 (1999).
Walsh III, D. I. et al. Emulation of Colonic Oxygen Gradients in a Microdevice. SLAS Technology: Translating Life Sciences Innovation, 2472630317743425 (2017).
Wang, Y. et al. Bioengineered Systems and Designer Matrices That Recapitulate the Intestinal Stem Cell Niche. Cell Mol Gastroenterol Hepatol 5, 440-453 e441 (2018).
Wang, Y. et al. Self-renewing monolayer of primary colonic or rectal epithelial cells. Cellular and Molecular Gastroenterology and Hepatology (2017).
Wang et al. "Capture and 3D culture of colonic crypts and colonoids in a microarray platform," Lab Chip, The Royal Society of Chemistry, vol. 13, pp. 4625-4634 (2013b).
Ward, J. B., Keely, S. J. & Keely, S. J. "Oxygen in the regulation of intestinal epithelial transport," The Journal of physiology 592, pp. 2473-2489 (2014).
Wiegand, P.N. et al. Clinical and economic burden of Clostridium difficile infection in Europe: a systematic review of healthcare-facility-acquired infection. Journal of Hospital Infection 81, 1-14 (2012).
Zeitouni, N. E., Chotikatum, S., von Köckritz-Blickwede, M. & Naim, H. Y. The impact of hypoxia on intestinal epithelial cell functions: consequences for invasion by bacterial pathogens. Molecular and cellular pediatrics 3, 14 (2016).
Zheng, L., Kelly, C. J. & Colgan, S. P. "Physiologic hypoxia and oxygen homeostasis in the healthy intestine. A review in the theme: cellular responses to hypoxia," American Journal of Physiol Cell Physiol 309, pp. C350-C360 (2015).
Zhou, W. et al. Multifunctional bioreactor system for human intestine tissues. ACS biomaterials science & engineering 4, 231-239 (2017).
Barkla et al. "The fate of epithelial cells in the human large intestine." Pathology vol. 31, pp. 230-238, (1999).
Bartfeld, "Modeling infectious diseases and host-microbe interactions in gastrointestinal organoids." Developmental biology, vol. 420, pp. 262-270, (2016).
Basak et al., "Induced quiescence of Lgr5+ stem cells in intestinal organoids enables differentiation of hormone-producing enteroendocrine cells." Cell Stem Cell, vol. 20, pp. 177-190 e4, (2017).
Dekkers et al., "A functional CFTR assay using primary cystic fibrosis intestinal organoids." Nature medicine, vol. 19, pp. 939, (2013).
Finkbeiner et al., "Stem cell-derived human intestinal organoids as an infection model for rotaviruses." MBio vol. 3, e00159-12, (2012).
Gamet et al., "Effects of short-chain fatty acids on growth and differentiation of the human colon-cancer cell line HT29." International Journal of Cancer vol. 52, pp. 286-289, (1992).
Gattazzo et al., "Extracellular matrix: a dynamic microenvironment for stem cell niche." Biochimica et Biophysica Acta (BBA)—General Subjects, vol. 1840, pp. 2506-2519, (2014).
Hall et al., "Human genetic variation and the gut microbiome in disease." Nature Reviews Genetics vol. 18, pp. 690, (2017).
In et al., "Enterohemorrhagic *Escherichia coli* reduces mucus and intermicrovillar bridges in human stem cell-derived colonoids." Cellular and molecular gastroenterology and hepatology vol. 2, pp. 48-62 e3, (2016).
Ito et al., "Metabolism and the control of cell fate decisions and stem cell renewal." Annual review of cell and developmental biology. vol. 32, pp. 399-409, (2016).
Kaiko et al., "The colonic crypt protects stem cells from microbiota-derived metabolites." Cell vol. 165, pp. 1708-1720, (2016).
Karve et al., "Intestinal organoids model human responses to infection by commensal and Shiga toxin producing *Escherichia coli*." PloS one vol. 12, e0178966, (2017).
Kozuka et al., "Development and Characterization of a Human and Mouse Intestinal Epithelial Cell Monolayer Platform." Stem cell reports vol. 9, pp. 1976-1990, (2017).
Li et al., "Role of mechanical factors in fate decisions of stem cells." Regenerative medicine vol. 6, pp. 229-240, (2011).
Semrau et al., "Studying lineage decision-making in vitro; emerging concepts and novel tools." Annual review of cell and developmental biology vol. 31, pp. 317-345, (2016).
Shreiner et al., "The gut microbiome in health and in disease." Current opinion in gastroenterology vol. 31, p. 69, (2015).
Terryn et al., "Recent advances in lineage differentiation from stem cells: hurdles and opportunities?" F1000Resarch vol. 7, (2018).
Tong et al., "Towards a defined ECM and small molecule based monolayer culture system for the expansion of mouse and human intestinal stem cells." Biomaterials vol. 154, pp. 60-73, (2018).
Tremlett et al., "The gut microbiome in human neurological disease: a review." Annals of Neurology, (2017).
Tsubouchi, "Kinetic analysis of epithelial cell migration in the mouse descending colon." Developmental Dynamics, vol. 161, pp. 239-246, (1981).
Van Es et al., "DII1+ secretory progenitor cells revert to stem cells upon crypt damage." Nature cell biology vol. 14, pp. 1099, (2012).
Wang et al., "In vitro Generation of Mouse Colon Crypts." ACS biomaterials science & engineering vol. 3, pp. 2502-2513, (2017).
Whitehead et al., "Effects of short-chain fatty acids on a new human colon carcinoma cell line (LIM1215)." Gut, vol. 27, pp. 1457-1463, (1986).
Young, "The role of the microbiome in human health and disease: an introduction for clinicians." BMJ vol. 356, j831, (2017).
Xu et al., "Butyrate induces apoptosis by activating PDC and inhibiting complex I through SIRT3 inactivation." Signal Transduction and Targeted Therapy, vol. 2, pp. e16035, (2017).

(56) References Cited

OTHER PUBLICATIONS

Fung et al., "Butyrate-Induced Apoptosis in HCT116 Colorectal Cancer Cells Includes Induction of a Cell Stress Response." Journal of Proteome Research, vol. 10, pp. 1860-1869 (2011).
Ruemmele et al., "Butyrate induced Caco-2 cell apoptosis is mediated via the mitochondrial pathway." Gut, vol. 52, pp. 94-100, (2003).
Koh et al., "From Dietary Fiber to Host Physiology: Short-Chain Fatty Acids as Key Bacterial Metabolites." Cell, vol. 165, pp. 1332-1345, (2016).
Barker, "Adult intestinal stem cells: critical drivers of epithelial homeostasis and regeneration." Nature Reviews Molecular Cell Biology, vol. 15, pp. 19-33 (2014).
Sternini et al., "Enteroendocrine cells: a site of 'taste' in gastrointestinal chemosensing." Current Opinion in Endocrinology, Diabetes, and Obesity, vol. 15, pp. 73, (2008).
Birchenough et al., "A sentinel goblet cell guards the colonic crypt by triggering Nlrp6-dependent Muc2 secretion." Science, vol. 352, pp. 1535-1542, (2016).
Valenta et al., "The many faces and functions of β-catenin." The EMBO Journal, vol. 31, pp. 2714-2736, (2012).
Provenzano and Keely, "Mechanical signaling through the cytoskeleton regulates cell proliferation by coordinated focal adhesion and Rho GTPase signaling", J. Cell Sci, vol. 124, pp. 1195-1205, (2011).
Yim and Sheetz, "Force-dependent cell signaling in stem cell differentiation." Stem Cell Research & Therapy, vol. 3, pp. 41, (2012).
Lü et al., "Differential regulation of morphology and stemness of mouse embryonic stem cells by substrate stiffness and topography," Biomaterials, vol. 35, pp. 3945-3955, (2014).
Chowdhury et al., "Soft Substrates Promote Homogeneous Self-Renewal of Embryonic Stem Cells via Downregulating Cell-Matrix Tractions." PloS one, vol. 5, e15655, (2010).
Janshoff et al., "Cell Adhesion to Ordered Pores: Consequences for Cellular Elasticity." Journal of Adhesion Science and Technology, vol. 24, pp. 2287-2300, (2010).
Rother et al., "Cytoskeleton remodelling of confluent epithelial cells cultured on porous substrates." Journal of the Royal Society Interface, vol. 12, 20141057, (2015).
Hayman et al., "Growth of human stem cell-derived neurons on solid three-dimensional polymers." Journal of Biochemical and Biophysical Methods, vol. 62, pp. 231-240, (2005).
Peyton et al., "Marrow-Derived Stem Cell Motility in 3D Synthetic Scaffold Is Governed by Geometry Along With Adhesivity and Stiffness." Biotechnology and Bioengineering, vol. 108, pp. 1181-1193, (2011).
Ahmad et al., "Optimizing Wnt-3a and R-spondin1 concentrations for stem cell renewal and differentiation in intestinal organoids using a gradient-forming microdevice." RSC Advances, vol. 5, pp. 74881-74891 (2015).
Franck et al., "Three-Dimensional Traction Force Microscopy: A New Tool for Quantifying Cell-Matrix Interactions." PloS one, vol. 6, e17833, (2011).
Qu et al., "Maturation State and Matrix Microstructure Regulate Interstitial Cell Migration in Dense Connective Tissues." Scientific Reports, vol. 8, 3295, (2018).
Vallo et al., "Elastic Modulus and Yield Stress of Epoxy Networks in the Glassy State." Polymer Gels and Networks, vol. 1, pp. 257-266, (1993).
Engelberg and Tesoro, "Mechanical and Thermal Properties of Epoxy Resins With Reversible Crosslinks," Polymer Engineering & Science, vol. 30, pp. 303-307, (1990).
Faul et al., "G*Power 3: A flexible statistical power analysis program for the social, behavioral, and biomedical sciences," Behavior Research Methods, vol. 39, pp. 175-191, (2007).
Schindelin et al., "Fiji—an Open Source platform for biological image analysis." Nature Methods, vol. 9, pp. 676, (2012).
Pai et al., "Photoresist with Low Fluorescence for Bioanalytical Applications," Analytical Chemistry, vol. 79, pp. 8774-8780, (2007).
Allen et al., "Adherent and soluble Mucus in the Stomach and Duodenum." Digestive Diseases and Sciences vol. 30, 55S-62S, (1985).
Pelaseyed et al., "The mucus and mucins of the goblet cells and enterocytes provide the first defense line of the gastrointestinal tract and interact with the immune system." Immunological reviews vol. 260, pp. 8-20, (2014).
Murgia et al., "The role of mucus on drug transport and its potential to affect therapeutic outcomes." Adv Drug Deliv Rev vol. 124, pp. 82-97, (2018).
Lehr et al., "An estimate of turnover time of intestinal mucus gel layer in the rat in situ loop." International Journal of Pharmaceutics vol. 70 pp. 235-240, (1991).
Wei et al., "Fatty Acid Synthase Modulates Intestinal Barrier Function through Palmitoylation of Mucin 2." Cell Host & Microbe vol. 11, pp. 140-152, (2012).
Johansson et al., "The inner of the two Muc2 mucin-dependent mucus layers in colon is devoid of bacteria." Proceedings of the National Academy of Sciences of the United States of America, vol. 105, pp. 15064-15069, (2008).
Hansson, "Role of mucus layers in gut infection and inflammation." Current Opinion in Microbiology vol. 15, pp. 57-62, (2012).
Carlson et al., "Engineering the Mucus Barrier." Annual Review of Biomedical Engineering vol. 20, pp. 197-220, (2018).
Werlang et al., "Engineering mucus to study and influence the microbiome." Nature Reviews Materials vol. 4, pp. 134-145, (2019).
Rogier et al., "Secretory IgA is Concentrated in the Outer Layer of Colonic Mucus along with Gut Bacteria." Pathogens vol. 3, pp. 390-403, (2014).
Gunasekara et al., "A Monolayer of Primary Colonic Epithelium Generated on a Scaffold with a Gradient of Stiffness for Drug Transport Studies." Analytical Chemistry vol. 90, pp. 13331-13340, (2018).
Quigley, "Gut bacteria in health and disease." Gastroenterology & hepatology vol. 9, pp. 560-569, (2013).
Gagnon et al., "Comparison of the Caco-2, HT-29 and the mucus-secreting HT29-MTX intestinal cell models to investigate *Salmonella* adhesion and invasion," Journal of Microbiological Methods, vol. 94, pp. 274-279 (2013).
Lesuffleur et al., "Growth adaptation to methotrexate of HT-29 human colon carcinoma cells is associated with their ability to differentiate into columnar absorptive and mucus-secreting cells." Cancer Research vol. 50, pp. 6334-6343, (1990).
Nusrat et al., "Clostridium difficile Toxins Disrupt Epithelial Barrier Function by Altering Membrane Microdomain Localization of Tight Junction Proteins." Infection and Immunity vol. 69, pp. 1329-1336, (2001).
Date et al., "Mini-Gut Organoids: Reconstitution of Stem Cell Niche." Annual Review of Cell and Developmental Biology vol. 31, pp. 269-289, (2015).
Fatehullah et al., "Cell and tissue polarity in the intestinal tract during tumourigenesis: cells still know the right way up, but tissue organization is lost." Philosophical Transactions of the Royal Society B—Biological Sciences vol. 368, 20130014, (2013).
Noel et al., "A primary human macrophage-enteroid co-culture model to investigate mucosal gut physiology and host pathogen interactions." Scientific Reports vol. 7, pp. 45270, (2017).
Puzan et al., "Enteric Nervous System Regulation of Intestinal Stem Cell Differentiation and Epithelial Monolayer Function." Scientific Reports vol. 8, pp. 6313, (2018).
Wang et al., "Analysis of Interleukin 8 Secretion by a Stem-Cell-Derived Human-Intestinal-Epithelial-Monolayer Platform." Analytical Chemistry vol. 90, pp. 11523-11530, (2018).
Whitcutt et al., "A biphasic chamber system for maintaining polarity of differentiation of cultured respiratory tract epithelial cells." In Vitro Cellular & Developmental Biology, vol. 24, pp. 420-428, (1988).
Gray et al., "Mucociliary differentiation of serially passaged normal human tracheobronchial epithelial cells," American Journal of Respiratory Cell and Molecular Biology, vol. 14, pp. 104-112 (1996).
Raredon et al., "A Rotating Bioreactor for Scalable Culture and Differentiation of Respiratory Epithelium." Cell Medicine vol. 7, pp. 109-121, (2012).

(56) References Cited

OTHER PUBLICATIONS

O'Boyle et al., "Temporal dynamics of ovine airway epithelial cell differentiation at an air-liquid interface." Plos One vol. 12, e0181583, (2017).
Ootani et al., "An air-liquid interface promotes the differentiation of gastric surface mucous cells (GSM06) in culture." Biochemical and Biophysical Research Communications vol. 271, pp. 741-746, (2000).
Yokoyama et al., "Differentiation of gastric surface mucous cells (GSM06) induced by air-liquid interface is regulated partly through mitogen-activated protein kinase pathway." Journal of Gastroenterology and Hepatology, vol. 22, pp. 2310-2315, (2007).
Navabi et al., "Gastrointestinal Cell Lines Form Polarized Epithelia with an Adherent Mucus Layer when Cultured in Semi-Wet Interfaces with Mechanical Stimulation." Plos One vol. 8, e68761, (2013).
Elkins et al., "Mechanisms and applications of hypertonic saline." Journal of the Royal Society of Medicine, vol. 104, pp. S2-S5, (2011).
Tu et al., "Effect of osmotic response element binding protein on mucus secretion with hypertonicity in human airway epithelial cells," Zhonghua Yi Xue Za Zhi, vol. 91, pp. 549-553, (2011) [English Abstract].
Lüdeking et al., "Osmotic changes and ethanol modify TFF gene expression in gastrointestinal cell lines." Febs Letters vol. 439, pp. 180-184, (1998).
Shields et al., "Absorption and secretion of water and electrolytes by the intact colon in a patient with primary aldosteronism." British Medical Journal vol. 1, pp. 93-96, (1968).
Wapnir et al., "Regulation mechanisms of intestinal secretion: implications in nutrient absorption." The Journal of Nutritional Biochemistry vol. 13, pp. 190-199, (2002).
Koch et al., "Plasma vasoactive intestinal polypeptide concentration determination in patients with diarrhea." Gastroenterology vol. 100, pp. 99-106, (1991).
Schwartz et al., "Vasoactive intestinal peptide stimulation of adenylate cyclase and active electrolyte secretion in intestinal mucosa." Journal of Clinical Investigation vol. 54, pp. 536-544, (1974).
Wu et al., "Vasoactive Intestinal Polypeptide Promotes Intestinal Barrier Homeostasis and Protection Against Colitis in Mice." Plos One vol. 10, e0125225, (2015).
Johansson et al., "Bacteria penetrate the normally impenetrable inner colon mucus layer in both murine colitis models and patients with ulcerative colitis." Gut, vol. 63, pp. 281-291, (2014).
Lin et al., "Air-liquid interface (ALI) culture of human bronchial epithelial cell monolayers as an in vitro model for airway drug transport studies." Journal of Pharmaceutical Sciences vol. 96, pp. 341-350, (2007).
Bernstam et al., "Keratinocytes grown at the air-liquid interface." In Vitro Cellular & Developmental Biology vol. 22, pp. 695-705, (1986).
Ootani et al., "Sustained in vitro intestinal epithelial culture within a Wnt-dependent stem cell niche." Nature Medicine vol. 15, pp. 1-U140, (2009).
Voth et al., "Clostridium difficile toxins: mechanism of action and role in disease." Clinical microbiology reviews vol. 18, pp. 247-263, (2005).
He et al., "Clostridium difficile toxin A triggers human coloncyte IL-8 release via mitochondrial oxygen radical generation." Gastroenterology, vol. 122, pp. 1048-1057, (2002).
Mahida et al., "Effect of Clostridium difficile toxin A on human intestinal epithelial cells: induction of interleukin 8 production and apoptosis after cell detachment." Gut vol. 38, pp. 337-347, (1996).
Haller et al., "Non-pathogenic bacteria elicit a differential cytokine response by intestinal epithelial cell/leucocyte co-cultures." Gut vol. 47, pp. 79-87, (2000).
Parlesak et al., "Modulation of Cytokine Release by Differentiated CACO-2 Cells in a Compartmentalized Coculture Model with Mononuclear Leucocytes and Nonpathogenic Bacteria." Scandinavian Journal of Immunology vol. 60, pp. 477-485, (2004).
English Translation of Notice of Allowance corresponding to JP Patent Application No. JP 2017-540628 dated Jun. 29, 2021.
English Translation of First Office Action corresponding to JP Patent Application No. JP 2019-504019 dated May 25, 2021.
Canadian Office Action for Application No. 3093581 dated Aug. 23, 2023.
Canadian Office Action for Application No. 3093585 dated Aug. 28, 2023.
Canadian Office Action for Application No. 3112220 dated Sep. 1, 2023.
Canadian Office Action for Application No. 3170294 dated Sep. 11, 2023.
Japanese Office Action for Application No. 2021517604 dated Aug. 21, 2023.
Japanese Decision to Grant for Application No. 2020560193 dated Sep. 19, 2023.
European Office Action for Application No. 16744178 dated Oct. 10, 2023.
Non-Final Office Action for U.S. Appl. No. 18/371,636 dated Nov. 6, 2023.
Canadian Office Action for Application No. 3052250 dated May 12, 2023.
Japanese Office Action for Application No. 2022560193 dated Apr. 25, 2023.
Japanese Office Action for Application No. 2020565308 dated Apr. 18, 2023.
Japanese Office Action for Application No. 2021517604 dated Jan. 31, 2024.
Canadian Office Action for Application No. 3009153 dated Mar. 13, 2024.
Bhat et al., "The limiting role of mucus in drug absorption: drug permeation through mucus solution," International Journal of Pharmaceutics, vol. 126, No. 1-2: 179-187 (Dec. 1995).
Gunawardene Ashok R. et al., "Classification and functions of enteroendocrine cells of the lower gastrointestinal tract: Classification and functions of colorectal enteroendocrine cells," International Review of Experiemental Pathology, vol. 92, No. 4: 219-231 (Aug. 31, 2011).
Extended European Search Report for EP Application No. 21779789.3, dated Jun. 10, 2024, 13 pages.
Hokari et al., "Vasoactive intestinal peptide upregulates MUC2 intestinal mucin via CREB/ATF1," American Journal of Physiology-Gastrointestinal and Liver Physiology, vol. 289, No. 5: G949-G959 (2005).
Canadian Office Action in CA Application No. 3093585, dated Apr. 25, 2025, 6 pages.
Crosnier et al., "Organizing cell renewal in the intestine: stem cells, signals and combinatorial control," Nature Reviews Genetics, vol. 7: 349-359 (2006).
Flier et al., "Stem Cells, Self-Renewal, and Differentiation in the Intestinal Epithelium," Annual Review of Physiology, vol. 71: 241-260 (2009)—Abstract.
Galland, "The gut microbiome and the brain," Journal of Medicinal Food, vol. 17: 1261-1272 (2014).
Goldszmid et al., "The price of immunity," Nature Immunology, vol. 13: 932-938 (2012).
Leonel et al., "Butyrate: Implications for intestinal function," Current Opinion in Clinical nutrition & Metabolic Care, vol. 15: 474-479 (2012).
Ren et al., "Short-Chain Fatty Acids Induce Intestinal Epithelial Heat Shock Protein 25 Expression in Rats and IEC 18 Cells," Gastroenterology, vol. 121: 631-639 (2001).
Takano et al., "Microfluidic cell culture system with on-chip hypoxic conditioning," In: Engineering in Medicine and Biology Society (EMBC), 35th Annual International Conference of the IEEE EMBS: 4474-4477 (2013).
Japanese Office Action in JP Application No. 2022-559825, dated Apr. 1, 2025, 4 pages.
Japanese Office Action in JP Application No. 2024-033959 dated Jun. 10, 2025, 3 pages.
Lock et al., "Mucus models to evaluate the diffusion of drugs and particles," Advanced Drug Delivery Reviews, vol. 124: 34-39 (2018).

(56) References Cited

OTHER PUBLICATIONS

Sontheimer-Phelps et al., "Human Colon-on-a-Chip Enables Continuous In Vitro analysis of Colon Mucus Layer Accumulation and Physiology," cellular and Molecular Gastroenterology and Hepatologyl, vol. 9, No. 3: 507-526 (2020).

* cited by examiner

FORMATION OF ARRAYS OF PLANAR INTESTINAL CRYPTS POSSESSING A STEM/PROLIFERATIVE CELL COMPARTMENT AND DIFFERENTIATED CELL ZONE

CROSS REFERENCE TO RELATED APPLICATIONS

This application claims priority to International Patent Application No. PCT/US2019/033955, filed May 24, 2019, which claims the benefit of and priority to U.S. Provisional Patent Application Ser. No. 62/676,418, filed May 25, 2018, the disclosures of each of which are incorporated herein by reference in its entirety their entireties.

STATEMENT OF GOVERNMENT SUPPORT

This invention was made with government support under grant number DK109559 awarded by the National Institutes of Health. The government has certain rights to this invention.

TECHNICAL FIELD

The presently disclosed subject matter relates to methods for producing tissue constructs comprising two or more physically distinct regions that comprise different cell populations or lineages. The presently disclosed subject matter further relates to methods and apparatus for producing the tissue constructs and to methods of using the tissue constructs.

BACKGROUND

Development of in vitro culture systems such as, for example, intestinal organoid cultures, intestinal self-renewing monolayers, and gut-on-a-chip type devices, offer useful in vitro platforms with advantages over the use of in vivo animal models. However, in vitro platforms currently available either fail to recapitulate the in vivo microenvironment and/or the cell compartmentalization of intestinal structures or are difficult to assay or image, particularly in high throughput assays, due to their three-dimensional nature.

Accordingly, there is an ongoing need for new methods of producing tissue constructs of interest, particularly those that that can comprise two or more different cell populations, such as intestinal tissues, on a flat surface.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, methods for producing tissue constructs comprising two or more distinct regions, each of which comprises a different cell population or lineage, are provided. Such methods can in some aspects comprise (a)

providing a support substrate comprising two or more physically distinct regions, wherein the two or more physically distinct regions of the support substrate are different from each other, and depositing/positioning one or more cells on the support substrate, wherein the one or more cells settle on or adhere to the support substrate and proliferate on the support substrate. The one or more cells can convert to different cell populations or lineages on the two or more physically distinct regions of the support substrate.

In some aspects, the two or more physically distinct regions of the support substrate comprise different physical properties, and wherein the one or more cells convert to different cell populations or lineages on the two or more physically distinct regions of the support substrate in response to the different physical properties of the two or more physically distinct regions of the support substrate. In some embodiments, the different physical properties are porosity, permeability, stiffness, or combinations thereof. In some embodiments, the one or more cells comprise primary cells, optionally wherein the one or more cells comprise primary epithelial cells.

Such methods can further comprise exposing one or more of the two or more physically distinct regions to one or more stimuli, wherein the one or more stimuli are each selected from the group consisting of a drug, a nutraceutical, a signaling molecule, a toxin, an inflammatory mediator, and a microbe-derived compound. In some embodiments, the disclosed methods can further comprise detecting or determining an effect of the one or more stimuli, optionally wherein the detecting or determining comprises comparing one or more of cell differentiation and cell proliferation after exposure to the one or more stimuli to one or more of cell differentiation and cell proliferation prior to exposure to the one or more stimuli and/or in a comparable tissue construct not exposed to the one or more stimuli.

Disclosed herein are apparatuses for producing tissue constructs comprising two or more distinct regions, the apparatuses comprising a luminal container comprising a bottom wall, at least one sidewall extending upwardly from the bottom wall, and an open top defined by the at least one sidewall, and a cell support substrate on the bottom wall or comprising the bottom wall, wherein the cell support substrate comprises two or more physically distinct regions, wherein the two or more physically distinct regions of the cell support substrate are different from each other, wherein the two or more physically distinct regions of the cell support substrate comprise different physical properties. In some embodiments, the cell support substrate comprises a single layer of material comprising two or more physically distinct regions comprising different physical properties. In some embodiments, the cell support substrate comprises a first layer of material and a second layer of material, wherein the first layer is overlaid on the second layer and wherein the first layer and the second layer have different physical properties, and wherein one of the first layer and the second layer comprises one or more openings extending from one surface of the first layer or second layer to the opposite surface of the first layer or second layer, optionally wherein the one or more openings are microholes. In some embodiments, the first layer comprises a porous material and the second layer comprises a nonporous material, and wherein the second layer comprises the one or more microholes, optionally wherein the second layer is the bottom wall of the luminal container. In some embodiments, the first layer comprises a hydrogel, optionally wherein the first layer comprises collagen.

In some embodiments, the apparatuses further comprise a basal container, wherein the basal container comprises a bottom wall and at least one sidewall extending upwardly from the bottom wall, wherein the bottom wall and the at least one sidewall define a well, and wherein the luminal container is held within the well of the basal container, the bottom wall of the basal container is spaced apart from the bottom wall of the luminal container, and a basal container is defined between the bottom wall of the basal container and the bottom wall of the luminal container and/or between the at least one sidewall of the basal container and the at least one sidewall of the luminal container.

Also provided herein are methods of preparing a two-dimensional, live cell culture model of an intestinal or colonic crypt, such methods comprising providing an apparatus as disclosed herein, and depositing/positioning one or more epithelial cells on the cell support substrate, wherein the one or more cells settle on or adhere to the cell support and proliferate on the cell support substrate or substrate assembly, and wherein the one or more cells convert to different cell populations or lineages on the two or more distinct regions of the support substrate or substrate assembly in response to the different physical properties of the physically distinct regions of the support substrate or substrate assembly. In some embodiments, the apparatus comprises a basal container defined between the bottom wall of the basal container and the bottom wall of the luminal container and/or between the at least one sidewall of the basal container and the at least one sidewall of the luminal container, and wherein the method comprises providing a first growth medium to the basal container and a second growth medium to the luminal container, wherein the first growth medium and the second growth medium can be the same or different. In some embodiments, the first growth medium and the second growth medium are the same for at least a first period of time after the depositing/positioning of the one or more cells. In some embodiments, the first and second growth mediums comprise growth factors to support stem cell growth.

In some embodiments, replacing the first or second growth medium after the first period of time with a third growth medium, wherein the third growth medium is different than the first and second growth mediums, optionally wherein the third growth medium is free of growth factors to support stem cell growth, In some embodiments, the third growth medium comprises one or more stimuli, wherein each stimuli is selected from a drug, a nutraceutical, a signaling molecule, a toxin, an inflammatory mediator, and a microbe-derived compound. In some embodiments, one or both of the first and second growth medium comprises one or more stimuli, wherein each stimuli is selected from a drug, a nutraceutical, a signaling molecule, a toxin, an inflammatory mediator, and a microbe-derived compound. In some embodiments, the method further comprises detecting or determining an effect of the one or more stimuli on one or more of the different cell populations or lineages, optionally wherein the detecting or determining comprises comparing one or more of cell differentiation and cell proliferation in the one or more different cell population or lineages after exposure to the one or more stimuli to one or more of cell differentiation and cell proliferation in the one or more different cell population or lineages prior to exposure to the one or more stimuli and/or to one or more of cell differentiation and cell proliferation in one or more cell population or lineage of a comparable cell culture model not exposed to the one or more stimuli.

The foregoing and other objects and aspects of the present disclosure are explained in detail in the specification set forth below.

Embodiments of the presently disclosed subject matter having been stated hereinabove, and which is achieved in whole or in part by the presently disclosed subject matter, other embodiments will become evident as the description proceeds when taken in combination with the accompanying Examples as best described hereinbelow.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, can be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings.

DETAILED DESCRIPTION

Figure 1A:
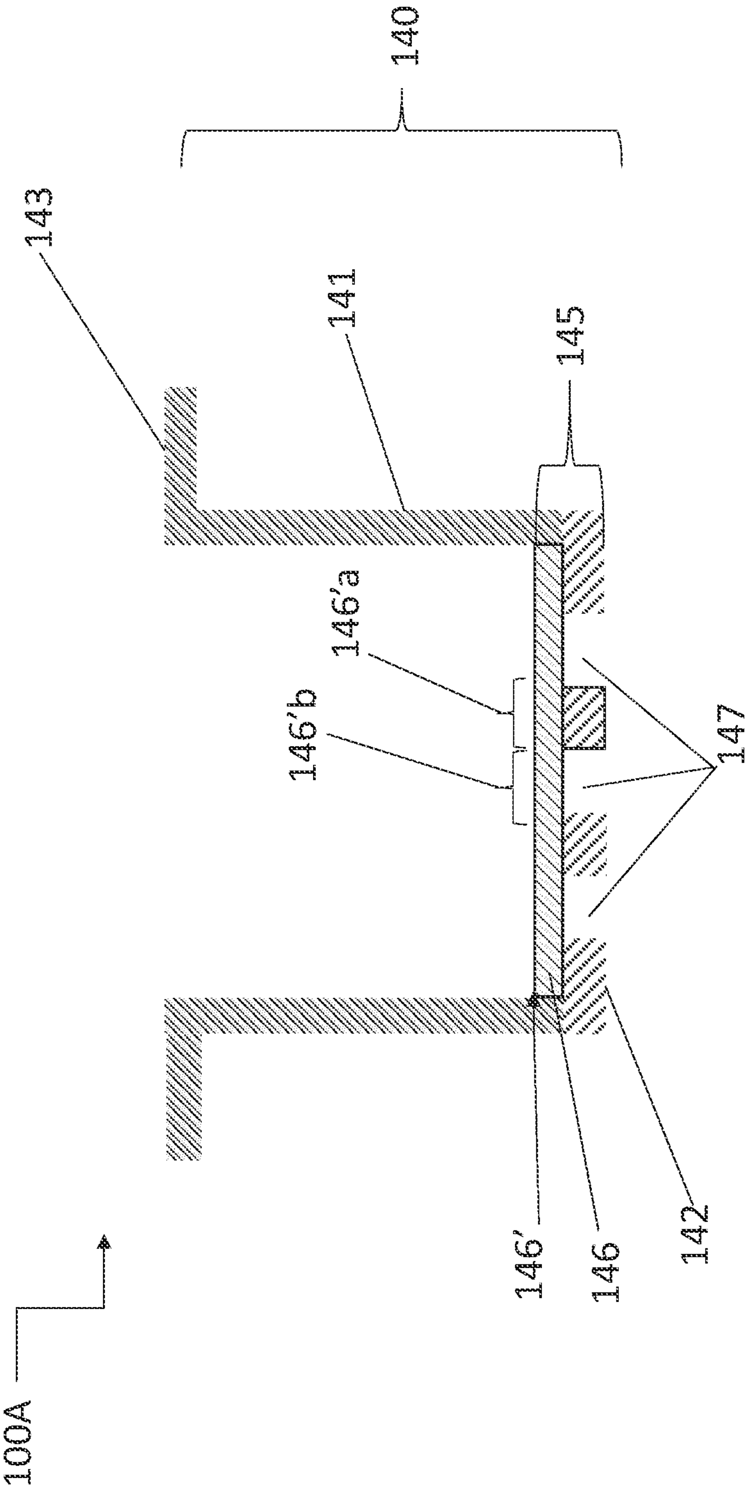
FIG. 1A is a schematic drawing showing a cross-sectional side view of an exemplary apparatus of the presently disclosed subject matter comprising a cell support substrate and a luminal container. The cell support substrate comprises a layer of a porous material overlaid onto a layer of a nonporous material comprising with micropatterned holes. The cell support substrate comprises two different regions, one where the porous material is overlaid on the nonporous material and a second where the porous material is located over a hole in the nonporous material.

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein; rather, these embodiments are provided so that this disclosure will satisfy applicable legal requirements.

I. Definitions

The terminology used herein is for the purpose of describing particular embodiments only and is not intended to be limiting of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Following long-standing patent law convention, the terms "a", "an", and "the" refer to "one or more" when used in this application, including the claims. Thus, for example, reference to "a unit cell" includes a plurality of such unit cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of a composition, mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Numerical ranges recited herein by endpoints include all numbers and fractions subsumed within that range (e.g. 1 to 5 includes 1, 1.5, 2, 2.75, 3, 3.90, 4, 4.24, and 5). Similarly, numerical ranges recited herein by endpoints include sub-ranges subsumed within that range (e.g. 1 to 5 includes 1-1.5, 1.5-2, 2-2.75, 2.75-3, 3-3.90, 3.90-4, 4-4.24, 4.24-5, 2-5, 3-5, 1-4, and 2-4).

It will be understood that when an element is referred to as being "on," "attached" to, "connected" to, "coupled" with, "contacting," etc., another element, it can be directly on, attached to, connected to, coupled with and/or contacting the other element or intervening elements can also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature can have portions that overlap or underlie the adjacent feature.

Spatially relative terms, such as "under," "below," "lower," "over," "upper" and the like, can be used herein for ease of description to describe an element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device can otherwise be oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only, unless specifically indicated otherwise.

As used herein, the terms "example," "exemplary," and grammatical variations thereof are intended to refer to non-limiting examples and/or variant embodiments discussed herein, and are not intended to indicate preference for one or more embodiments discussed herein compared to one or more other embodiments.

As used herein, the terms "increase," "increasing," "increased," "enhance," "enhanced," "enhancing," and "enhancement" (and grammatical variations thereof) describe an elevation of at least about 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount.

The term "cell medium", as used herein, refers to a liquid or gel comprising components to support the growth of cells (e.g., a suitable energy source and compounds to regulate cell cycle). In some embodiments, the cell medium can comprise a minimum essential type of medium, such as Dulbecco's Modified Eagle's Medium, Ham's F12, Eagle's Medium, RPMI, AR8, etc., to which other ingredients can optionally be added. The term does not exclude media which have been prepared or are intended for specific uses, but which upon modification can be used for other cell types, etc.

A "compound," as used herein, refers to any type of substance or agent that is commonly considered a drug, therapeutic, pharmaceutical, small molecule, or a candidate for use as the same, as well as combinations and mixtures of the above.

The term "drug" as used herein refers to a compound or composition with known biological effects and used as a pharmaceutical agent (e.g., in medical and/or veterinary applications) to treat diseases, disorders, and/or conditions.

The term "test compound" as used herein refers to a compound with suspected or unknown biological effect.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

The term "growth factor" as used herein means a bioactive molecule that promotes the proliferation of a cell or tissue. Growth factors useful in the present disclosure include, but are not limited to, transforming growth factor-alpha (TGF-$\alpha$), transforming growth factor-beta (TGE-$\beta$), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5 s, NGF 7.0 s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor, glial neurotrophic growth factor, stem cell factor (SCF), keratinocyte growth factor (KGF), skeletal growth factor, bone matrix derived growth factors, and bone derived growth factors and mixtures thereof. Some growth factors can also promote differentiation of a cell or tissue. TGF, for example, can promote growth and/or differentiation of a cell or tissue.

The term "ingredient" refers to any compound, whether of chemical or biological origin, that can be used in cell culture media to maintain or promote the proliferation, survival, or differentiation of cells. The terms "nutrient", "supplement", and ingredient" can be used interchangeably and are all meant to refer to such compounds. Typical non-limiting ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

The term “inhibit,” as used herein, refers to the ability of a compound, agent, or method to reduce or impede a described function, level, activity, rate, etc., based on the context in which the term “inhibit” is used. Preferably, inhibition is by at least 10%, more preferably by at least 25%, even more preferably by at least 50%, and most preferably, the function is inhibited by at least 75%. The term “inhibit” is used interchangeably with “reduce” and “block.”

The term “material”, as used herein, refers to synthetic and natural materials, such as matrix components (e.g., synthetic or natural polymers). The term “materials and compounds” as used herein, refers to, inter alia, materials, compounds, cells, peptides, nucleic acids, drugs, matrix components, and imaging agents.

The term “modulate”, as used herein, refers to changing the level of an activity, function, or process. The term “modulate” encompasses both inhibiting and stimulating an activity, function, or process. The term “modulate” is used interchangeably with the term “regulate” herein.

A “sample,” as used herein, refers to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest.

As used herein, “scaffold”, “substrate”, “cell support”, “surface”, “platform”, and “cell support substrate” refer to a supporting framework, such as one for cell or tissue growth, either in vivo or in vitro. The terms can be used interchangeably herein and refer to a structural unit of any size, where said structural unit or substrate has a surface suitable for immobilization of molecular structure or modification of said structure and said substrate is made of a material such as, but not limited to, metal, metal films, glass, fused silica, synthetic polymers, and membranes.

The term “stimulate” as used herein, means to induce or increase an activity or function level such that it is higher relative to a control value. The stimulation can be via direct or indirect mechanisms. In one aspect, the activity or function is stimulated by at least 10% compared to a control value, more preferably by at least 25%, and even more preferably by at least 50%. The term “stimulator” as used herein, refers to any composition, compound or agent, the application of which results in the stimulation of a process or function of interest, including, but not limited to, wound healing, angiogenesis, bone healing, osteoblast production and function, and osteoclast production, differentiation, and activity.

“Tissue”, as used herein, means (1) a group of similar cells united to perform a specific function; (2) a part of an organism consisting of an aggregate of cells having a similar structure and function; and/or (3) a grouping of cells that are similarly characterized by their structure and function, such as muscle or nerve tissue.

As used herein, “positioned above the bottom wall” can include “positioned on the bottom wall.” In some embodiments, the bottom wall can comprise a cell support structure.

A “cell type” as used herein refers to morphologically or phenotypically distinct cell forms within a species.

II. General Considerations

Lineage decision of stem cells is influenced by many factors including biochemical cues (e.g., signaling molecules and metabolites) and the biophysical properties of the tissue (e.g., matrix properties, mechanical forces, etc.). See Terryn et al., F1000Research 2018, 7; Semrau and van Oudenaarden, Annual Review of Cell and Developmental Biology 2015, 31, 317-345; Ito and Ito, Annual Review of Cell and Developmental Biology, 2016, 32, 399-409; Gattazzo et al., Biochminica et Biophysica Acta (BBA); General Subjects, 2014, 1840, 2506-2519; and Li et al., Regnerative Medicine, 2011, 6, 229-240. The intestinal epithelium is one exemplary system where lineage decision is made to maintain proper functions. Intestine epithelium is the outer layer of the intestine that faces and protects the intestine from continuous biochemical, microbial, and mechanical challenges. It consists of different cell types that are originated from intestinal stem cells. In the colon, intestinal stem cells, which are located at the base of crypt, rapidly proliferate, move along the crypt and differentiate into different lineages of cells with distinct functions such as enterocytes, goblet cells, and enteroendocrine cells. The balance among maintaining sternness, proliferation and differentiation of the intestinal epithelium governs the health of the intestine. This balance is regulated by the local microenvironment that includes signaling molecules, microbe-derived compounds, gases, and stiffness. See Wang et al., Cellular and Molecular Gastroenterology and Hepatology, 2018, 5(3), 440-453. For instance, a high concentration of Wnts, the ligands for Wnt/β-catenin signaling, and a low level of the bacterial metabolite butyrate at the base of the crypt can maintain and confine the stem cell population.

Recent studies with in vivo animal models have shown that intestinal homeostasis has broad impacts, beyond the intestine, on healthy and disease states of the host. See Hall et al., Nature Review Genetics, 2017, 18, 690; Young, B M J, 2017, 356, j831; Shreiner et al., Current Opinion in Gastroenterology, 2015, 31, 69: Lynch and Pedersen, New England Journal of Medicine. 2016, 375, 2369-2379; and Tremlett et al., Annals of Neurology, 2017. However, the complexity of the intestinal tissue has impeded the understanding of how intestinal homeostasis is maintained and regulated. Intestine tissue consists of different cells including, in addition to the epithelium, myofibroblasts, endothelial cells, and immune cells. Moreover, the mammalian intestine hosts a microbial cell community that outnumbers the host cells. With animal models, it can be difficult to delineate how these different players in the intestine interact each other and regulate intestinal homeostasis. Further, time and expense are significantly more for in vivo animal study than in vitro study. Accordingly, the development of in vitro model systems that recapitulate key components of the intestine is an attractive alternative to in vivo animal models.

Currently the gold standard for in vitro primary intestinal cell culture is an organoid system. Primary intestinal epithelial stem cells are separated from tissue and embedded in a hydrogel, such as Matrigel. This system has provided progress in gastrointestinal research by enabling primary intestinal cell culture without genetic variations from the donor. Most intestinal epithelial cell types can be produced in relatively enriched populations in organoid systems (see Yin et al., Nature Methods, 2014, 11, 106: Van Es et al., Nature Cell Biology, 2012, 14, 1099; and Basak et al., Cell Stem Cell, 2017, 20, 177-190); and several disease models such as cystic fibrosis (see Dekkers et al., Nature Medicine, 2013, 19, 939) and pathogenic infections (see Finkbeiner et al., MBio, 2012, 3, e00159; Karve et al., PloS one, 2017, 12, e0178966; and Bartfeld, Developmental Biology, 2016, 420, 262-270) have been modeled using organoid systems. However, the enclosed structure of organoid culture can make it difficult to access the luminal side (which is the habitat of the microbiome in the intestine), thus, limiting usability for luminal manipulation or assaying. Also, the three-dimensional structure of organoids imposes challenges in imaging and genetic manipulation.

Two-dimensional culture of intestinal epithelial cells can provide unlimited access to the cells. Primary intestinal epithelial cells have been grown as a monolayer on a collagen hydrogel (see Wang et al., Cellular and Molecular Gastroenterology and Hepatology, 2017, 4, 165-182) or on an extracellular matrix protein coating (collagen I or IV or Matrigel) on commercially available cell culture substrates with porous membranes. See In et al., Cellular and Molecular Gastroenterology and Hepatology, 2016, 2, 48-62; Tong et al., Biomaterials, 2018, 154, 60-73; and Kozuka et al., Stem Cell Reports, 2017, 9, 1976-1990. These two-dimensional systems, which can be interconverted to a three-dimensional (3D) organoid, allow unlimited access to the luminal side of the culture and convenient assaying including transepithelial electric resistance measurement and microscopy. However, in both systems, it is difficult to obtain both intestinal stem or proliferative cells and differentiated cells within one sample in a spatially controlled manner. This is because it is challenging to spatially separate biochemical cues for proliferation and differentiation in the liquid medium. Thus, the cells in 3D organoids and two-dimensional (2D) monolayer cultures become mostly undifferentiated or differentiated depending on the media composition.

Improvement in recapitulating an in vivo microenvironment into a 3D in vitro platform was achieved by culturing primary human and mouse intestinal cells on the 3D collagen scaffolds that have the same microstructure as in vivo tissue under a growth factor gradient across the scaffold. See Wang et al., Biomaterials, 2017, 128, 44-55; Wang et al., ACS Biomaterials Science & Engineering, 2017, 3, 2502-2513; and Wang et al., Cellular and Molecular Gastroenterology and Hepatology, 2018, 5, 113-130. The primary cells in these platforms becomes polarized, responding the growth factor gradient, into a proliferative cell rich zone (base) and a differentiated zone (surface). Also, short chain fatty acids, which are well known bacterial metabolites, were shown to assert significant effects on the proliferation and differentiation of the intestinal epithelial cells in the platform. However, assaying and imaging can be still challenging due to the 3D topology of the microstructures, potentially limiting the usability of the platform.

The presently disclosed subject matter provides, in some embodiments, in vitro cell culture platforms and methods of making and using the same, e.g., to produce planar tissue constructs comprising two or more regions comprising different cell populations, or to determine the effects of different stimuli (e.g., drugs, toxins, nutraceuticals, food-derived compounds, microbe-derived compounds (e.g., microbial metabolites), etc.) on cell growth. As one example, in some embodiments, the cell culture platform is an intestinal cell culture platform that replicates the cell compartmentalization of crypts, but as a monolayer, i.e., as a flattened or two-dimensional crypt with controllable dimensions.

In an exemplary embodiment, the cell culture platform comprises a microdevice comprising an array of openings or holes (e.g., microholes) in an impermeable/nonporous layer which is overlaid with a layer comprising a permeable/porous material. See FIG. 4A. This arrangement gives rise to two physically distinct regions, as the properties of the surface overlaying the openings or holes is different from that of the surface overlaying the impermeable layer. The platform can be constructed such that the "basal" and the "luminal" surfaces of the platform are in contact with different fluid reservoirs/containers, providing the ability to provide different compositions to each reservoir/container, thereby treating select areas of the cell culture grown on the platform with one or more different compounds that another select area of the cell culture.

The presently disclosed subject matter is directed, in some embodiments, to methods that define multiple cell populations on a substantially flat surface. Thus, in some embodiments, the presently disclosed subject matter provides a method for producing planar tissue constructs comprising two or more distinct regions, each of which comprises a different cell population or lineage, the method comprising: (a) providing a support substrate comprising two or more physically distinct regions, wherein the two or more physically distinct regions of the support substrate are different from each other; and (b) depositing/positioning one or more cells on the support substrate wherein the one or more cells settle on or adhere to the support substrate or substrate assembly, and proliferate on the support substrate, wherein the one or more cells convert to different cell populations or lineages on the two or more distinct regions of the support substrate. The support substrate can comprise a substantially flat surface onto which the one or more cells are deposited. In some embodiments, the two or more physically distinct regions are in two physically distinct locations of the support substrate, and for example, one or more different types of cells can be deposited/positioned on the support substrate such that the one or more different cells convert to different cell populations on the surface of the different locations, e.g., in response to exposure to different compounds or other conditions.

In some embodiments, the other conditions can include the different locations of the support substrate having different physical properties. Thus, in some embodiments, the two or more physically distinct regions of the substrate have different physical properties, including, but not limited to porosity, permeability, and/or stiffness. Cells deposited on the support can convert to different cell populations or lineages on the two or more distinct regions of the support substrate in response to the different physical properties of the physically distinct regions of the support substrate. For example, one cell type can be deposited/positioned on the surface of the support substrate and proliferate, converting into one cell population or lineage on one type of physically distinct region of the substrate and into a different cell population or lineage on a second type of physically distinct region.

Accordingly, in some embodiments, the presently disclosed subject matter provides methods for creating two or multiple (more than two; e.g., 3, 4, 5, 6, 7, 8, 9, 10, or more) regions of different cell populations or lineages on two-dimensional cell supports that comprises two or multiple (more than two; e.g., 3, 4, 5, 6, 7, 8, 9, 10, or more) material properties in distinct regions of the cell support. In some embodiments, the distinct regions of a cell support can include, but are not limited to, different permeability, porosity and/or stiffness.

Exemplary ranges of physical properties for a region of a support substrate of the presently disclosed subject matter are provided in Table 1, below.

TABLE 1

| Ranges for physical properties for regions within a support substrate. | |
|---|---|
| Material properties | Region |
| Porosity | 0%-100% |
| Permeability coefficient | 0-$10^2$ cm/s |
| Stiffness | $1 \times 10^0$ Pa-$1 \times 10^{12}$ Pa |

Further to the ranges of physical properties shown in Table 1, in some embodiments porosity of a region within a support substrate can range from about 0% to about 10%, or about 0% to about 20%, or about 0% to about 30%, or about 0% to about 40%, or about 0% to about 50%, or about 0% to about 75%, or about 0% to about 90%, or about 5% to about 90%, or about 10% to about 80%, or about 20% to about 70%, or about 30% to about 60%, or about 5% to about 100%, or about 10% to about 100%, or about 20% to about 100%, or about 30% to about 100%, or about 40% to about 100%, or about 50% to about 100%, or about 75% to about 100%.

Further to the ranges of physical properties shown in Table 1, in some embodiments permeability coefficient of a region within a support substrate can range from about 0 cm/s to about 100 cm/s (i.e., $10^2$ cm/s), about 0 cm/s to about 50 cm/s, about 0 cm/s to about 25 cm/s, about 0 cm/s to about 10 cm/s, about 10 cm/s to about 100 cm/s, about 20 cm/s to about 100 cm/s, about 30 cm/s to about 100 cm/s, about 40 cm/s to about 100 cm/s, about 50 cm/s to about 100 cm/s, or about 75 cm/s to about 100 cm/s.

Further to the ranges of physical properties shown in Table 1, in some embodiments stiffness of a region within a support substrate can range from about $1\times10^0$ Pa to about $1\times10^{12}$ Pa, about $1\times10^0$ Pa to about $1\times10^{11}$ Pa, about $1\times10^0$ Pa to about $1\times10^{10}$ Pa, about $1\times^0$ Pa to about $1\times10^9$ Pa, about $1\times10^0$ Pa to about $1\times10^8$ Pa, about $1\times10^0$ Pa to about $1\times10^7$ Pa, about $1\times10^0$ Pa to about $1\times10^6$ Pa, about $1\times10^0$ Pa to about $1\times10^5$ Pa, about $1\times10^0$ Pa to about $1\times10^4$ Pa, about $1\times10^0$ Pa to about $1\times10^3$ Pa, about $1\times10^0$ Pa to about $1\times10^2$ Pa, about $1\times10^1$Pa to about $1\times10^{12}$ Pa, about $1\times10^2$Pa to about $1\times10^{12}$ Pa, about $1\times10^3$ Pa to about $1\times10^{12}$ Pa, about $1\times10^4$ Pa to about $1\times10^{12}$ Pa, about $1\times10^5$ Pa to about $1\times10^{12}$ Pa, about $1\times10^6$ Pa to about $1\times10^{12}$ Pa, about $1\times10^7$Pa to about $1\times10^{12}$ Pa, about $1\times10^8$ Pa to about $1\times10^{12}$ Pa, about $1\times10^9$ Pa to about $1\times10^{\prime 2}$ Pa, about $1\times10^{10}$Pa to about $1\times10^{12}$ Pa, or about $1\times10^{11}$ Pa to about $1\times10^{12}$ Pa.

For the purpose of the presently disclosed subject matter, the difference between distinct regions within a support substrate for any physical property can be about 0.1% or more, or about 0.1% to about 100%, or about 1% to about 90%, or about 1% to about 50%.

Multiple regions of different cell populations or lineages can be obtained by the cellular response to the material properties of the cell support, to different accessibility to a stimulus through the materials in the cell support, or by the combined effects of those two factors. For instance, in some embodiments, multiple regions of different cell populations or lineages can be obtained from culture of a single cell population due to the presence of differences in a physical property (e.g., stiffness) in different regions on the cell support and to differences in access to a nutrient or growth factor in different regions on the cell support In some embodiments, a cell support substrate with two or more material properties can be fabricated by layering two or more materials. In some embodiments, each layer has a thickness of about 1 millimeter or less, about 500 micrometers (μm) or less, about 250 μm or less, about 100 μm or less, about 50 μm or less, of about 25 μm less. In some embodiments, one or more micropatterned film can be implemented to create patterns of material properties in the cell support.

In some embodiments, the presently disclosed subject matter can be used to generate tissue mimics with distinct zones of different types of cells, thereby allowing the study of responses of different cells to, for example, signaling molecules, metabolites, cytokines, drugs or test compounds, microbes and gas within one sample. The presently disclosed subject matter also allows exposure of a controlled area of an initially homogenous cell population to any type of stimuli in order to achieve heterogeneous cell populations, such as, for example, proliferative cells vs. differentiated cells or apoptotic cells vs. viable cells in one flat surface. The 2D configuration of the presently disclosed substrates can be easily adapted to conventional cell culture vessels or microfluidic devices and can be easily scaled up for high throughput screening.

The cell support substrates of the presently disclosed subject matter can he assembled, for example, from two materials comprising different porosity/permeability/stiffness. Non-limiting examples of arrangements of two different materials are shown in FIGS. 2A-2F. The two different materials can be assembled in a co-planar configuration (see FIGS. 2A and 2B) or two different materials can be layered and one of the materials can comprise one or more openings or holes (e.g., microholes). See FIGS. 2C-2F. The physically distinct regions of the support thus include areas located over or under an opening or hole and areas not located over or under an opening or hole. The exemplary arrangement in FIG. 2C, has been demonstrated below in the Examples using a dried collagen film as the porous material, and a 1002F epoxy photoresist as the nonporous material. See also FIG. 4A.

In some embodiments, one or more layer of the cell support substrate can comprise openings or holes. In some embodiments, the openings or holes are microholes. As used herein "microholes" refers to holes with a microscale diameter that extend the length of one or more layers of a cell support substrate, e.g., wherein the holes extend the length of one layer of a two-layer cell support substrate, as shown in FIGS. 2C-2F and FIG. 4A, or one or more layer of a multi-layer structure. The microholes can have a diameter between about 1 micrometer and about 500 micrometers or between about 1 micrometer and about 250 micrometers. In some embodiments, the microholes have a diameter between about 10 micrometers and about 100 micrometers (e.g., about 10, 15, 20, 25, 30, 35, 40, 45, 50, 55, 60, 65, 70, 75, 80, 85, 90, 95 or 100 micrometers. In some embodiments, the microholes have a diameter of about 50 micrometers. The cell substrate can comprise a single microhole, or two or multiple microholes. In some embodiments, the microholes can be arranged in a regular pattern, e.g., a line, a circle, a triangle, etc. In some embodiments, the microholes are arranged as an array comprising two or more rows of microholes, wherein the center of each microhole is located the same distance from the center of each adjacent microhole.

Figure 3:
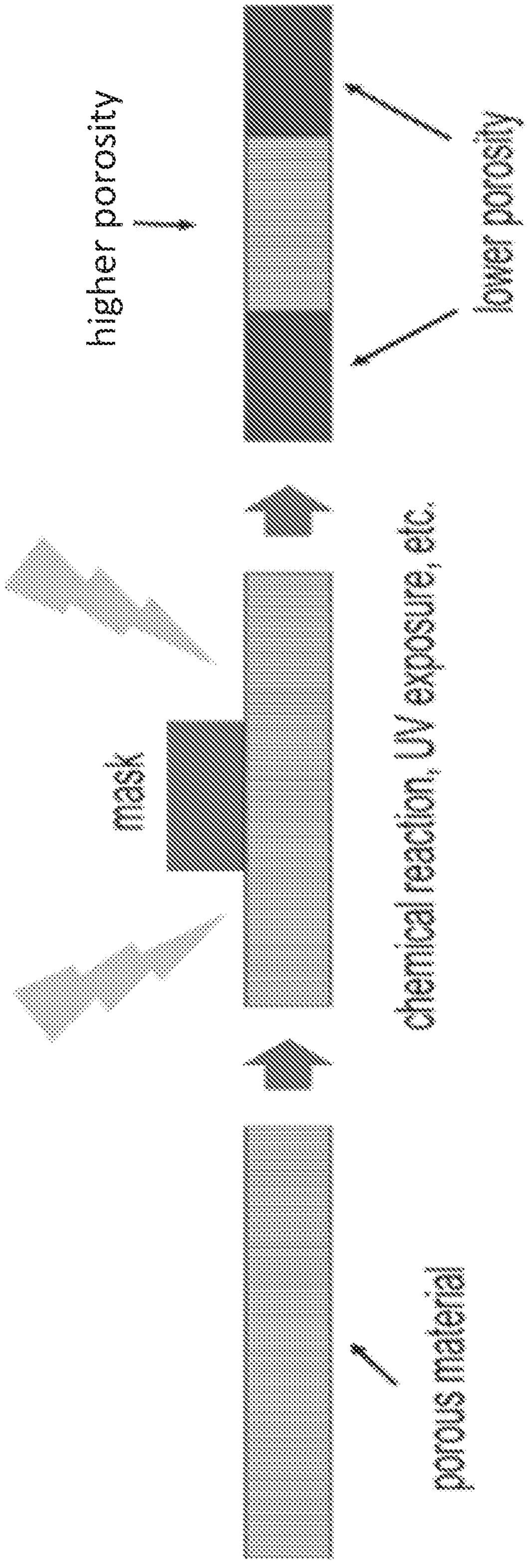
FIG. 3 is a schematic drawing showing an exemplary process for fabricating a cell support substrate with multiple regions of different material properties within one support. A layer of a porous photoresist material is provided (left) and overlaid with a mask that blocks portions of the top surface of the material. The unmasked portions of the material are exposed to a chemical reaction or to light, transforming the unmasked portions of porous material into a material with lower porosity (center). The mask is removed to provide a support with regions of higher and lower porosity (right).

In some embodiments, cell supports with two or multiple material properties can be fabricated within one material (e.g., one layer of one material) by chemical or photochemical reaction and using a masking technique to mask select areas of the surface of the material as shown in FIG. 3. For example, as shown in FIG. 3, a porous material can be overlaid with a masking material to cover one surface of one or more regions of the porous material. The masked material can then be chemically treated or exposed to UV light, resulting in a chemical reaction in the material in the exposed region or regions that changes properties of the material. For example, polymeric material can be made more porous by degrading chemical cross-links or less porous by increasing the level of crosslinking in the material. FIG. 3, for instance, shows a process for preparing a cell support where a layer comprising a porous material can be overlaid with a mask and treated to lower the porosity of the unmasked regions, resulting in a support comprising regions of relatively lower and higher porosity. Similarly, nonporous materials could he masked and the unmasked regions treated to conditions to make the nonporous material porous.

To provide a cell support with more than two different regions having different properties, a support comprising two different materials arranged in the same plane could he overlaid on a third material, optionally wherein the third material comprises an array of microholes. Alternatively, a cell support with two different materials arranged in the same plane could be masked and some of one or both of the regions could be treated (e.g., with light or a chemical) to alter a material property (e.g., porosity).

Exemplary porous material useful with the presently disclosed subject matter, can include, but is not limited to, natural or synthetic hydrogels (e.g. collagen, Matrigel, gelatin, agarose, chitosan, alginate, polyethylene glycol, polyacrylamide), dried hydrogel followed by salt leaching (e.g. collagen hydrogel is dried and the salts are leach out to create pores), plastic track etch membrane (e.g. polycarbonate, polyester), membrane filters (polytetrafluoroethylene, cellulose, polyethersulfone), micromolded meshes (e.g. polydimethylsiloxane, epoxy photoresist. Methods to change the porosity/permeability can include, but are not limited to, adjusting the concentration of solid material, crosslinking density, and/or fabrication design, and the like.

Exemplary nonporous material useful with the presently disclosed subject matter, can include, but is not limited to, 1002F epoxy photoresist, cyclic olefin polymer (e.g. sold under the tradename ZEONOR® (Zeon Corporation, Tokyo, Japan)), polycarbonate, acrylate polymers (e.g. poly(methyl methacrylate)), polystyrene, polyethylene, polypropylene, polyvinyl chloride, cellulose, acrylonitrile butadiene styrene (ABS) plastic, nylon, acetal resin (e.g. acetal resin sold under the tradename Delrin® (E.I. du Pont de Nemours and Company, Wilmington, Del., United States of America)), polytetrafluoroethylene (e.g. TEFLON™ (The Chemours Co., Wilmington, Del., United States of America)), polyesters (e.g. polyethylene terephthalate, polyethylene naphthalate, polybutylene terephthalate, polytrimethylene terephthalate, polyglycolide, polylactic acid, polycaprolactone, copolyesters sold under the tradename TRITAN™ (Eastman Chemical Company, Kingsport, Tenn., United States of America)), epoxy (e.g. SU-8, 1001F, 1009F), elastomers (e.g. polydimethylsiloxane, elastomers sold under the tradename ECOFLEX™ (Smooth-On Inc., Macungie, Pa., United States of America), glass, ceramics, and/or metals.

The cell support substrate can have a total thickness of between about 1 mm and about 1 μm, e.g., a total thickness of about 500 μm or less, about 250 μm or less, about 100 μm or less, or about 50 μm or less. The top surface of the cell support substrate can comprise a flat surface or (e.g., when microholes are present in the top substrate layer, as in FIGS. 2E and 2F) can comprises one or more indentations of less than about 1 mm but more than 1 μm (e.g., less than about 500 μm, less than about 250 μm, less that about 100 μm, less than about 50 μm, less than about 40 μm, less than about 30 μm, less than 10 μm, or less than about 5 μm. In some embodiments, the top surface of the cell support substrate is flat and any microholes in the substrate are not present in the top layer of the substrate.

Cells useful with the presently disclosed subject matter can be from a eukaryotic cell line and/or can be primary cells. In some embodiments, the cells can be mammalian cells, optionally human cells.

In some embodiments, the one or more cells can be small intestinal epithelial cells, colonic epithelial cells (e.g., mouse and human colonic epithelial cells), gastric epithelial cells, fibroblasts, myofibroblasts, endothelial cells, liver cells, adipocytes, muscle cells, bone cells, nervous cells, immune cells, and/or stem cells (embryonic, induced pluripotent stem cells, mesenchymal stem cells, hematopoietic stem cells). In some embodiments, the one or more cells can be cancerous cells from healthy, inflamed, and/or diseased human or animal. In some embodiments, the one or more cells can be, but are not limited to, a cell from a digestive tract, a reproductive tract, a respiratory tract, an eye, a nose, an ear, a kidney, a brain, a liver, a pancreas, a gall bladder, a lymphatic system, a nerve system, skin, a bone, a tendon, a ligament, cartilage, bone marrow, connective tissue, and/or blood. In some embodiments, the one or more cells can be a biofilm that consists of prokaryotic cells or mixture of prokaryotic cells and eukaryotic cells. In some embodiments, the cells can be cells isolated from a biological sample, e.g., from a particular subject of interest, e.g., human or other animal with a particular disease condition or suspected of having a particular disease condition.

In some embodiments, the one or more cells comprise or consist of epithelial cells. In some embodiments, the one or more cells comprise or consist of primary epithelial cells. In some embodiments, the one or more cells comprise or consist of murine or human primary epithelial cells. In some embodiments, the one or more cells comprise a single type of cells, e.g., primary cells, epithelial cells, primary epithelial cells, etc. that differentiate into at least two cell populations after growth on the cell support.

Following deposition/positioning of the one or more cells, the cells and/or the support substrate can be exposed to one or more culture medium, e.g., to aid in cell survival and/or proliferation. The culture medium can be removed and replaced at regular intervals, e.g., ever few hours or every day. Any suitable culture format can be used, e.g., a patch or a monolayer. The two or more physically distinct regions of the cell support substrate can be exposed to the same culture medium or to different culture mediums. In some embodiments, the two or more physically distinct regions are exposed to different culture mediums. In some embodiments, the two or more physically distinct regions can be exposed to the same culture medium for a first period of time following the cell deposition/positioning (e.g., wherein the first period of time is from the time the cells are deposited on the support to a few hours or to about one or more days after deposition/positioning) and then exposed to different culture mediums for a second period of time (e.g., starting at the end of the first period of time).

In some embodiments, the cell culture medium comprises one or more growth factors. Growth factors useful with the presently disclosed subject matter can be any growth factor that can be used to generate a cell population. In some embodiments, the cell culture medium comprises one or more growth factors suitable for supporting stem cell growth (e.g., Wnt3A, R-spondin3, Noggin, etc.). In some embodiments, cell culture medium can comprise one or more ingredients, such as, but not limited to, protein or peptides (e.g. growth factors (e.g., Wnt3A, R-spondin3 and Noggin), cytokines, hormones, antibodies), metabolites (e.g. amino acids, fatty acids, lipids, nucleotides, saccharides), neurotransmitters (acetylcholine, anandamide, histamine and other trace amines, purines), DNA molecules, RNA molecules (e.g., microRNA, siRNA, shRNA as conjugated with lipids or polymers or as capsulated in viral vectors), drugs, test compounds, toxins, anticancer drugs, antibiotics, antifungal agents, antiviral agents, and/or environmental hazards such as atmospheric particulate matters, and pollutants.

In some embodiments, gas stimuli can be used with the presently disclosed subject matter, the gas stimuli including, but not limited to, oxygen, nitrogen, carbon dioxide, carbon monoxide, hydrogen, methane, hydrogen sulphide, skatole (a by-product of meat digestion), indole (a by-product of meat digestion), methanethiol (a sulfur compound), dimethyl sulfide (a sulfur compound), volatile amines, volatile sulfur compounds (VSC), methyl mercaptan, MM (also known as methanethiol, MT), dimethyl disulfide (DMDS) and dimethyl trisulfide (DMTS), volatile fatty acids, and/or or nitric oxide. In some embodiments, a volatile organic compound (VOC) can be used with the presently disclosed subject matter, including, but not limited to, aliphatic hydrocarbons, ethyl acetate, glycol ethers, and acetone, chlorofluorocarbons, benzene, toluene, methylene chloride, perchloroethylene, methyl tert-butyl ether (MTBE), and/or formaldehyde. Biological stimuli useful with the presently disclosed subject matter include, but are not limited to, immune related cells, blood cells, circulating tumor cells, microorganisms, virus, exosomes, bacterial derived molecules such as lipopolysaccharides (LPS), and/or microbe-associated molecular patterns (MAMPs) and/or their analogs. Gas stimuli can be used, for example, by placing the cell support or one side thereof in a chamber comprising the gas stimuli or by bubbling the gas stimuli into a cell culture medium in contact with cell support.

In some embodiments, the presently disclosed method further comprises exposing one or more of the two or more distinct regions to one or more stimuli of interest, e.g., to determine if the stimuli can modulate (i.e., increase or decrease) cell growth or differentiation. In some embodiments, the one or more stimuli are each selected from the group consisting of a drug, a test compound, a nutraceutical, a signaling molecule, a toxin, an inflammatory mediator, and a microbe-derived compound. For instance, the presently disclosed methods can be used to determine an effect of a stimuli of interest on cell growth by comparing cells grown on a region exposed to the stimuli to cell grown on a region not exposed to the stimuli. Thus, in some embodiments, the method further comprises detecting or determining an effect of the one or more stimuli. In some embodiments, the detecting or determining comprises comparing one or more of cell differentiation and cell proliferation after exposure to the one or more additive to one or more of cell differentiation and cell proliferation prior to exposure to the one or more stimuli and/or in a comparable tissue construct not exposed to the one or more stimuli.

In some embodiments, the presently disclosed subject matter provides a method of preparing a two-dimensional, live cell culture model of an intestinal or colonic crypt, the method comprising providing an apparatus comprising a support substrate comprising two or more physically distinct regions, wherein the two or more physically distinct regions of the support substrate are different from each other (e.g., wherein the distinct regions of the support substrate have different physical properties, depositing/positioning one or more epithelial cells on the cell support substrate, wherein the one or more cells settle on or adhere to the cell support and proliferate on the cell support substrate (e.g., in the presence of a suitable cell medium supplied to the cell support substrate or one or more physically distinct regions, or to portions of one or more physically distinct regions thereof), and wherein the one or more cells convert to different cell populations or lineages on the two or more distinct regions of the support substrate. In some embodiments, the one or more cells convert to different cell populations in response to different physical properties of the physically distinct regions of the support substrate.

In some embodiments, the epithelial cells comprise or consist of primary cells. In some embodiments, the epithelial cells comprise or consist of murine or human epithelial cells. In some embodiments, the epithelial cells comprise or consist of human primary epithelial cells or murine primary epithelial cells. In some embodiments, the epithelial cells are from a biological sample from a subject of interest.

In some embodiments, the apparatus comprises a container (e.g., a luminal container) containing a bottom wall and at least one side wall extending upwardly from the bottom wall and wherein the cell support substrate is on the bottom wall of the container (e.g., the luminal container). Medium placed inside the container can be used to mimic an in vivo microenvironment of interest. In some embodiments, medium placed inside the container can be used to mimic a luminal environment of interest and the container can be referred to as a "luminal container." The top of the container can be open or have a removable cover.

In some embodiments, the apparatus further comprises a second container, e.g., wherein the second container can contain a medium in contact with the bottom side of the cell support substrate and that can be considered as a basal container. The basal container can comprise a bottom wall and at least one side wall extending upwardly from the bottom wall. In some embodiments, the basal container can be cylindrical in shape, but having a larger diameter than the luminal container, such that the luminal container can be inserted into the basal container. Thus, in some embodiments, the basal container can be defined between the bottom wall of the basal container and the bottom wall of the luminal container and/or between the at least one sidewall of the basal container and the at least one sidewall of the luminal container. Medium placed in the basal container can be used to mimic an environment of interest to which the bottom of the cell support is exposed (e.g., a basal environment of interest). As described further hereinbelow, the luminal container can have an arm or flange extending from the luminal container side wall, e.g., at or near the top of the luminal container, so that the luminal container can be inserted into a well comprising a basal container and the arm or flange can help to hold the luminal container in position in the other, larger container, e.g., such that the bottom wall of the luminal container does not contact the bottom wall of the basal container. For example, the arm or flange of the luminal container can rest upon the top of the side wall of the basal container when the luminal container is inserted in the basal container.

In some embodiments, the method comprises providing a first growth medium to the basal container and a second growth medium to the luminal container. The first growth medium and the second growth medium can be the same or different. The first and second growth mediums can be provided directly after the one or more cells are deposited/positioned on the cell support substrate. In some embodiments, the first and second growth mediums can be removed and replaced on a regular basis, e.g., every few hours or every day.

In some embodiments, the first growth medium and the second growth medium are the same for at least a first period of time after the one or more cells are deposited/positioned. In some embodiments, the first period of time is between about one hour and about 2 days (e.g., about 1, 2, 4, 6, 8, 10, 12, 14, 16, 18, 20, 22, 24, 28, 32, 36, 40, 44, or about 48 hours). In some embodiments, the first and second growth medium each comprise growth factors to support stem cell growth (e.g., Wnt-3A, R-spondin, noggin, etc.). In some embodiments, the method comprises replacing the first or second growth medium after the first period of time with a third growth medium, wherein the third growth medium is different than the first and second growth mediums. In some embodiments, the third growth medium is free of growth factors to support stem cell growth. In some embodiments, the third growth medium comprises one or more stimuli of interest (e.g., whose effect or level of effect on epithelial cells is known or unknown). For example, the stimuli of interest can be, but is not limited to, a drug, a nutraceutical, a microbe-derived compound (e.g., a microbial metabolite), a toxin, an inflammatory mediator, or a test compound (e.g., a compound with suspected or unknown biological effect). Additionally or alternatively, in some embodiments, one or both of the first and second growth medium comprises one or more stimuli of interest, e.g., wherein each additive is selected from a drug, a nutraceutical, a signaling molecule, a toxin, an inflammatory mediator, and a microbe-derived compound. In some embodiments, both the first and second growth medium are replaced by a different growth medium (e.g., a third and fourth growth medium, which can be the same or different) after a period of time. The replacement of both medium can be performed at the same time or at different times after the cells have been deposited/positioned.

In some embodiments, one or more stimuli of interest has an unknown effect on epithelial cells and the method further comprises detecting or determining an effect of the one or more stimuli on one or more of the different epithelial cell populations or lineages. In some embodiments, the determining comprises comparing one or more of cell differentiation and cell proliferation in the one or more different cell population or lineages after exposure to the one or more stimuli to cell differentiation and/or cell proliferation in the one or more cell population or lineages prior to exposure to the one or more stimuli. In some embodiments, the determining comprises comparing one or more of cell differentiation and cell proliferation in one or more different cell population or lineage to cell differentiation and/or cell proliferation in one or more cell population or lineage of a comparable cell culture model not exposed to the one or more stimuli. Reagents and methods for assaying cell differentiation and cell proliferation are known in the art. For example, cell proliferation can be assayed cells for incorporation of thymidine analog EdU. Thus, in some embodiments, the presently disclosed planar crypt model can be used to detect or determine a modulatory effect of one or more stimuli on intestinal cells. For instance, the stimuli can increase or stimulate cell growth and/or differentiation or decrease cell viability and/or differentiation.

III. Apparatus

In some embodiments, the present disclosure provides an apparatus useful in a method for producing a tissue construct comprising two or more distinct regions, each of which comprise a different cell population or lineage and/or for producing a two-dimensional, live cell culture model of an intestinal or colonic crypt. In some embodiments, the apparatus comprises: a luminal container comprising a bottom wall, at least one sidewall extending upwardly from the bottom wall, and an open top defined by the at least one sidewall; and a cell support substrate on the bottom wall or comprising the bottom wall, wherein the cell support substrate comprises two or more physically distinct regions, wherein the two or more physically distinct regions of the support substrate are different from each other, wherein the two or more physically distinct regions of the support substrate or substrate assembly comprise different physical properties.

In some embodiments, the cell support substrate can comprise a single layer comprising two or more physically distinct regions comprising different physical properties, e.g., wherein the single layer is the bottom wall of the luminal container. In some embodiments, the cell support substrate comprises two or more layers. In some embodiments, the cell support substrate comprises a first layer and a second layer, wherein the first layer is overlaid on the second layer, wherein the first layer and the second layer have different physical properties, and wherein one of the first and the second layer comprises one or more openings or holes extending from one surface of the layer to the opposite surface of the layer. In some embodiments, one of the first and the second layer comprises one or more openings or microholes (e.g., 1, 2, 3, 4, 5, 6, or more microholes; microholes and openings used interchangeable throughout) extending from one surface of the layer to the opposite surface of the layer. In some embodiments, the second layer is the bottom wall of the luminal container. In some embodiments, one of the first and the second layer comprises an array comprising four or more microholes extending from one surface of the layer to the opposite surface of the layer. In some embodiments, each of the one or more microholes has a diameter of between about 10 micrometers and about 100 micrometers (e.g., about 50 micrometers). In some embodiments, the first layer comprises a porous material and the second layer comprises a nonporous material, and wherein the second layer comprises the one or more microholes.

As described hereinabove, the cell support substrate can have a total thickness of between about 1 mm and about 1 μm, e.g., a total thickness of about 500 μm or less, about 250 μm or less, about 100 μm or less, or about 50 μm or less. Each layer of the cell support substrate can have an individual thickness of between about 1 mm and about 1 μm, e.g., a total thickness of about 500 μm or less, about 250 μm or less, about 100 μm or less, or about 50 μm or less. The layers can have the same or different thicknesses. In some embodiments, each layer is independently between about 2 μm and about 40 μm (e.g., about 2, 4, 6, 8, 10, 12, 14, 16, 18, 20, 22, 24, 26, 28, 30, 32, 34, 36, 38, or about 40 μm).

As described above, exemplary porous material useful with the presently disclosed subject matter, can include, but is not limited to, natural or synthetic hydrogels (e.g. collagen, Matrigel, gelatin, agarose, chitosan, alginate, polyethylene glycol, polyacrylamide), dried hydrogel followed by salt leaching (e.g. collagen hydrogel is dried and the salts are leach out to create pores), plastic track etch membrane (e.g. polycarbonate, polyester), membrane filters (polytetrafluoroethylene, cellulose, polyethersulfone), micromolded meshes (e.g. polydimethylsiloxane, epoxy photoresist. Methods to change the porosity/permeability can include, but are not limited to, adjusting the concentration of solid material, crosslinking density, and/or fabrication design, and the like.

Exemplary nonporous material useful with the presently disclosed subject matter, can include, but is not limited to, 1002F epoxy photoresist, cyclic olefin polymer (e.g. sold under the tradename ZEONOR® (Zeon Corporation, Tokyo, Japan)), polycarbonate, acrylate polymers (e.g. poly(methyl methacrylate)), polystyrene, polyethylene, polypropylene, polyvinyl chloride, cellulose, acrylonitrile butadiene styrene (ABS) plastic, nylon, acetal resin (e.g. acetal resin sold under the tradename Delrin® (E.I. du Pont de Nemours and Company, Wilmington, Del., United States of America)), polytetrafluoroethylene (e.g. TEFLON™ (The Chemours Co., Wilmington, Del., United States of America)), polyesters (e.g. polyethylene terephthalate, polyethylene naphthalate, polybutylene terephthalate, polytrimethylene terephthalate, polyglycolide, polylactic acid, polycaprolactone, copolyesters sold under the tradename TRITAN™ (Eastman Chemical Company, Kingsport, Tenn., United States of America)), epoxy (e.g. SU-8, 1001F, 1009F), elastomers (e.g. polydimethylsiloxane, elastomers sold under the tradename ECOFLEX™ (Smooth-On Inc., Macungie, Pa., United States of America), glass, ceramics, and/or metals.

In some embodiments, one or more layers, e.g., the first layer, comprises a hydrogel. In some embodiments, the hydrogel comprises collagen. In some embodiments, the cell support substrate comprises a first layer overlaid over a second layer and the first layer (i.e., the layer having a top surface upon which one or more cells are to be deposited), comprises a hydrogel (e.g., collagen).

In some embodiments, the apparatus further comprises a basal container, wherein the basal container comprises a bottom wall and at least one sidewall extending upwardly from the bottom wall, wherein the bottom wall and the at least one sidewall define a well, and wherein: the luminal container is held within the well of the basal container; the bottom wall of the basal container is spaced apart from the bottom wall of the luminal container; and a basal container is defined between the bottom wall of the basal container and the bottom wall of the luminal container and/or between the at least one sidewall of the basal container and the at least one sidewall of the luminal container.

In some embodiments, either or both of the luminal and basal containers of the presently disclosed apparatus can be, for example, a petri dish, a cell culture dish, a vessel, or a substrate. In some embodiments, they can be modified versions of commercially available cell culture dishes, vessels, or substrates wherein the commercially available product is modified to include a cell support substrate comprising at least two physically distinct regions.

A cross-sectional view of exemplary apparatus 100A of the presently disclosed subject matter is shown in FIG. 1A. Apparatus 100A comprises a luminal container, generally designated 140. Luminal container 140 can be generally cylindrically shaped, defined by side wall 141, one end of which is attached to bottom wall 142. Luminal container 140 also comprises luminal flange 142, which is attached to or adjacent to the open end of luminal container 140 and extending radially from the top of wall 141. Bottom wall 142 also forms a bottom layer of cell support substrate 145 which further comprises top layer 146 at the bottom of luminal container 140, covering bottom wall 142. Bottom wall/bottom layer 142 comprises a nonporous material traversed by microholes 147. Top layer 146 comprises a porous material, such as a hydrogel (e.g., collagen). Top surface 146' of top layer 146 thus includes surface of two types of physically distinct substrate regions. Region **146'*a* represents a surface of one of the physically distinct regions where cell support substrate 145 includes both top layer 146 and bottom wall/bottom layer 142. Region 146'*b* represents a surface of a second type of physically distinct region where top layer 146 is located above one of microholes 147**.

Figure 1B:
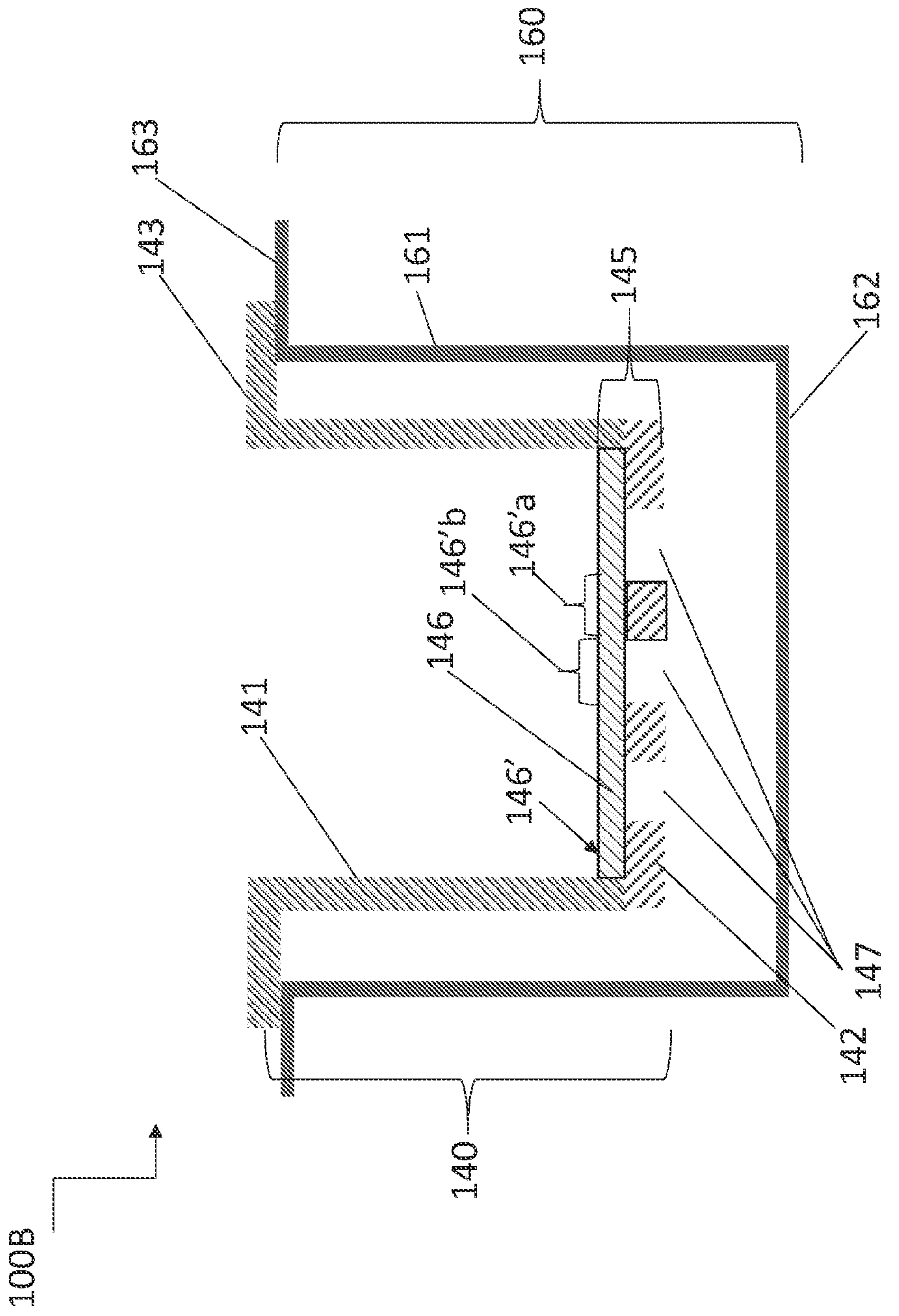
FIG. 1B is a schematic drawing showing a cross-sectional side view of an exemplary apparatus of the presently disclosed subject matter wherein the apparatus of FIG. 1A is inserted in a basal container.

FIG. 1B shows exemplary apparatus 100B in which luminal container 140 of FIG. 1A is inserted into basal container 160. Reference numbers for luminal container 140 are the same as described for FIG. 1A. Basal container 160 can be generally shaped as a cylinder closed at the one end. Basal container 160 is generally defined by side wall 161 attached to bottom wall 162. Bottom wall 142 of luminal container 140 is located above but is not in contact with bottom wall 162 of basal container 160 when luminal container 140 is inserted in basal container 160. As shown in FIG. 1B, basal container 160 also comprises flange 163 which is attached to or adjacent to the open end of luminal container 140, extending radially from the top of wall 141. When inserted in basal container 160, flange 143 of luminal container 140 can rest on flange 163 of basal container 160. Alternatively, flange 163 can be the top wall of an array comprising multiple basal containers.

Figure 1C:
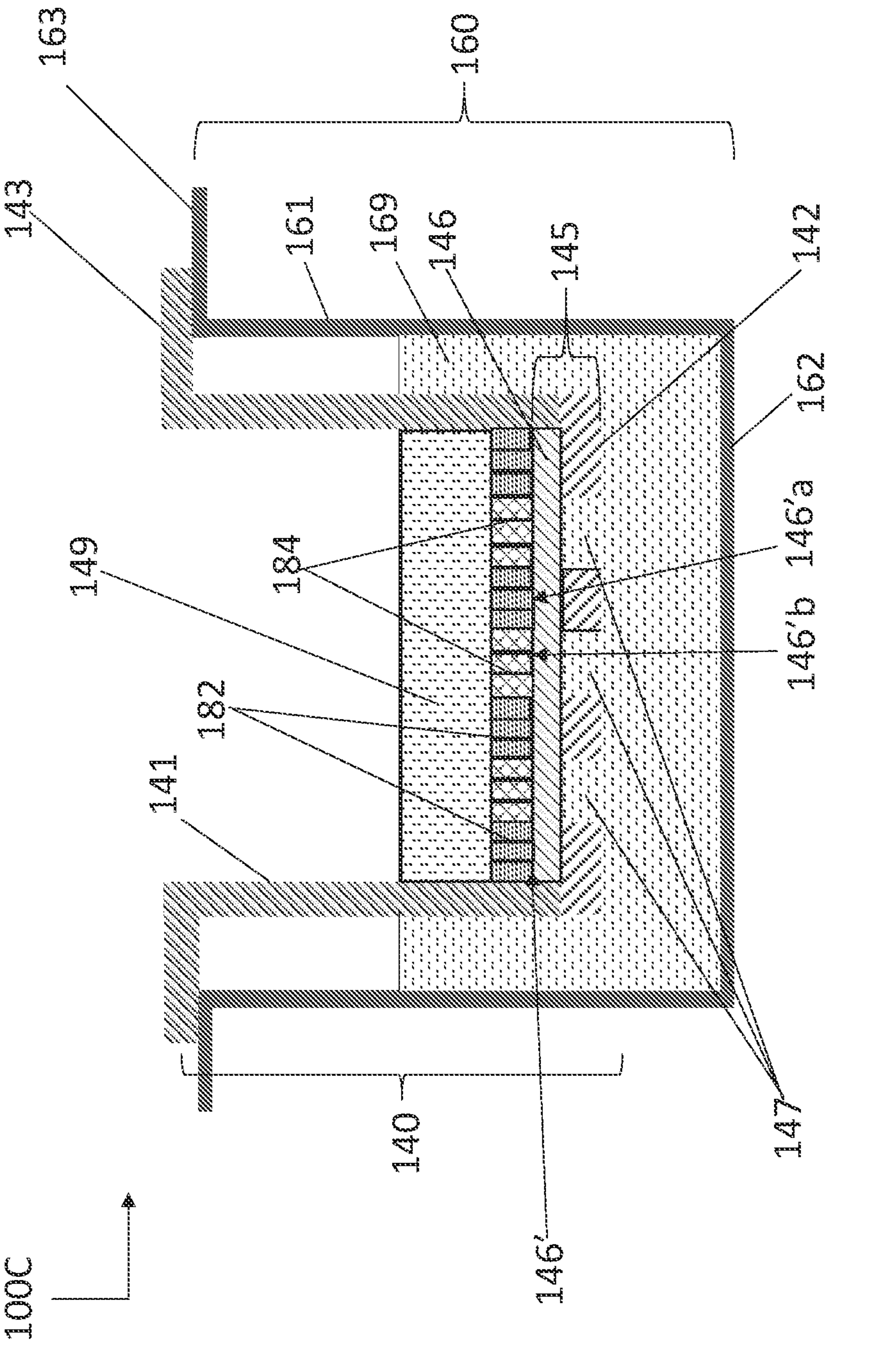
FIG. 1C is a schematic drawing showing a cross-sectional side view of an exemplary apparatus of FIG. 1B after cell deposition and growth, wherein the two different regions of the cell support substrate are exposed to cell medium, optionally different cell medium, and the cells have formed two different populations. A first cell population (Cell 1, e.g., stem cells, drug treated cells, etc.) grows on the top surface of the porous material layer in regions above the holes, while a second cell population (Cell 2; e.g., differentiated cells, non-treated cells, etc.) grows on the top surface of the porous material layer in regions not directly above a hole.
Figure 2B:
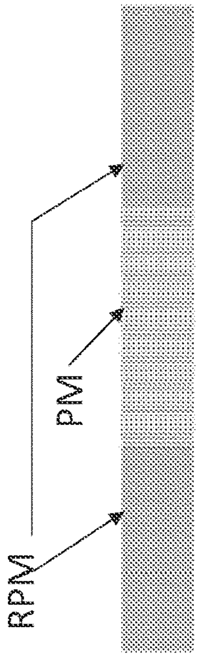
FIG. 2B is a schematic drawing showing a side view of an exemplary cell support substrate of the presently disclosed subject matter comprising regions of two different porosities/permeabilities. The center section comprises a porous support material (PM), while the outer sections comprise a porous material having reduced porosity (RPM) (e.g., compared to the center section PM.
Figure 2D:
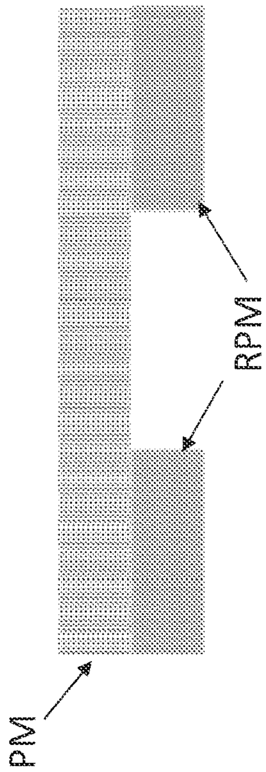
FIG. 2D is a schematic drawing showing a side view of an exemplary cell support substrate of the presently disclosed subject matter comprising regions of two different porosities/permeabilities. A layer of porous material having reduced porosity (RPM) comprising micropatterned holes is overlaid with a layer of porous membrane (PM).
Figure 2F:
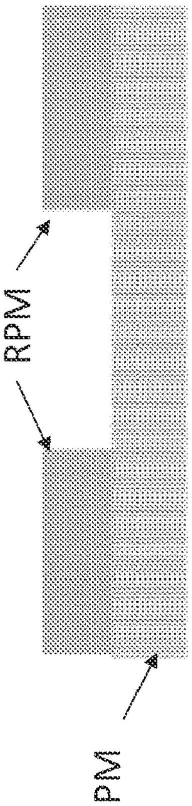
FIG. 2F is a schematic drawing showing a side view of an exemplary cell support substrate of the presently disclosed subject matter comprising regions of two different porosities/permeabilities. A layer of porous material (PM) is overlaid with a layer of porous material having reduced porosity (RPM) comprising micropatterned holes.
Figure 2A:
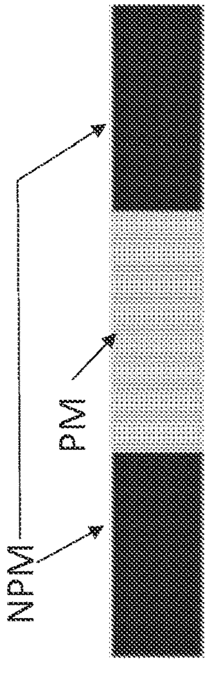
FIG. 2A is a schematic drawing showing a side view of an exemplary cell support substrate of the presently disclosed subject matter comprising regions of two different porosities/permeabilities. The outer sections of the support comprise a non-porous support material (NPM), while the center comprises a porous support material (PM), providing a single layer substrate with materials of different physical properties.
Figure 2C:
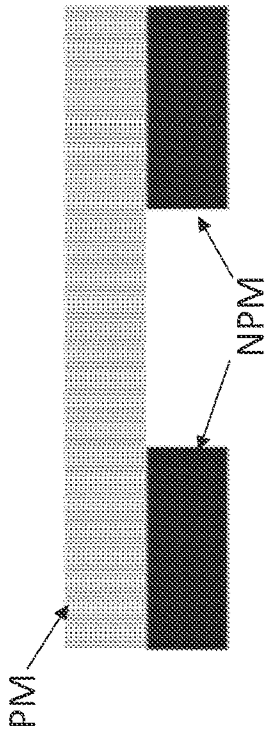
FIG. 2C is a schematic drawing showing a side view of an exemplary cell support substrate of the presently disclosed subject matter comprising regions of two different porosities/permeabilities. A layer of non-porous support material (NPM) comprising micropatterned holes is overlaid with a layer of porous membrane (PM).
Figure 2E:
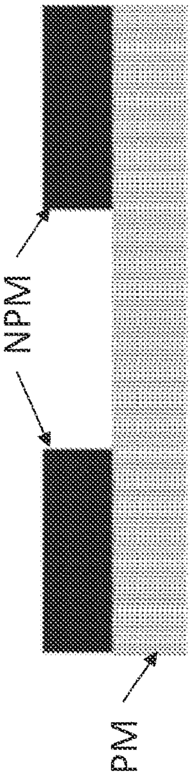
FIG. 2E is a schematic drawing showing a side view of an exemplary cell support substrate of the presently disclosed subject matter comprising regions of two different porosities/permeabilities. A layer of porous material (PM) is overlaid with a layer of non-porous material (NPM) comprising micropatterned holes.

FIG. 1C shows exemplary apparatus 100C, in which apparatus 100B of FIG. 1B has been seeded with cells, which have been allowed to grow. Reference numbers for luminal container 140 and basal container 160 are the same as described for FIGS. 1A and 1B. In FIG. 1C, luminal container 140 is filled with cell medium 149 and basal container 160 is filled with cell medium 169, which is different than cell medium 149. For example, cell medium 149 can be a differentiation medium while medium 169 can be an expansion medium (e.g., containing growth factors to support stem cells). Cell medium 169 of basal container 160 fills microholes 147 of bottom wall/bottom layer 142, allowing it to contact porous top layer 146 of cell support 145. As shown in FIG. 1C, cells seeded on top surface 146' of top layer 146 of cell support 145 form two different cell populations, exemplified by cells 182 and cells 184. Cells 182 are cells that grow on area **146'*a* and covert to a differentiated cell population (e.g., when luminal medium 149 lacks growth factors to support stem cells) or non-treated cell population (e.g., when luminal medium 149 is free of a particular stimuli of interest being screened, such as a particular drug or test compound). Cells 184** are cells that grow on area 146'*b* and can be stem cells (e.g., when basal medium 169 contains growth factors to support stem cells) or treated cells (e.g., when a particular stimuli of interest, such as a particular drug or test compound, is included in basal medium 169).

The apparatuses and methods of the present disclosure are versatile and readily implemented for a plurality of different uses including, for example, but not limited to:

1) in vitro model for physiological studies (transport of macromolecules, ions and water across the cells, enzymatic functions, interaction with bacteria);
2) screening of drugs, biologics, dietary compounds, toxins, mutagens, carcinogens, pathogens, viruses, microbiota, etc.;
3) disease models by using stem and/or primary cells derived from a translational animal models or human;
4) pharmacological, pharmacokinetic and pharmacodynamic models for screening including comprehensive dose-response profiles for drugs, dietary compounds, etc.;
5) in vitro models to study metabolism;

6) in vitro models for wound healing of epithelial tissue to maintain and repair barrier function,
7) in vitro models for study microbe-host interaction;
8) tissue engineering for implantation to repair damaged epithelium;
9) personalized medicine by studies performed on cells from individual patients with specific genetic backgrounds;
10) functional assays such as absorption and transport of water and electrolytes (sodium, chloride, bicarbonate, proton, potassium, calcium), microbe-derived metabolites such as short chain fatty acids, and salvage of unabsorbed nutrients;
11) mucus production, flow, movement and disease related impact on mucus such as in cystic fibrosis;
12) assays of antidiarrheal agents and treatments for constipation, for example, laxatives
13) assays of synbiotics, prebiotics and probiotics;
14) assays of and testing radiopaque and scintigraphic markers and their impact on epithelium;
15) impact of immune cells and their products (antibodies and cytokines) on epithelium;
16) impact of enteric nerve cells and their products on epithelium;
17) impact of muscle cells, their contraction and relaxation and their metabolic products on epithelium;
18) assay of soluble and insoluble fibers and its impact on the epithelium;
19) understanding repair of epitheliums in response to injury of any type;
20) investigation of bacteria leading to pseudomembrane formation, for example, *Clostridium difficile;*
21) screening for biowarfare compounds;
22) studies to understand side effect of drugs and therapeutics such as NSAID treatment, chemotherapy and radiotherapy;
23) studies of the role of the innate and adaptive immune system on epithelial integrity, function and disease (e.g. inflammatory bowel diseases, enteropathies, cancer, etc.);
24) assays for radio-and chemotherapeutics and agents that ameliorate off-target effects;
25) tumor models to mimic hypoxia or oxygen gradient in time and/or space including liquid cancers such as leukemia, or myeloma, and/or solid cancers such as melanoma, carcinoma, sarcoma, lymphoma, germ cell tumor, and/or mixed cancer;
26) assays of antibacterial, antiviral, and/or antifungal agents;
27) studies to understand the effect of bacteriophage on commensal and pathogenic bacteria and their interaction with host cells;
28) in vitro model systems for gram positive and/or gram negative bacterial infection including Gram negative bacteria, gram positive bacteria including, but not limited to, *Acinetobacter baumannii, Actinomyces israelii, Bacillus anthracis, Bacteroides Bartonella henselae, Bordetella pertussis, Borrelia burgdorferi, Borrelia garinii, Borrelia recurrentis, Borrelia recurrentis, Brucela abortus, Brucella canis, Brucella melitensis, Brucella suis, Burkholderia pseudomallei, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium amycolatum, Corynebacterium diphtheriae, Coxiella burnetii, Ehrlichia canis, Ehrlichia chaffeensis, Enterococcus faecalis, Enterococcus faecium, Escherichia coli, Enterotoxigenic Escherichia coli, Enteropathogenic Escherichia coli, Enteroinvasive Escherichia coli, enterohemorrhagic Escherichia coli, Francisella tularensis, Haemophilus influenzae, Helicobacter pylori, Klebsiella pneumoniae, Legionella pneumophila, Leptospira species, Listeria monocytogenes, Mycobacterium leprae, Mycobacterium tuberculosis, Mycoplasma pneumoniae, Neisseria gonorrhoeae, Neisseria meningitidus, Parachlamydia, Pseudomonas aeruginosa, Nocardia asteroides, Rickettsia rickettsii, Salmonella, Shigella, Staphylococcus aureus, Staphylococcus epidermidis, Staphylococcus saprophyticus, Streptococcus agalactiae, Streptococcus pneumoniae Streptococcus pyogenes, Streptococcus viridans, Treponema pallidum, Vibrio cholerae, Vibrio vulnificus,* and/or *Yersinia;*
29) in vitro culture system for understanding infection by virus including double strand DNA viruses, single strand DNA viruses, double strand RNA viruses, positive strand RNA viruses, negative strand RNA viruses, circular single strand RNA viruses, RNA reverse transcribing viruses, DNA reverse transcribing viruses such as *Simplexvirus, Varicellovirus, Cytomegalovirus, Roseolovirus, Lymphocryptovirus, Rhadinovirus, Mastadenovirus, Alphapapillomavirus, Betapapillomavirus, Gammapapillomavirus, Mupapillomavirus, Nupapillomavirus, Polyomavirus, Molluscipoxvirus, Orthopoxvirus, Parapoxvirus, Alphatorquevirus, Betatorquevirus, Gammatorquevirus, Gemycircularviruses, Erythrovirus, Dependovirus, Bocavirus, Coltivirus, Rotavirus, Seadornavirus, Hepevirus, Alphacoronavirus, Betacoronavirus, Torovirus, Mamastrovirus, Norovirus, Sapovirus, Flavivirus, Hepacivirus, Pegivirus, Cardiovirus, Cosavirus, Enterovirus, Hepatovirus, Kobuvirus, Parechovirus, Rosavirus, Salivirus, Alphavirus, Rubivirus, Deltavirus, Lyssavirus, Vesiculovirus, Filoviridae, Ebolavirus, Marburgvirus, Paramyxoviridae, Henipavirus, Morbilivirus, Respirovirus, Rubulavirus, Metapneumovirus, Pneumovirus, Arenavirus, Peribunyaviridae, Orthobunyavirus, Hantavirus, Nairovirus, Phenuivindoe, Phlebovirus, Influenzavirus A Influenzavirus B, Influenzavirus C, Thogotovirus, Gammaretrovirus Deltaretrovirus, Lentivirus, Spumavirus,* and/or *Orthohepadnavirus*);
30) in vitro culture systems for producing vaccine that requires hypoxic condition;
31) in vitro culture system for protozoan infection including *Entamoeba histolytica, Cryptosporidium parvum, Cryptosporidium hominis, Cyclospora cayetanensis,* and/or *Giardia lamblia;*
32) in vitro culture system for unicellular and/or multicellular fungal infection *Aspergillus, Blastomyces, Candida, Coccidioides, Cryptococcus neoformans, Cryptococcus gatti, Histoplasma, Rhizopus, Mucor, Lichtheimia, Pneumocystis jirovecii,* and/or *Sporothrix;*
33) a model for biofilm formation, development, dispersal and/or disruption by antibiofilm agents; and/or
34) a model system or combination of the systems that requires oxygen gradient (in space or time) or hypoxia, such as a hair follicle niche, brain hypoxia post stroke, cyanide poisoning, scar in a dish systems, fibrosis and wound healing, retinopathy, corneal hypoxia and vascularization, periodontitis, upper and lower airway models, bronchiolitis, bronchitis, chronic obstructive pulmonary disease (COPD), pneumonia (bacterial, viral, mycoplasma infection), interstitial lung disease, pulmonary edema, hypoxic pulmonary vasoconstriction models, liver tissue models, liver regeneration, liver fibrosis, viral hepatitis, fatty liver disease, nephropathy, nephritis, bone development and regeneration, cartilage regeneration, bone marrow, fracture healing model, thrombosis, hematopoietic stem cell niche, anemia including sickle cell disease, muscles in exercise models, reproductive tract models, endometriosis, placenta development models including intrauterine hypoxia, embryo development models, ischemia (cardiac, bowel, brain, limb, cutaneous) and ischemia-reperfusion injury models, anesthesia and/or obesity models.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Materials and Methods

Microdevice Fabrication:

An array of 10×10 microholes (each 50 μm in diameter) was fabricated in a thin photoresist film by patterning through holes in a thin photoresist film. The patterned photoresist film was mounted onto a modified TRANSWELL® cassette (Corning, Inc., Coming, N.Y., United States of America) and overlaid with a contiguous but thin collagen layer for cell culture.

More particularly, to create the patterned photoresist film, a layer (20 μm thick) of 1002F50 photoresist (see Pai et al., Analytical Chemistry, 2007, 79, 8774-8780) was spin coated onto a glass slide at 1500 revolutions per minute (rpm) for 30 seconds and then solidified by baking for 30 minutes at 95° C. The photoresist was exposed to ultraviolet light (500 milliJoules (mJ)) through a photomask with an array of open circles (50 μm diameter). The exposed photoresist was then developed in propylene glycol methyl ether acetate (PGMEA) and baked at 95° C. for 12 hours to create an array of microwells of very shallow depth (20 μm). Then the film on the glass slide was soaked for greater than 15 hours to weaken the adhesion of the film to the glass so that the film could be readily transferred to a TRANSWELL® frame (Corning, Inc., Corning, N.Y., United States of America). The membrane on the base of a standard 12-well TRANSWELL® insert array (Corning Inc., Corning, N.Y., United States of America) was completely removed using a tweezer and then the TRANSWELL® frame (Corning, Inc., Corning, N.Y., United States of America) was attached to the photoresist side of the patterned microwell array using double-sided medical tape (3M, Maplewood, Minn., United States of America). At this point, the TRANSWELL® frame (Corning, Inc., Corning, N.Y., United States of America) was rigidly affixed to the 1002F film overlying the glass slide. The slide was detached from the frame-1002F film by slowly lifting the TRANSWELL® frame (Corning, Inc., Corning, N.Y., United States of America) with attached film from the glass slide and then trimming any film extending outside of the frame.

To prepare the final microdevice for mouse colonic cell culture, a thin layer of collagen was formed across the surface of the microwell array. First, the 1002F film within the TRANSWELL® inserts (Corning, Inc,, Corning, N.Y., United States of America) was plasma treated for 5 min to improve its hydrophilicity and aqueous wetting properties. Then the plasma-treated inserts with patterned 1002F film were placed onto a petri dish coated with polydimethylsiloxane (PDMS) where the PDSM was prepared using a silicon elastomer kit sold under the tradename SYLGARD™ 184; Dow Corning, Midland, Mich., United States of America). Neutralized collagen (200 μL of rat tail collagen I in 0.02N acetic acid solution (Corning Inc., Corning, N.Y., United States of America), neutralized with sodium hydroxide, sodium bicarbonate, HEPES and PBS (see Wang et al., Cellular and Molecular Gastroenterology and Hepatology, 2017, 4, 165-182)) was dispensed onto the 1002F film surface within the inserts. The collagen was gelled by incubation for 1 hour at 37° C. The collagen gel was then dried in a 40° C. oven for 16 hours resulting a thin layer of collagen covered with salt crystals and overlaying the photopatterned 1002F film. The thin collagen membrane spanned the gap across the holes on the 1002F film. The collagen-coated 1002F surface in the inserts was gently rinsed with water to remove the salt, sterilized with 70% ethanol and washed with sterile PBS. Just prior to cell culture, 50 μg/mL of rat tail collagen I (Corning) in PBS was added and incubated for at least 1 h at 37° C. with a goal of further enhancing cell adhesion to the collagen film, Simulation and Diffusion Studies:

COMSOL Multiphysics (COMSOL Inc., Burlington, Mass., United States of America) was used to model the diffusion of the growth factors through the collagen covered microholes. The geometry of the microhole array and the luminal/basal reservoirs was incorporated into the model. The diffusion coefficient in the thin collagen layer was assumed to be equivalent to that in the aqueous medium. This assumption is reasonable since the collagen layer in this platform was only 5 μm thick (and the average time through the membrane for even a large growth factor would be under 1 s). To simulate the diffusion of the growth factors (39.7 kilodalton (kDa), Wnt-3A; 40 kDa, R-spondin) through the microhole array, diffusion of fluorescein-dextran (40 kDa) was used. Fluorescein-dextran (Sigma, St. Louis, Mo., United States of America) was dissolved in PBS and placed in the basal reservoir (1.5 mL, 200 Fig/mL) of the microdevice while the luminal reservoir contained PBS (0.5 mL) without the fluorescent dextran. Samples (50 μL) from the basal and luminal reservoirs were collected every 24 hours. The fluorescence intensities of the samples were measured to estimate the concentration of the fluorescent dextran in each reservoir. The measured concentrations were compared to the simulated values in the microdevice using the previously reported diffusivity of 40 kDa fluorescein-dextran, i.e., $7.4\times10^{-11}$ $m^2/s$. See Ahmad et al., RSC Advances, 2015, 5, 74881-74891, Since the experimental data and the simulated value of the fluorescent dextran diffused through the collagen in the microdevice were similar, the same diffusion coefficient was used to simulate the diffusion of the growth factors in the microdevice.

Cell Culture and Immunofluorescence Staining:

Crypts from male and female murine intestines were isolated in buffer (2.0 mM EDTA and 0.5 mM DTT) as described previously. See Wang et al., Cellular and Molecular Gastroenterology and Hepatology, 2017, 4, 165-182. All cells used had undergone fewer than 5 sub-cultures to insure chromosomal integrity. Mouse intestinal cells were cultured as a monolayer on a flat surface of neutralized collagen gel (1 mL placed into a 6-well plate) under expansion medium (EM). EM possesses Wnt3A, R-spondin3 and Noggin to support stem cells within the culture. The composition of EM is further described below in Table 2. The chemicals used in the EM were purchased from the following sources: Advanced DMEM/F12, GlutaMAX, and HEPES from Thermo Fischer Scientific (Waltham, Mass., United States of America); Murin EGF from PeproTech US (Rocky Hill, N.J., United States of America), A83-01 from Sigma Aldrich (St. Louis, Mo., United States of America); N-acetyl cysteine from MP Bio (MP Biomedical, Santa Ana. Calif., United States of America), Rock inhibitor (Y-27632, from ApexBio Technology, LLC. Houston, Tex., United States of America), and an antimicrobial agent sold under the tradename PRIMOCIN™ from InvivoGen (San Diego, Calif., United States of America).

EM was replaced with fresh EM every 2 days. The cells were sub-cultured every 3-5 days by degrading collagen with collagenase and dissociating the cells with 0.5 mM EDTA into clumps of cells. The monolayers were not fully dissociated into single cells, since this results in a high stern cell mortality rate. When placing cells onto the surface of the microdevice, the cell suspension was diluted 1 to 2 in EM and overlaid onto the microdevice surface. The cells were cultured for 2 days with EM placed into the luminal and basal reservoirs of the Transwell cassette. On day 2, the luminal and basal media were changed as described in Table 3, below, and the cells incubated for a day. On day 3, the luminal and basal media were replaced with fresh media (identical to that from day 2 replacement) and the cells incubated for another day. In some experiments, the medium in the luminal compartment was replaced differentiation medium (DM, see Table 2) which is similar to EM but lacking in key growth factors required to support intestinal stem cells. For experiments with short chain fatty acids, each short chain fatty acid was added in the luminal medium at the concentration of 24 mM for acetate, 6 mM for propionate and 1 mM for butyrate.

TABLE 2

Composition of expansion and differentiation media.

| Component | Expansion Media (EM) Concentration | Differentiation Media (DM) Concentration |
|---|---|---|
| Advanced DMEM/F12 | 50% (v/v) | 50% (v/v) |
| WRN | 50% (v/v) | — |
| FBS | — | 10% (v/v) |
| GlutaMAX | 1X | 1X |
| HEPES | 10 mM | 10 mM |
| Murine EGF | 50 ng/mL | 50 ng/mL |
| A83-01 | 500 nM | 500 nM |
| N-Acetyl cysteine | 1 mM | 1 mM |
| Y-27632 | 10 μM | — |
| Antimicrobial agent | 50 μg/mL | 50 μg/mL |

TABLE 3

Exemplary Culture Conditions.

| Name | First 2 days | Last 2 days |
|---|---|---|
| EM/EM | EM in the luminal/ EM in the basal | EM in the luminal/ EM in the basal |
| DM/EM | EM in the luminal/ EM in the basal | DM in the luminal/ EM in the basal |

TABLE 3-continued

Exemplary Culture Conditions.

| Name | First 2 days | Last 2 days |
|---|---|---|
| DM/DM | EM in the luminal/ EM in the basal | DM in the luminal/ DM in the basal |

EM: expansion medium with the growth factors (Wnt-3 A, R-spondin, Noggin)
DM: differentiation medium without the growth factors Cells in the S phase of the cell cycle were incubated with a pulse of 5-ethynyl-2'-deoxyuridine (EdU) pulse following the manufacturers' protocols (Click-iT EdU Alexa Fluor 647 Imaging kit, C10340, Thermo Fisher Scientific, Waltham, Mass., United States of America). EdU is a nucleotide analog incorporated into DNA as it is replicated in S phase. In brief, EdU (10 μM) was added to the luminal and basal media and the cells were incubated for 3 h at 37° C. The cells then were washed with PBS and fixed with 4% paraformaldehyde in PBS for 15 min and permeabilized with 0.5% Triton-X for 20 min at 25° C. EdU incorporated into cellular DNA was visualized by reaction with Alexa 647 via click chemistry following the manufacturer's protocol (Click-iT EdU Alexa Fluor 647 Imaging kit, C10340, Thermo Fisher Scientific, Waltham, Mass., United States of America).

For pulse-chase experiments with EdU, cells were grown in EM for 2 days. On day 2, the luminal and basal media were removed and DM was then added to the luminal compartment while EM was added to the basal compartment, and the cells were incubated for a day. The media was replaced with fresh media (identical to that from day 2 replacement) and the cells incubated for another day. On day 4, EdU was added to the luminal and basal media and the cells incubated for 3 h as described above. The luminal and basal media then were replaced with fresh DM and EM, respectively and the cells incubated for 2 more days with media exchanges every day.

Cell monolayers were assayed for alkaline phosphatase (ALP) activity on day 4 of culture by incubation with ALP substrate mixture (Vector Red AP substrate kit, SK-5100, Vector Laboratories Inc., Burlingame, Calif., United States of America) in Tris buffer (pH 8.4) for 30 min at 37° C. Then cells were washed with PBS, fixed and permeabilized as described above. To label cell DNA, Hoechst 33342 (2 μg/mL, B2261, Sigma Aldrich, St. Louis, Mo., United States of America) was incubated with cells (1 h, 25° C.).

For immunofluorescence staining, primary antibodies against E-cadherin (1:200, 20874-1-AP, ProteinTech, Rosemont, Ill., United States of America), β-catenin (1:200, sc-7963, Santa Cruz Biotechnology Inc., Dallas, Tex., United States of America), mucin 2 (1:200, sc-15334, Santa Cruz Biotechnology Inc., Dallas, Tex., United States of America), and chromogrannin A (1:1500, ab 15160, Abcam, Cambridge, United Kingdom) and Alexa 488-conjugated goat anti-rabbit antibody (1:500, A11008, Life Technologies, Carlsbad, Calif., United States of America, used for E-cadherin, chromogrannin A and mucin 2), or Alexa 647-conjugated donkey anti-mouse antibody (1:500, 715-605-150, Jackson ImmunoResearch, West Grove, Pa., United States of America, for β-catenin) were used. The cells were grown on the microdevices in EM for 2 days and then further cultured as described below. On day 4, the cells were fixed with 4% paraformaldehyde in PBS for 15 min, and permeabilized with 0.5% Triton-X for 20 min at 25° C. To minimize nonspecific binding of antibodies, the cells were blocked with 3% BSA in PBS at ° C. for 1 h. Then each primary antibody that was diluted in 3% BSA in PBS with the dilution ratio recommended by the manufacturers as indicated above was added to the cells and incubated for at least 16 h at 4° C. The cells were then washed with 3% BSA in PBS 3 times, incubated with secondary antibody and Hoechst 33342 diluted both at 1:500 ratio with 3% BSA in PBS for 1 h at 25° C. and finally washed with 3% BSA in PBS twice and then in PBS alone.

Cell Imaging:

The TRANSWELL® insert (Corning, Inc., Corning, N.Y., United States of America) with cell layer from the microdevice was placed into a 12-well plate under PBS and imaged using a FLUOVIEW® FV3000® confocal microscope (Olympus Corporation, Tokyo, Japan) confocal microscope (10×, objective, numerical aperture of 0.4). Alexa 647, Vector-Red-ALP, and Hoechst 33342 were excited with a 640, 561, and 405 nm laser, respectively and the fluorescence emission was collected at 650-750 nm, 570-590 nm, and 430-470 nm, respectively. The images were analyzed with the Fiji software package. See Schindelin et al., Nature Methods, 2012, 9, 676. For all experiments, the numbers of sample sizes were estimated using a statistical power analysis based on the data from Wang et al. (Cellular and Molecular Gastroenterology and Hepatology, 2017, 4, 165-182) measuring EdU+ and ALP activities under varying conditions ($\alpha$=0.05, $\beta$=0.85) using G*Power. See Faul et al., Behavior Research Methods, 2007, 39, 175-191. A one-way ANOVA analysis was used for all statistical analyses of data obtained from the fluorescence microscopy images. Scanning electron microscopy (SEM) was performed using a FEI QUANTA™ 200 ESEM microscope (Thermo Fisher Scientific, Waltham, Mass., United States of America). For the SEM imaging, the samples were first fixed with 4% paraformaldehyde, dried with a critical point dryer (PVT-3, Tousitnis Semidri, Rockville, Md., United States of America) and then coated with 10 nm metal by a sputter coater (Cressington 108, Cresington Scientific Instruments, Watford, United Kingdom).

Stiffness Measurements:

The stiffness of the collagen above and in regions adjacent to the microholes in the 1002F film was measured in fluid (1× PBS) using an atomic force microscope (MFP3D, Asylum Research, Morrisville, N.C., United States of America) to collect force vs indentation curves (2 samples, 10 points above and adjacent to the microholes for each sample). The silicon cantilever (0.03 N/m nominal spring constant) with an attached polystyrene bead (4.5 μm in diameter) was purchased from Novascan Technologies, Inc. (Ames, Iowa, United States of America). All calibrations, data collection, and data analysis were performed using the Asylum software. The spring constant of the cantilever was more accurately determined by recording its thermal motion (0.03175 N/m). Force vs indentation curves were recorded by applying 10 nN to the sample, and the sample stiffness (kPa) obtained by fitting 90% of each curve (140 nm average indent) into the Hertz model.

Example 1

Figure 4A:
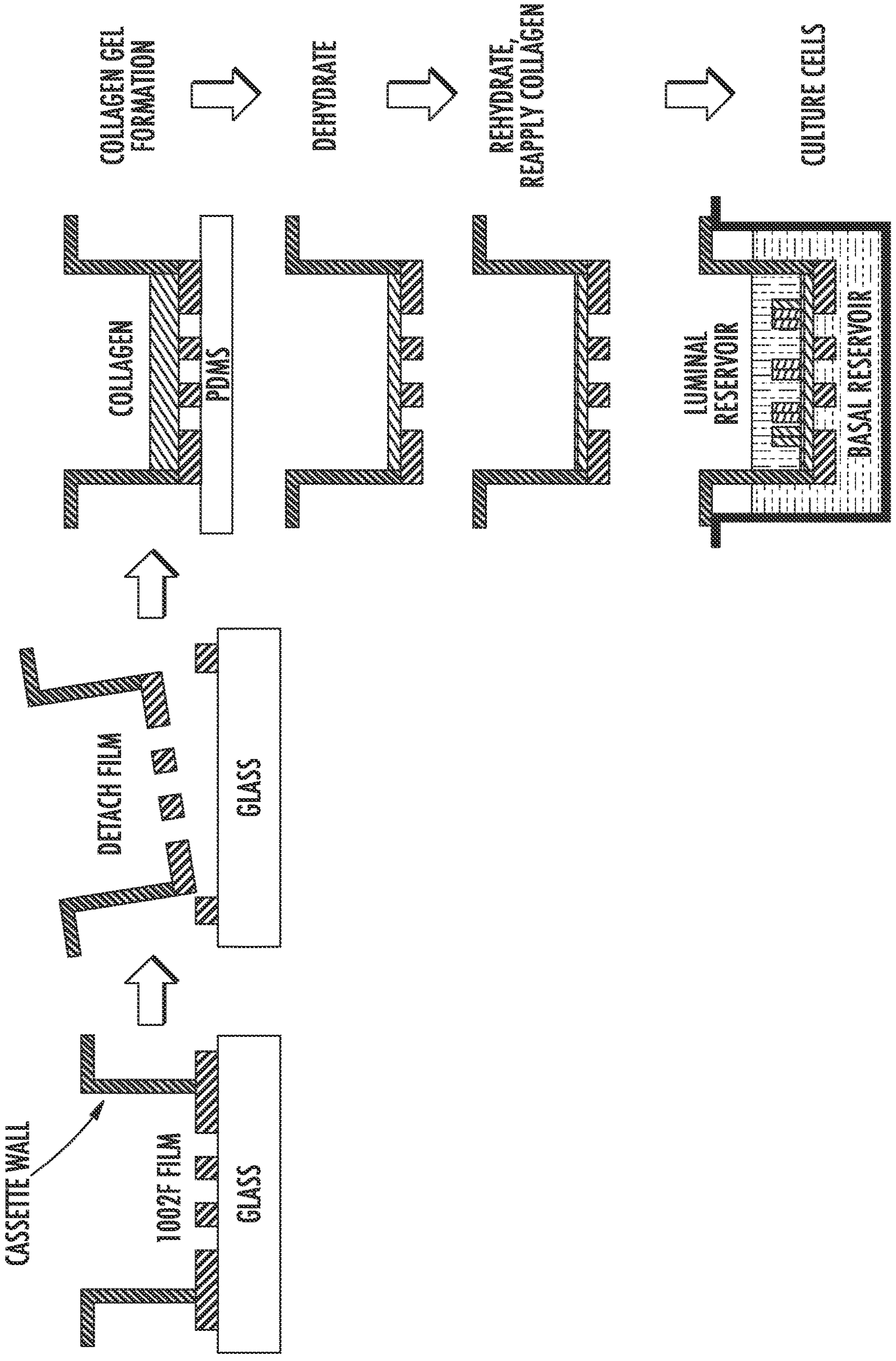
FIG. 4A is a schematic drawing shoring an exemplary process for preparing an apparatus comprising a cell support substrate with multiple regions with different material properties that can be used to grow a planar crypt array. At the top left is shown a side view of a photoresist (1002F) film patterned with an array of microholes on the surface of a glass slide. After being detached from the glass slide (top center), a layer of collagen is overlaid on the photoresist film (top right) and dehydrated, leaving a compacted collagen layer (right, second from top). After rehydration (right, second from bottom) cells are deposited on the top surface of the collagen and media added to basal and luminal containers/reservoirs of the apparatus.
Figure 4B:
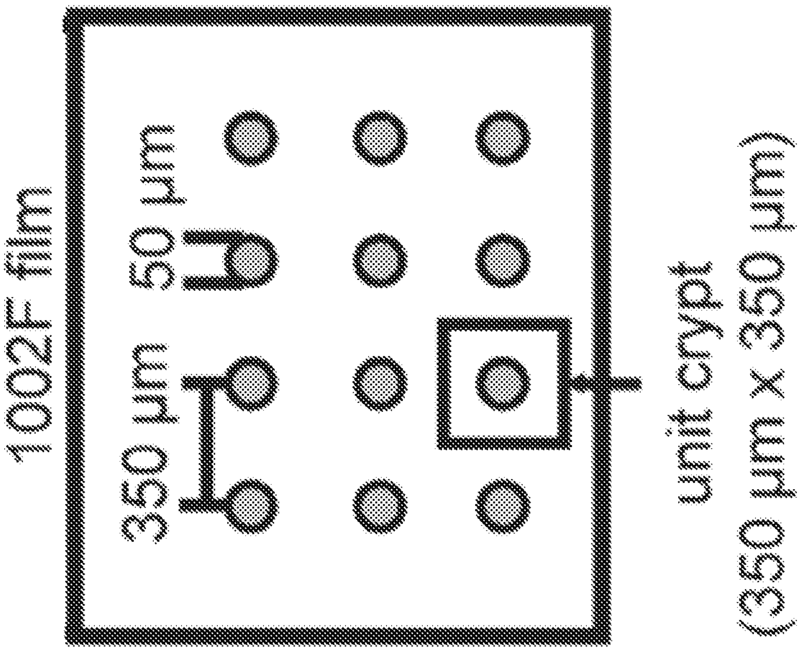
FIG. 4B is a schematic drawing showing a top-view of the photoresist film shown in the top left panel of FIG. 4A, showing the pattern dimensions of the microhole array. A unit crypt is defined as 350 micrometer (μm)×350 μm square with a microhole in the center. Each hole is 50 μm in diameter and the distance from the center of one hole to the center of each adjacent hole is 350 μm.
Figure 4C:
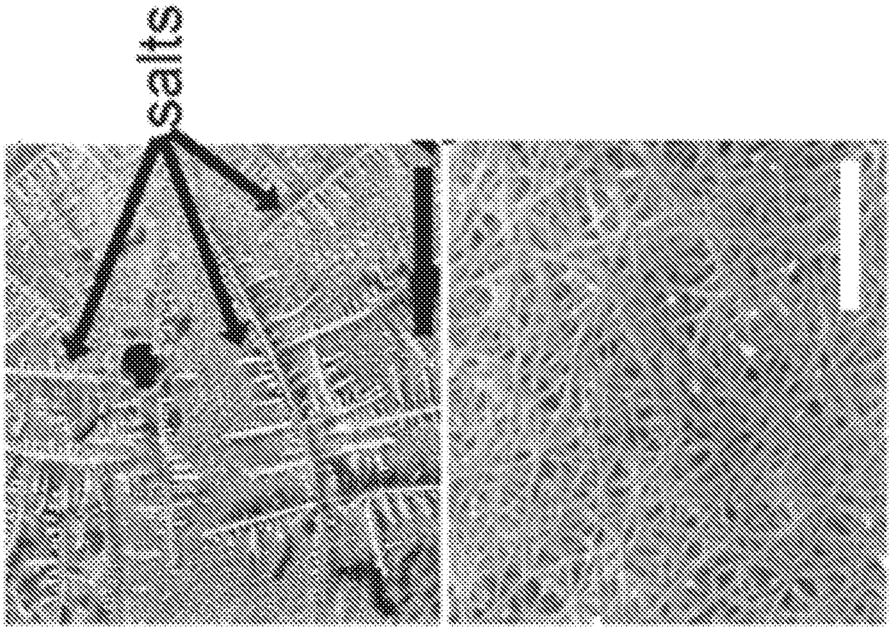
FIG. 4C is a pair of scanning electron microscopy (SEM) images of (top) the top surface of the collagen matrix overlaid on the photoresist film before rehydration (i.e., the film as in FIG. 4A, the panel second from the top on the right) and (bottom) after rehydration (i.e., the film as in FIG. 4A, the panel second from the bottom on the right). Salt crystals can be seen on the surface of the dehydrated collagen matrix, as indicated by the arrows. The black bar (top) represents 200 μm and the white bar (bottom) represents 2 μm.
Figure 4E:
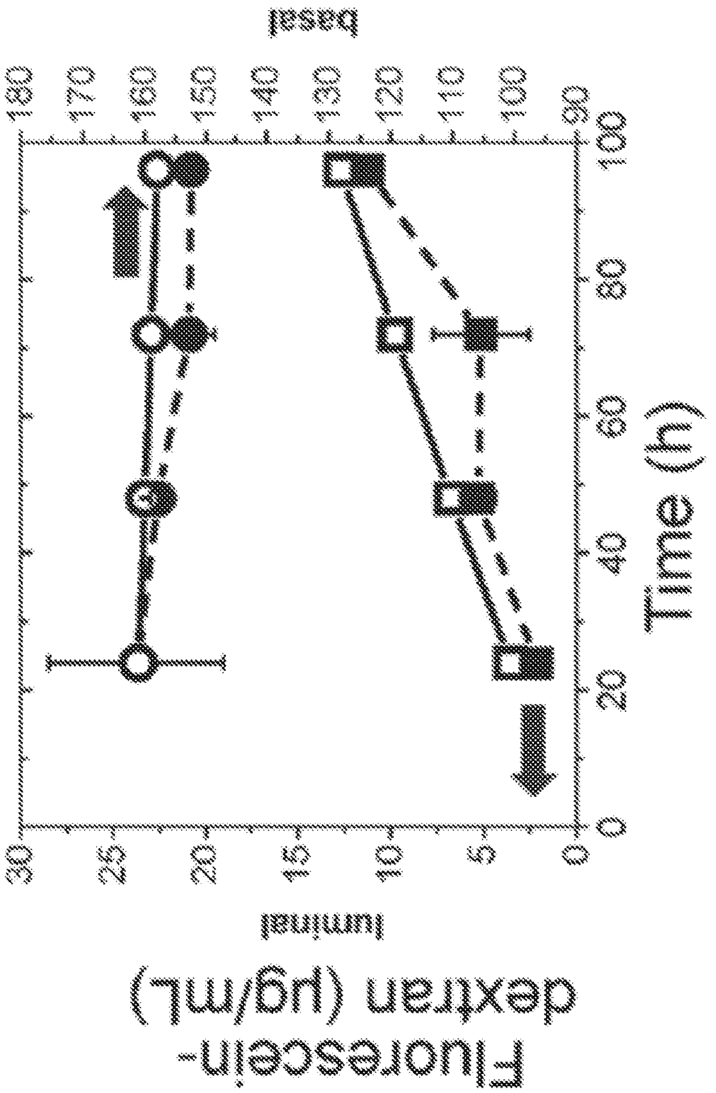
FIG. 4E is a graph showing the experimental measurement (solid shapes, dashed lines) and simulation results (open shapes, solid line) of the diffusion of fluorescein-dextran (40 kDa) between the luminal (squares) and basal (circles) containers of the apparatus of FIG. 4A over time (shown as fluorescein dextran concentration in micrograms per milliliter (μg/mL) versus time (in hours (h)). At time 0, fluorescein-dextran was added to the basal but not luminal container. The data points represent the average and the standard deviation of the measured data points (n=2), while the lines indicate the simulated concentrations.
Figure 4D:
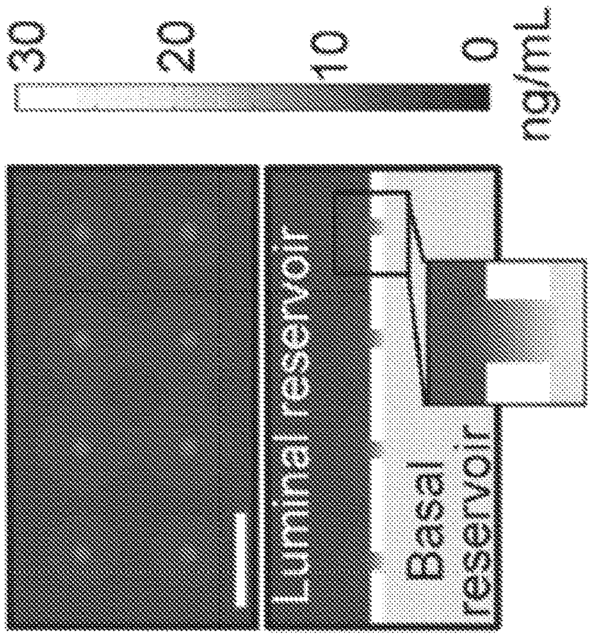
FIG. 4D is a pair of panels of a model of the diffusion of a 40 kilodalton (kDa) molecule from the basal container to the luminal container of the apparatus described in FIG. 4A. Top panel: Concentration profile of the 40-kDa molecules in the plane just above (10 μm) the luminal surface of the 1002F film. Shown is the concentration profile near 8 microholes in the center of the array at 24 h after addition of the molecule (30 ng/mL) to the basal reservoir. The white scale bar indicates 300 μm. Lower panel: Cross-sectional view through 4 microholes in the 1002F film. Inset shows a cross-section through a single microhole.

Fabrication and Characterization of Microdevice to Support Planar Intestinal Crypts An exemplary process for fabricating a microdevice apparatus to support planar intestinal crypts is shown in FIG. 4A. To fabricate the device, a layer (40 μm thick by SEM) of 1002F was coated onto a glass slide, and photopatterned using a mask with an array of 10×10 opaque circles (50 μm diameter, edge to edge distance of 300 μm. See FIG. 4B. The 1002F was removed from the glass slide by incubation in water and the 5 film was transferred to the base of a TRANSWELL® insert (Corning, Inc., Corning, N.Y., United States of America) from which the commercially attached membrane had been removed. The insert with attached 1002F film was placed onto a PDMS surface and collagen was loaded into the reservoir to form a 1 mm thick collagen gel above the micropatterned 1002F. The collagen was then dehydrated leaving a compacted collagen layer spanning the surface and bridging across the microholes and covered with salt crystals. See FIG. 4C, upper panel. Rehydration of the collagen provided a dense yet porous collagen membrane (4.7 μm thick by confocal fluorescence microscopy) across the entire upper surface of the device. See FIG. 4C, lower panel. The stiffness of the collagen layer in regions above the microhole and the 1002F surface was significantly different at 55.83±19.21 kPa and 146.38±42.27 kPa (n=3, 10 points per sample, $p<0.0001$), respectively, when measured by AFM with a 4.5 μm-diameter probe tip. The dehydration and rehydration process increased the collagen density across the 1002F surface since this step decreased the collagen thickness from 1 mm to 4.7 μm. In turn, this increased density likely increased the collagen stiffness which when not compacted possesses a reported stiffness of 10-1000 Pa depending on the concentration. See Wang et al., Cellular and Molecular Gastroenterology and Hepatology, 2017, 4, 165-182. The higher stiffness of the collagen-coated 1002F surface suggested that the collagen coating did not entirely mask the stiffness of the 1002F film. A typical stiffness of EPON resin is a few GPa. See Engelberg and Tesoro, Polymer Engineering &. Science, 1990, 30, 303-307; and Vallo et al., Polymer Gels and Networks, 1993, 1, 257-266. The indentation depth by AFM was approximately 150 nm, which is typically shallower than that sensed by cells. However, without being bound by any one theory, it is possible that the cells can “feel” the underlying stiff 1002F film more than can be sensed by the AFM tip. See Qu et al., Scientific Reports, 2018, 8, 3295; and Franck et al., PloS one, 2011, 6, e17833, The ability of growth factors to transit through the 1002F microholes and collagen film was simulated with COMSOL. See FIGS. 4D and 4E. The diffusion coefficient of a 40-kDa fluorescein-dextran (a similar molecular weight to those of Wnt-3A and R-spondin) in a hydrogel was previously measured as $7.4\times10^{-11}$ $m^2/s$. See Ahmad et al., RSC Advances, 2015, 5, 74881-74891. As a control, the movement of a fluorescein-dextran (40 kDa) over time from the basal to the luminal compartment was measured by sampling these reservoirs and compared to that predicted by the simulation. The results were in agreement. See FIG. 4E. The simulation predicts that 24 hours after loading fluorescein-dextran (30 ng/mL) into only the basal compartment, the fluorescein-dextran concentration in the luminal compartment was at its greatest level (7.3-8.3 ng/mL) over the collagen-coated microhole (10 μm above the surface) and declined rapidly in all directions, to 4.5-5.5 ng/mL at a point equidistant between the microholes. The steepest gradient of growth-factor concentration drop was 18 pg/mL/μm, which, without being bound to any one theory, is a value believed sufficient to induce colonic epithelial cells to form two cell compartments, a stem/proliferative and differentiated cell compartment. Prior measurements reported that a gradient of 75 pg/mL/μm was sufficient to polarize a 200 μm-long murine colonoid (see Ahmad et al., RSC Advances, 2015, 5, 74881-74891); however, this previous study did not incorporate a stiffness or porosity gradient, which can explain the requirement for a steeper gradient than that measured according to the presently disclosed subject matter. Since the above-described simulation did not incorporate turbulent or convective mixing, the gradient predicted by the simulation likely represents the minimal possible concentration difference along the 1002F surface. The simulation does, however, suggest that the collagen-coated, arrayed microholes could act as a localized source of growth-factors establishing a gradient of growth factor from the center of the microhole outward.

Example 2

Figure 5:
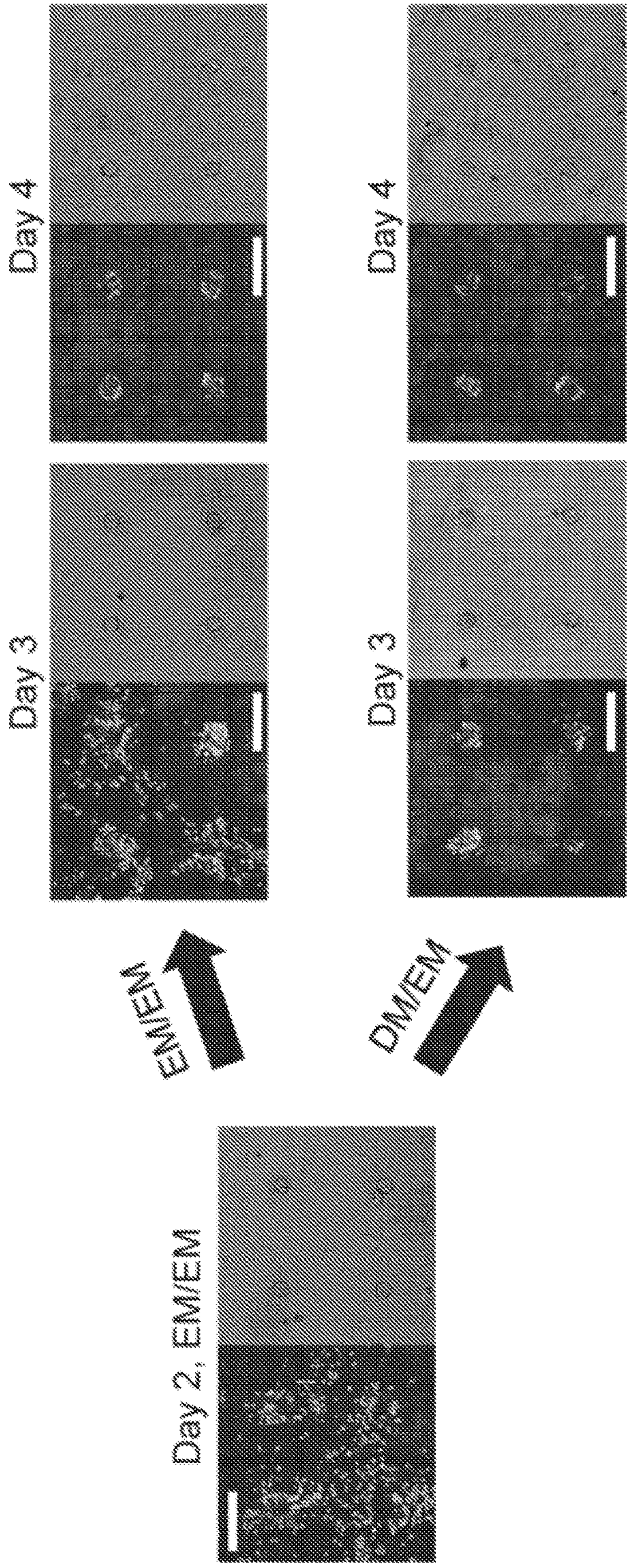
FIG. 5 is a series of pairs of confocal microscopy images (left: fluorescence image; right: differential interference contrast images) showing intestinal epithelial cell growth across a top surface of a cell support substrate comprising a collagen-coated photoresist film having four microholes in an array. The pair of images on the left (Day 2, EM/EM) were taken on day two of cell growth with both luminal and basal sides of the cell support exposed to expansion medium (EM). The top middle and top right pairs of images were taken on day 3 and day 4, respectively, of cell growth with media conditions remaining as expansion medium (EM) on both basal and lumina sides of the cell support (i.e., luminal/basal: EM/EM). The bottom middle and bottom right pairs of images were taken on day 3 and day 4, respectively, of cell growth, with the luminal side of the cell support exposed to differentiation medium (DM) and the basal side exposed to EM (i.e., luminal/basal: DM/EM). The images are taken along a single XY plane. The fluorescence images were analyzed for EdU-incorporation, ALP activity and Hoechst 33342 staining. The white scale bars represent 200 μm. All images are at the same magnification.
Figure 6A:
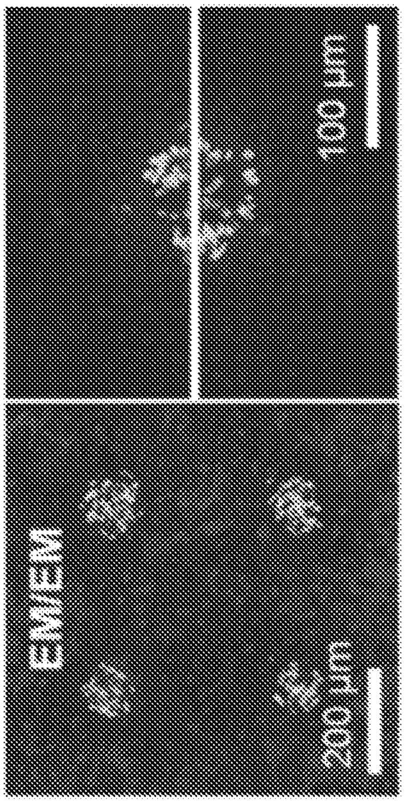
FIG. 6A is a pair of representative confocal microscopy images of primary murine intestinal epithelial cell growth on a cell support substrate of the presently disclosed subject matter. Cells are exposed to expansion medium (EM) on both the luminal and basal sides of the support (i.e,, luminal/basal: EM/EM). The image on the left is a projected image of four planar crypts and the image on the right is an image of a single planar crypt under higher magnification. The white line in the center of the image on the right marks the location of the cross-sectional confocal view through the cell monolayers shown in FIG. 6B. Light spots in the centers of the crypts represent EdU-incorporation, while grey spots outside of the centers represent ALP activity. The scale bar at the bottom right of the image on the left represents 200 micrometers (μm), and the scale bar at the bottom right of the image on the right represents 100 μm.
Figure 6B:
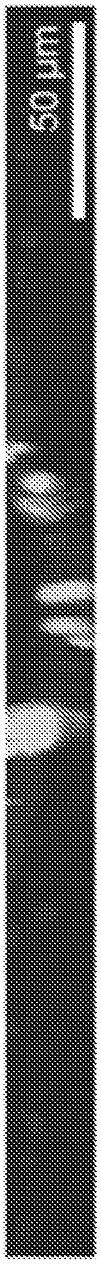
FIG. 6B is a representative cross-sectional confocal microscopy image of primary murine intestinal epithelial cell growth in a single planar crypt on a cell support substrate of the presently disclosed subject matter. Cells are exposed to expansion medium (EM) on both the luminal and basal sides of the support (i.e., luminal/basal: EM/EM). Light spots represent EdU-incorporation. The scale bar at the bottom right of the image represents 50 micrometers (μm).
Figure 6C:
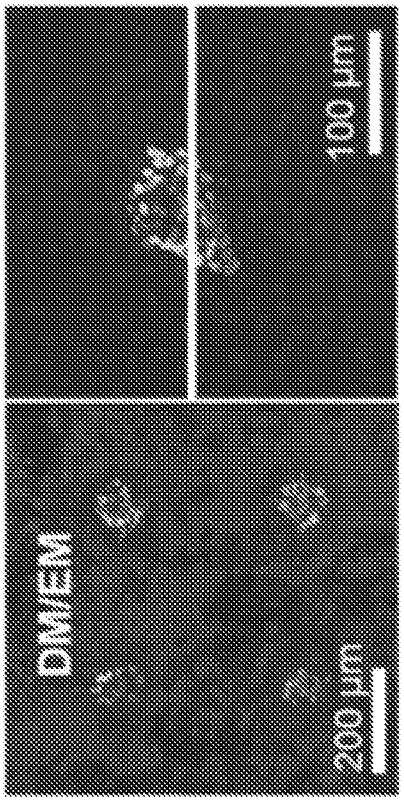
FIG. 6C is a pair of representative confocal microscopy images of primary murine intestinal epithelial cell growth on a cell support substrate of the presently disclosed subject matter. Cells are exposed to differentiation medium (DM) on the luminal side of the support and expansion medium (EM) on the basal side of the support (i.e., luminal/basal: DM/EM). The image on the left is a projected image of four planar crypts and the image on the right is an image of a single planar crypt under higher magnification. The white line in center of the image on the right marks the location of the cross-sectional confocal view through the cell monolayers shown in FIG. 6D. Light spots represent EdU-incorporation, while grey spots represent ALP activity. The scale bar at the bottom right of the image on the left represents 200 micrometers (μm), and the scale bar at the bottom right of the image on the right represents 100 μm.
Figure 6D:
FIG. 6D is a representative cross-sectional confocal microscopy image of primary murine intestinal epithelial cell growth in a single planar crypt on a cell support substrate of the presently disclosed subject matter. Cells are exposed to differentiation medium (DM) on the luminal side of the support and expansion medium (EM) on the basal side of the support (i.e., luminal/basal: DM/EM). Light spots represent EdU-incorporation. The scale bar at the bottom right of the image represents 50 micrometers (μm).
Figure 6E:
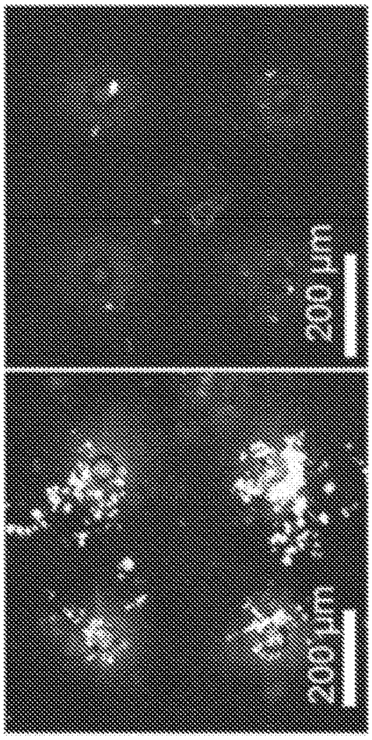
FIG. 6E is a pair of fluorescent images of four planar crypts exposed to differentiation medium (DM) on the luminal side of the support and expansion medium (EM) on the basal side of the support substrate (i.e., luminal/basal: DM/EM). The image on the left is stained for mucin-2, while that on the right is stained for chromogranin A and Hoechst 33342. The scale bar in the lower left of each image represents 200 micrometers (μm).

Growth of Primary Mouse Intestinal Epithelial Cells on Collagen-Coated, Patterned Film Cells were cultured on the collagen-coated 1002F films with patterned microholes for 4 days with EM or stem-cell supporting media in the luminal (upper) and basal (lower) reservoirs (EM/EM). Four days of culture time was chosen to mimic the typical life time (3-5 days) of murine colonic epithelial cells. See Tsubouchi, Developmental Dynamics, 1981, 161, 239-246. Cell proliferation and differentiation as indicated by EdU incorporation and alkaline phosphatase (ALP) activity, respectively, was tracked over time. See FIG. 5. At day 2, the cells exhibited robust proliferation as demonstrated by incorporation of EdU in cells across the film surface. In contrast, very little ALP activity was detected in the epithelial cells suggesting that under these conditions and at this time point, very few differentiated cells were present. At day 3 of culture, EdU+ cells remained present throughout the array accompanied by low levels of ALP activity. However, by day 4 of culture, distinctive cell patterning was present with circular regions of EdU+ cells extending 50-60 μm out from the microhole centers. See FIG. 5 and FIGS. 6A and 6J. No EdU+ cells were present at distannces greater than 70 μm from the through microcenter. See FIG. 5 and FIGS. 6A and 6J. In contrast, low levels of ALP activity in cells at a distance greater than 90 μm from a microhole center remained present. See FIG. 5 and FIGS. 6A and 6K. No cells within 70 μm of a microhole center expressed measurable ALP activity. Cells in the transition zone between 60-70 μm from a microhole center possessed little EdU incorporation or ALP activity suggesting that in these regions proliferative and differentiation signals were equally balanced.

To understand this distinctive patterning despite the provision of EM with growth factors to all cells, cells were cultured on a collagen-coated 1002F film without microholes under EM/EM so that all cells experienced the stiff and impermeable underlying 1002F surface. At day 4 of culture, the cells demonstrated no EdU incorporation suggesting that the under these conditions the impact of the 1002F surface dominated and forced the cells to cease dividing. Cells were also cultured on a collagen layer without the underlying 1002F film for 4 days under EM/EM. Nearly all of these cells remained EdU+ during this time period. In the presence of a lower stiffness and higher porosity substrate, the growth factors were competent to drive cell proliferation. Thus, the changes in the material properties of the underlying matrix alone were sufficient to create two cellular zones on the array: a highly proliferative region and a nonproliferative compartment with evidence of cell differentiation. Porosity has a significant impact on stem cell behavior, though often in hydrogel systems its effect is coupled with stiffness, since crosslinking frequently is used to increase stiffness (also reducing pore size). As an example, the migration of mesenchymal stem cells using PEG hydrogels has been shown to depend on scaffold porosity as well as stiffness and adhesivity. See Peyton et al., Biotechnology and Bioengineering, 2011, 108, 1181-1193. Additionally, the porosity of a rigid polystyrene can alter the growth of neurites derived from human stem cells. See Hayman et al., Journal of Biochemical and Biophysical Methods, 2005, 62, 231-240. Porosity can also impact the cell morphology and cytoskeletal organization within epithelial cells. MDCK II cells, a model epithelial cell line, adopt a more flattened, spread out morphology and develop thicker actin stress fibers on a nonporous substrate compared to that on a porous substrate. See Rother et al., Journal of the Royal Society Interface, 2015, 12, 20141057; and Janshoff et al., Journal of Adhesion Science and Technology, 2010, 24, 2287-2300. The stiffness change between the collagen-covered microholes and the collagen-coated 1002F, while small, can also potentially impact cell behavior. Stiffer surfaces have been shown to decrease protein levels of the Oct3/4 or Nanog pluripotency stem-cell markers in embryonic stem cells relative to softer surfaces suggesting that the harder surfaces can increase differentiation. See Chowdhury et al., PloS one, 2010, 5, e15655; and Lü et al., Biomaterials, 2014, 35, 3945-3955. Finally, mouse and human intestinal stem cells have been shown to cease to proliferate and appear to adopt a more differentiated phenotype on very stiff surfaces such as polystyrene or poly(dimethyl siloxane) relative to softer surfaces. See Wang et al., Cellular and Molecular Gastroenterology and Hepatology, 2017, 4, 165-182. In summary, the presently disclosed studies are in agreement with previous work showing that changes in porosity and stiffness can combine to alter cell fate. It should be noted that the EM contains ROCK inhibitor Y-27632, which is commonly used to inhibit anoikis in primary intestinal cell culture. Since ROCK signaling is known to modulate mechanosensing and mechanotransduction (see Yim and Sheetz, Stem Cell Research & Therapy, 2012, 3, 41; and Provenzano and Keely, J. Cell Sci, 2011, 124, 1195-1205), it is possible that the presence of Y-27632 alters the response to substrate stiffness.

Figure 6F:
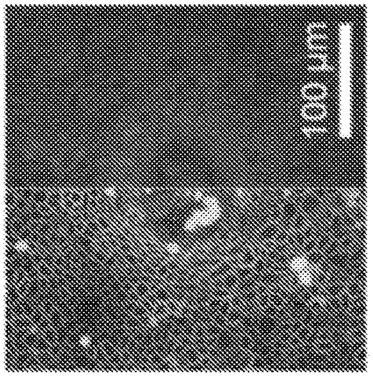
FIG. 6F is a projected split image of E-cadherin (left side) and β-catenin (right side) immunofluorescence staining of a single planar crypt exposed to expansion medium (EM) on both the luminal and basal side of the support substrate (luminal/basal: EM/EM). The scale bar in the lower right side of the image represents 100 micrometers (μm).

The properties of the cells in the different regions of the presently disclosed arrays were further investigated to gain insight into the surface impact on cell behavior. A cross-section through the cells along the Z-axis confirmed that all regions on the surface grew as a monolayer. See FIG. 6B. The cell outlines visualized by E-cadherin staining in FIG. 6F show that the cell density over the microholes (2.2±0.1 cells/100 $\mu m^2$) was significantly different (n=3 crypts, $p<0.0005$) from that in regions between the microholes (0.8±0.1 cells/100 $\mu m^2$), suggesting that the cells over the microholes were more columnar in shape (as in the in vivo intestinal epithelium) while those in the intermediate regions adopted a wider more flattened shape. These results are consistent with the known responses of epithelial cells to porous and nonporous substrates noted above. However, cells in all regions of the surface expressed the adherens junction marker E-cadherin, suggesting that cell-cell adhesion was maintained throughout the surface. See FIG. 6F. β-catenin, a downstream effector of Wnt signaling that binds to cadherins in the adherens junction complex (see Valenta et al., The EMBO Journal, 2012, 31, 2714-2736) was also prominent on cells in all regions (see FIG. 6F) indicating that all cells continue to experience Wnt-3A binding and signaling even though the cells far from the microholes fail to undergo Wnt-3-driven proliferation. These data demonstrate that stiffness and/or porosity were sufficient to initiate cell segregation into two regions: i) a proliferative region with few enterocytes and a high density of cells and ii) a nonproliferatve region higher in the enterocyte marker ALP and adopting a more flattened shape.

Example 3

Creation of Stem/Proliferative Cell Compartment and Differentiated Cell Zone

Without being bound to any one theory, the absence of high ALP activity in the differentiated cells was possibly due to the continued presence of the growth factors, Wnt-3, Noggin and R-Spondin. Cells were cultured on the arrays in EM/EM for 2 days to enable the cells to attach and spread across the collagen-coated surface and then switched to DM/EM (luminal/basal) for an additional 2 days. DM or differentiation medium does not contain Wnt3A, R-spondin or Noggin and three-differentiates intestinal epithelial cells towards the enterocyte or absorptive cell lineage. See Wang et al., ACS Biomaterials Science & Engineering, 2017, 3, 2502-2513. To determine the fate of the cells exposed to DM/EM, cell proliferation and differentiation were tracked over time. See FIG. 5. At day 3 of culture, proliferative cells were largely localized to the surface regions above the microholes while cells with ALP activity were restricted to other regions. By day 4, two distinct cells compartments were readily visualized. The proliferative cell compartment located only above the microholes was not statistically different in size from that created after 4 days of EM/EM. See FIGS. 6C, 6D, and 6J. This suggests that cells over the microholes had ready access to the growth factors in EM via diffusion through the microhole. In contrast, the ALP activity in cells began to increase at 60 μm from the microhole center reaching a maximum activity at 130 μm. In these outer regions, the ALP activity was significantly increased (4.5-fold, n=5 crypts, $p<0.0005$) from that produced by EM/EM. See FIG. 6K. The DM in the upper reservoir along with the underlying surface directed the intestinal epithelial cells to a nonproliferative phenotype with greatly increased ALP activity creating differentiated cell zones (>130 μm) surrounding the proliferative cell zones (0-50 μm) above the microholes. This compartmentalized culture lasted at least up to day 6.

To confirm that the central proliferative zones were created by diffusion of growth factors through the microholes from the underlying EM, several controls were performed. Each control experiment cultured the cells on EM/EM for 2 days on the surface indicated below and then for a further 2 days in media as indicated below. In the first experiment, intestinal cells were cultured on a flexible collagen membrane without an underlying 1002F film and then placed into DM/EM for days 3-4. Proliferative cells were present throughout the array surface at day 4 again suggesting that the growth factors readily diffused through the collagen layer. In the second control experiment, cells were cultured on a collagen-coated 1002F film without microholes and on day 3-4 placed into DM/EM. As expected, no EdU+ cells were present but ALP activity was apparent across the surface. In the third experiment, cells were cultured on a collagen-coated array of microholes and then on day 3-4 placed into DM/DM. These devices possessed no EdU+ cells at day 4 indicating that the collagen film above the microhole was not sufficient to support cell proliferation in the absence of growth factors. The highest ALP activity was observed on these arrays with the ALP activity at 100-110 μm from the microhole center significantly greater (2.2X, n=5 crypts, $p<0.005$) than that for the DM/EM culture. See FIG. 6K. The wide difference in ALP activity of the DM/EM and DM/DM suggests that small amounts of growth factors likely diffused into the differentiated cell zones of the DM/EM cultures.

Figure 6G:
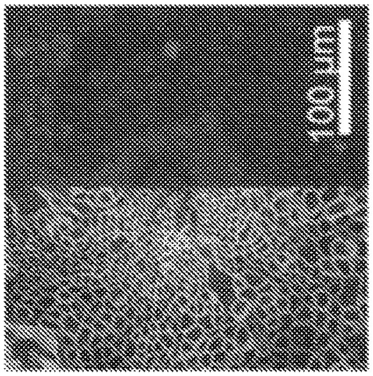
FIG. 6G is a projected split image of E-cadherin (left side) and β-catenin (right side) immunofluorescence staining of a single planar crypt exposed to differentiation medium (DM) on the luminal side of the support substrate and expansion medium (EM) on the basal side of the support substrate (i.e., luminal/basal: DM/EM). The scale bar in the lower right side of the image represents 100 micrometers (μm).
Figure 6H:
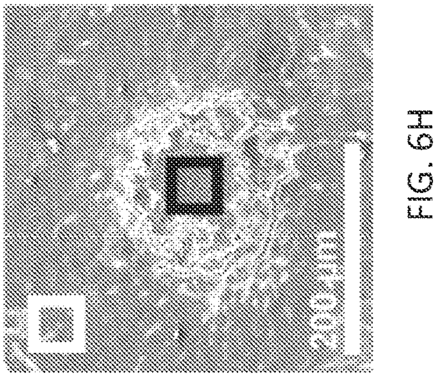
FIG. 6H is a representative scanning electron microscopy image of a single planar crypt exposed to differentiation medium (DM) on the luminal side of the support substrate and expansion medium (EM) on the basal side of the support substrate (i.e.. luminal/basal: DM/EM). The black and white boxes indicate the center region and the edge regions, respectively, of the crypt areas shown at higher magnification in FIG. 6I. The scale bar at the bottom of the image represents 200 micrometers (μm).
Figure 6I:
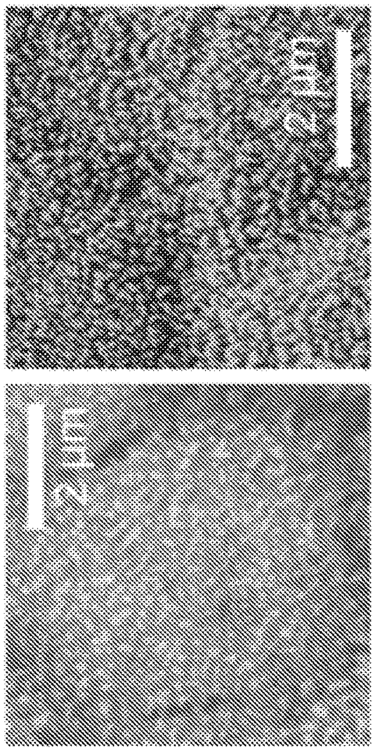
FIG. 6I is a pair of representative high magnification scanning electron microscopy images of different regions in the planar crypt shown in FIG. 6H shown at higher magnification. The image on the left represents cells in the center of the crypt, corresponding to the area in the back box in FIG. 6H. The image on the right represents cells in the edge region of the crypt, corresponding to the area in the white box in FIG. 6H. The scale bars at the top right of the image on the left and the bottom right of the image on the right represent 2 micrometers (μm).
Figure 6J:
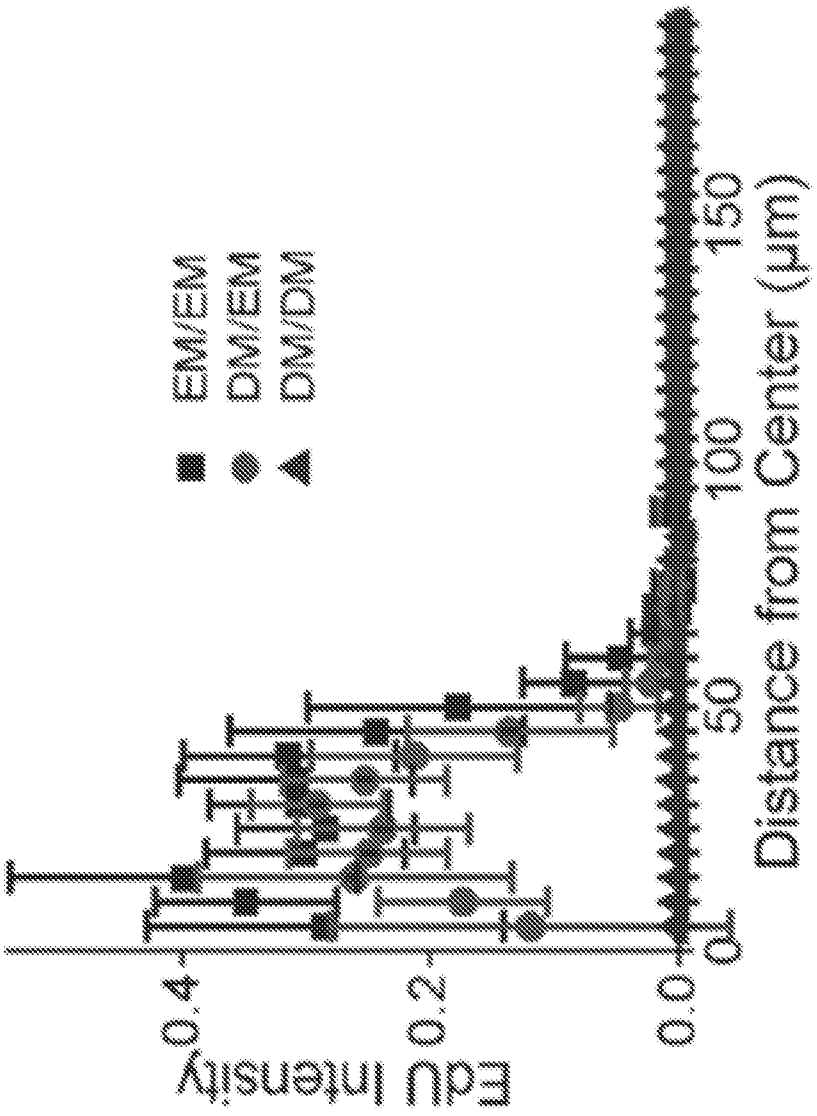
FIG. 6J is a graph showing the normalized fluorescence intensity of incorporated 5-Ethynyl-2'-deoxyuridine (EdU) in the radial direction (measured in micrometers (μm) outward from the center of a crypt for cells grown on a cell support substrate of the presently disclosed subject matter and treated with expansion medium on both the luminal and basal sides of the cell support substrate (luminal/basal: EM/EM, squares), differentiation medium on the luminal side of the cell support substrate and expansion medium on the basal side of the cell support substrate (luminal/basal: DM/EM, circles), and differentiation medium on both the luminal and basal sides of the cell support substrate (luminal/basal: DM/DM, triangles). The data points reflect the average and the error bars reflect the standard deviation for 5 samples where the fluorescence image was measured in concentric rings 5 μm in width from the center of the crypt.
Figure 6K:
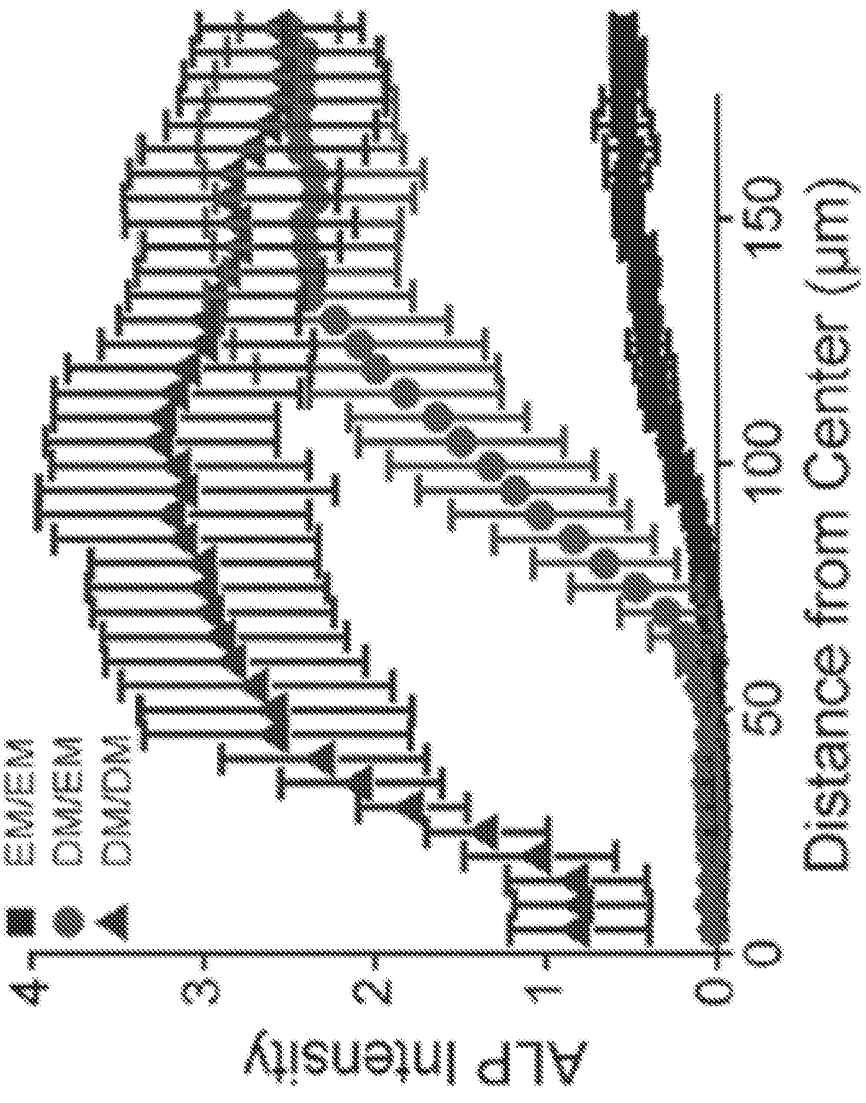
FIG. 6K is a graph showing the normalized fluorescence intensity of incorporated alkaline phosphatase (ALP) activity in the radial direction (measured in micrometers (μm) outward from the center of a crypt for cells grown on a cell support substrate of the presently disclosed subject matter and treated with expansion medium on both the luminal and basal sides of the cell support substrate (luminal/basal: EM/EM, squares), differentiation medium on the luminal side of the cell support substrate and expansion medium on the basal side of the cell support (luminal/basal: DM/EM, circles), and differentiation medium on both the luminal and basal sides of the cell support substrate (luminal/basal: DM/DM, triangles). The data points reflect the average and the error bars reflect the standard deviation for 5 samples where the fluorescence image was measure in concentric rings 5 μm in width from the center of the crypt.

The planar crypt with proliferative and differentiation zones was further characterized by immunofluorescence and SEM. As shown in FIG. 6G, the cells in the planar crypt under DM/EM maintained cell-cell adhesions throughout the area as indicated by the presence of E-cadherin, while Wnt signaling, visualized by β-catenin, was localized predominantly near the microholes. Under DM/EM, cells in the differentiated zones lost access to growth factors enabling these cells to progress farther down the enterocyte differentiation pathway. SEM images revealed prominent microvilli, a characteristic of absorptive colonocyte, on cells away from the microhole in the differentiated zone and less dense and shorter microvilli on cells over the center of the microholes suggesting a less differentiated cell type. See FIGS. 6H and 6I. The presence of goblet cells in the planar crypt was also confirmed by immunofluorescence staining of mucin-2. See FIG. 6E, left image. In contrast to the enterocytes, the goblet cells were predominantly located near the microholes, which is consistent with the placement of large numbers of goblet cells deep within the crypts in vivo. See Birchenough et al., Science, 2016, 352, 1535-1542. Lastly, the planar crypt possessed a small number (about 2 per planar crypt) of chromogrannin-A expressing enteroendocrine cells (see FIG. 6E, right image) which is consistent with the sparsity of this cell type in vivo. See Stemini et al., Current Opinion in Endocrinology, Diabetes, and Obesity, 2008, 15, 73. Accordingly, the presently disclosed planar crypt array reproduces the cell segregation found in vivo, but in two-dimensions and in an easy to fabricate and maintain format.

Example 4

Migration and Death of Intestinal Epithelial Cells on Planar Crypt Arrays

Figure 7B:
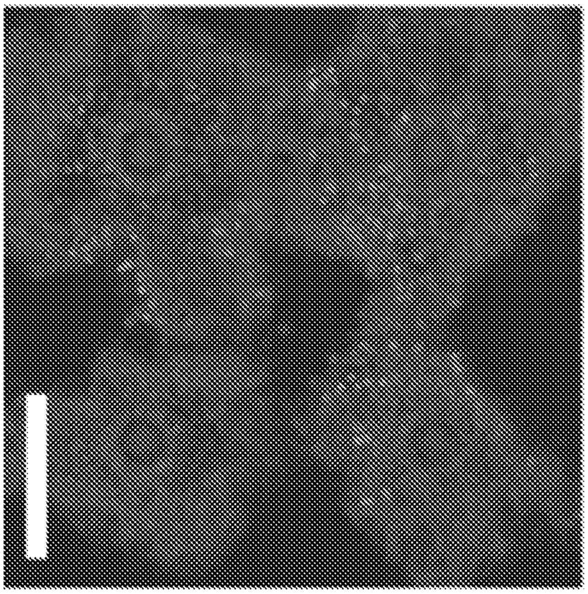
FIG. 7B is a confocal fluorescence microscopic image of four planar crypts cultured on a cell support substrate of the presently disclosed subject matter and pulsed with 5-ethynyl-2'-deoxyuridine (EdU) as described for the cells shown in FIG. 7A but cultured for an additional 2 days in an EdU-free medium prior to fixation and staining. The scale bar in the upper left represents 200 micrometers (μm).
Figure 7A:
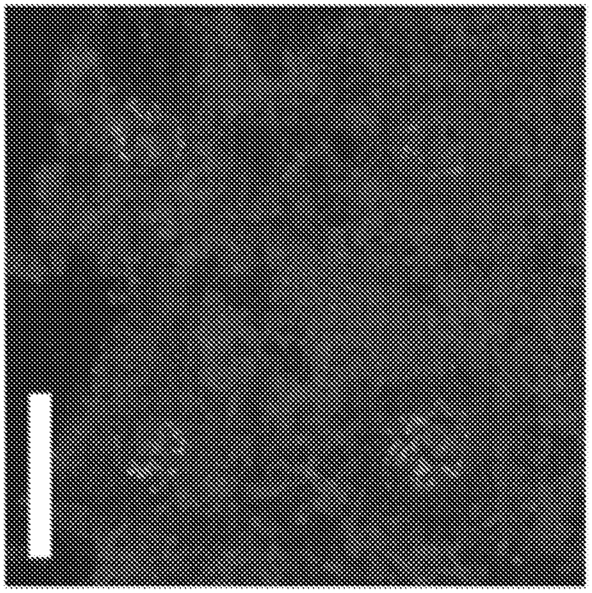
FIG. 7A is a confocal fluorescence microscopic image of four planar crypts cultured on a cell support substrate of the presently disclosed subject matter with differentiation medium (DM) on the luminal side of the support substrate and expansion medium (EM) on the basal side of the support substrate for 4 days and then incubated with 5-ethynyl-2'-deoxyuridine (EdU) for 3 hours followed by cell fixation and staining. The scale bar in the upper left represents 200 micrometers (μm).
Figure 7D:
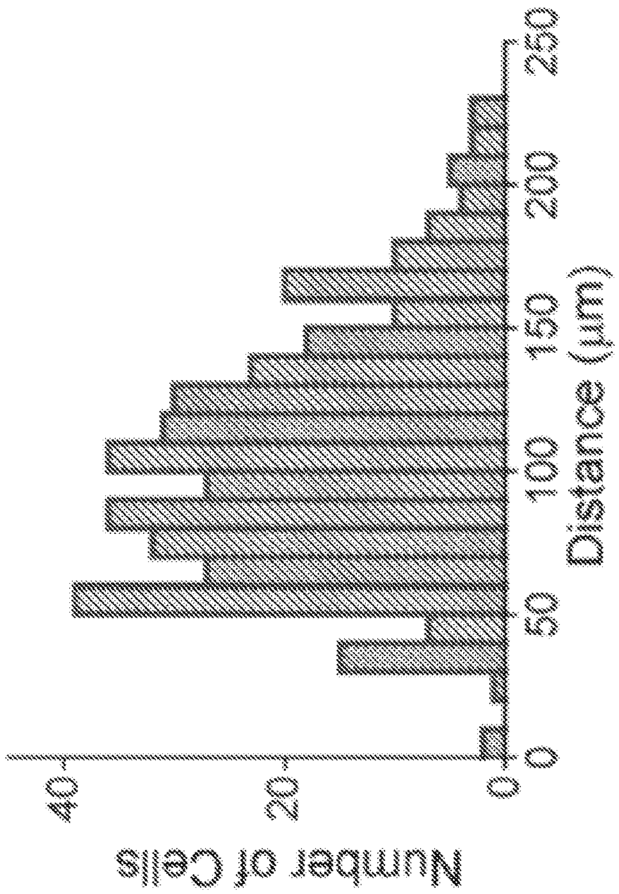
FIG. 7D is a graph showing the number of 5-ethynyl-2'deoxyuridine (EdU) positive cells cultured as described in FIG. 7B at different distances (measured in micrometers (μm)) from the center of the crypt after pulse with EdU and washout for 2 days. N=5.
Figure 7C:
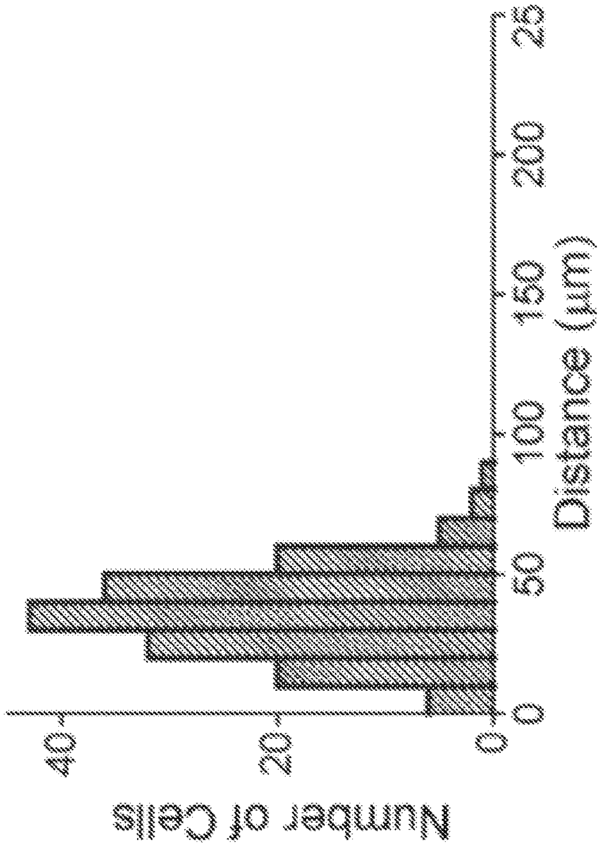
FIG. 7C is a graph showing, the number of 5-ethynyl-2'deoxyuridine (EdU) positive cells cultured as described in FIG. 7A at different distances (measured in micrometers (μm)) from the center of the crypt immediately after the 3 hour pulse with EdU. N=5.

In the intestine in vivo, stem cells at the base of the crypt proliferate giving rise to transit amplifying cells that continue to divide and migrate up the long axis of the crypt toward the luminal surface of the intestine. As the cells approach the lumen, the cells differentiate into the nondividing lineages (enterocytes, goblet cells and enteroendocrine cells). See Barber, Nature Reviews Molecular Cell Biology, 2014, 15, 19. To determine whether cells on the planar crypt arrays recapitulate this orderly cell migration from the proliferative cell compartment to the differentiated cell regions, mouse endothelial cells on the collagen-coated microhole arrays were cultured in EM/EM for 2 days (days 1-2) and then polarized in DM/EM for a further 2 days (days 3-4). The cells were then incubated with EdU for three hours after which time the EdU was washed away and the cells cultured for an additional 2 days in DM/EM (days 5-6). The location of the EdU+ cells was measured on day 4 immediately after EdU incubation and again on day 6 (after the 2-day chase time). As expected on day 4, all EdU+ cells were located above the microholes in the proliferative cell zone (mean cell location of 36±15 μm from the microhole center, n=165 cells). See FIGS. 7A and 7C. However, at day 6, the majority of EdU+ cells were located in the differentiated cell zones (mean cell location of 105±44 μm from the microhole center, n=386 cells; see FIGS. 7B and 7D) indicating that these cells migrated from the proliferative zone (pulse location) into the differentiated cell zone during the intervening 2 days. The locations of the EdU+ cells at day 6 were statistically different from their position at day 4

(p<0.0001). Many of the EdU+ cells were also co-localized with the ALP activity measured at day 6 indicating that these day-4, proliferative cells differentiated during their outward migration. The average speed of these cells was 1.6±1.1 μm/h (the difference in the mean EdU+ cell location at 0 and 44 h after EdU washout divided by 44 h) which is similar to the cell migration velocity in the lower crypt in viva (1.3 μm/h). See Tsubouchi, Developmental Dynamics, 1981, 161, 239-246. The flow of cells from the stem/proliferative niche at the crypt base upward to the luminal surface of the intestine was recreated in the planar crypt array.

In vivo epithelial cells on the luminal surface of the murine large intestine live an average of 5 days. See Tsubouchi, Developmental Dynamics, 1981, 161, 239-246. After these luminal cells die, they are sloughed into the intestinal lumen making room for newly arriving cells. See Barkla and Gibson, Pathology, 1999, 31, 230-238. To understand the fate of the differentiated cells on the planar crypt arrays, cells were cultured in EM/EM for 2 days and then DM/EM for an additional 2 days. Necrotic and apoptotic cells were visualized by staining the arrays with propidium iodide (marking all dead cells) and fluorescein-annexin V (marking apoptotic cells). Very few cells in the proliferative zones exhibited propidium iodide or annexins V fluorescence. In contrast, dead and dying cells were readily observed in the differentiated cell regions. In regions distant from the through holes, dying cells sometimes detached in a group leaving exposed regions of collagen-coated photoresist. Taken together these data suggest that the progeny of the dividing cells in the proliferative zone migrate outward into the differentiated cell regions maturing into enterocytes as they move outward. At the end of their lifetime, these nondividing cells die by apoptosis and are replaced by newly arriving cells from the proliferative zone. These features replicate the life cycle of cells as they move from the crypt base to the luminal epithelium in vivo.

Example 5

Figure 8B:
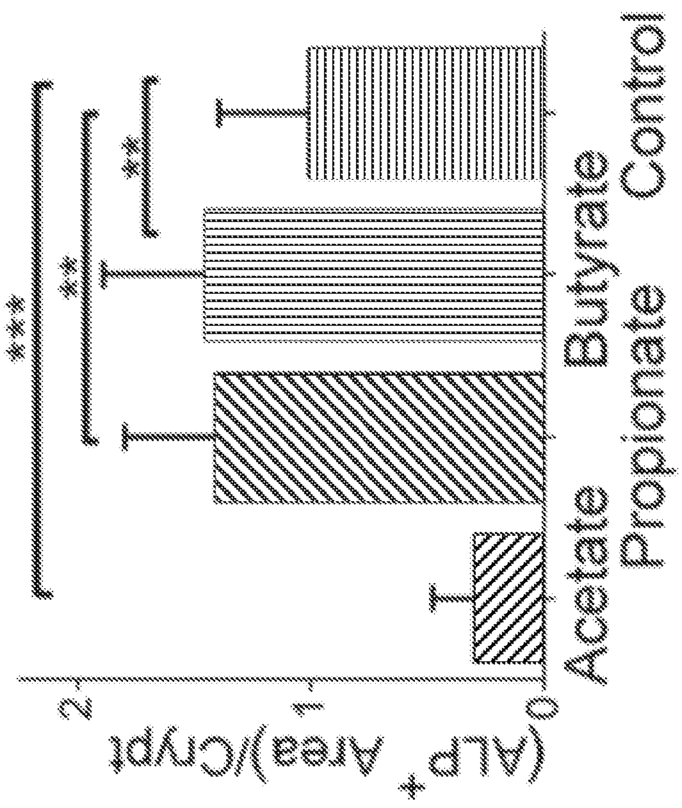
FIG. 8B is a graph showing the alkaline phosphatase (ALP) positive area per crypt for planar crypts treated as described in FIG. 8A. "Control" represents crypts treated with differentiation medium (DM) on the luminal side of the cell support substrate and expansion medium (EM) on the basal side of the cell support substrate. "Acetate" represents crypts where the DM included acetate, "Propionate" represents crypts where the DM included propionate, and "Butyrate" represents crypts where the DM included butyrate. ALP positive area per crypt was normalized against Hoechst 33342 stained area per unit crypt. Ten crypts each from 2 different mice (total 20 crypts) were analyzed.  and * indicate $P \leq 0.01$ and $P \leq 0.001$, respectively.
Figure 8A:
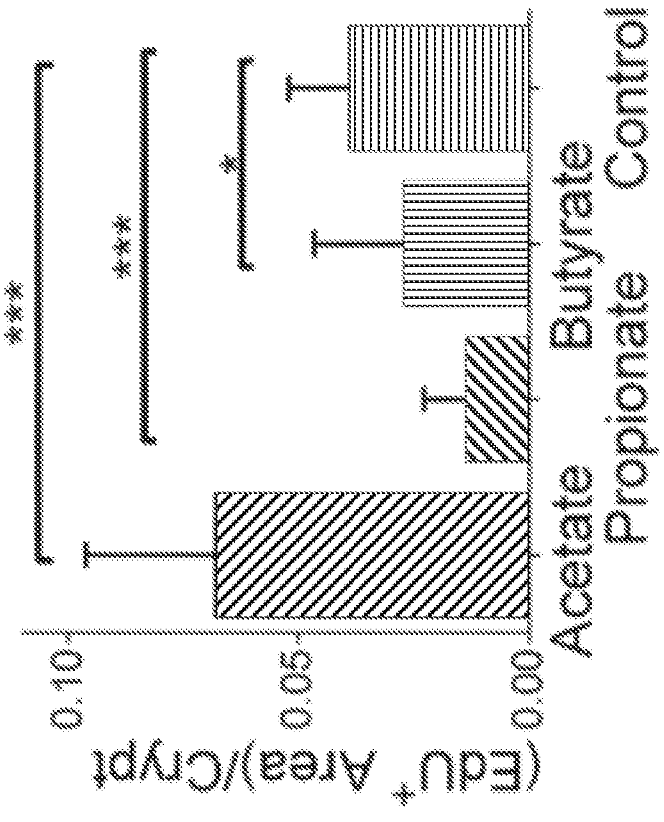
FIG. 8A is a graph showing the 5-ethynyl-2'-deoxyuridine (EdU) positive area per crypt for planar crypts treated as follows: crypts grown with differentiation medium (DM) on the luminal side of the cell support substrate and expansion medium (EM) on the basal side of the cell support substrate (DM/EM; control); DM plus acetate on the luminal side and EM on the basal side (DM+acetate/EM); DM plus propionate on the luminal side and EM on the basal side (DM+propionate/EM); and DM plus butyrate on the luminal side and EM on the basal side (DM+butyrate/EM). "Control" represents crypts treated with differentiation medium (DM) on the luminal side of the cell support substrate and expansion medium (EM) on the basal side of the cell support substrate. "Acetate" represents crypts where the DM included acetate, "Propionate" represents crypts where the DM included propionate, and "Butyrate" represents crypts where the DM included butyrate. EdU positive area per crypt was normalized against Hoechst 33342 stained area per unit crypt. Ten crypts each from 2 different mice (total 20 crypts) were analyzed. *,  and * indicate $P \leq 0.05$, $P \leq 0.01$ and $P \leq 0.001$, respectively.
Figure 8C:
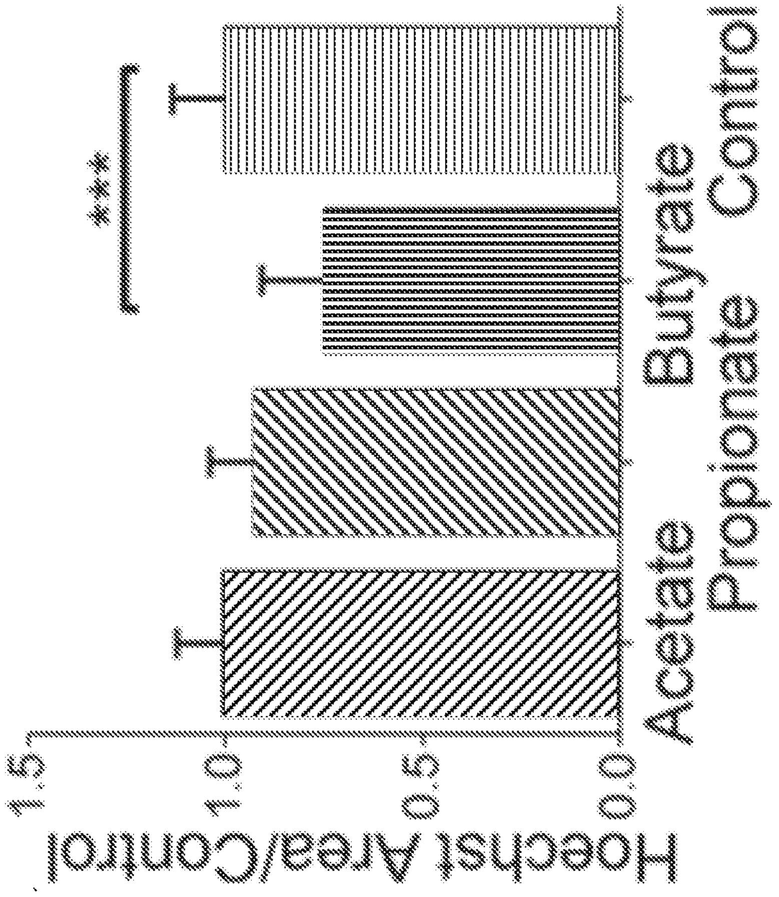
FIG. 8C is a graph showing the Hoechst 33342 positive area for the different fatty acids per unit crypt compared to Hbechst 33342 positive area control crypts. Crypts were treated as described in FIG. 8A. "Control" represents crypts treated with differentiation medium (DM) on the luminal side of the cell support substrate and expansion medium (EM) on the basal side of the cell support substrate. "Acetate" represents cells where the DM included acetate, "Propionate" represents crypts where the DM included propionate, and "Butyrate" represents crypts where the DM included butyrate. Ten crypts each from 2 different mice (total 20 crypts) were analyzed. *** indicates $P \leq 0.001$.

Effect of Short Chain Fatty Acids on the Proliferation and Differentiation of Mouse Intestinal Epithelial Cells Colonic epithelial proliferation and differentiation is impacted by microbial products such as short chain fatty acids which are produced during bacterial fermentation of fibrous materials. See Koh et al., Cell, 2016, 165, 1332-1345. For instance, propionate and butyrate suppress proliferation in intestinal tumor cell lines. See Gamet et al., International Journal of Cancer, 1992, 52, 286-289: and Whitehead et al., Gut, 1986, 27, 1457-1463. Butyrate also decreases proliferation in primary murine intestinal organoids. See Kaiko et al., Cell, 2016, 165, 1708-1720. To evaluate the effect of short chain fatty acids on proliferation and differentiation of intestinal epithelial cells on the planar crypt arrays, short chain fatty acids (24 mM of acetate, 6 mM of propionate, or 1 mM of butyrate) was added in the DM luminal medium during the 2-day polarization time i.e. day 3-4 of cell culture on the arrays. The EdU+ and ALP+ areas were measured and normalized to the area positive for Hoechst 33342 (total cell nuclei area as a proxy for cell number). Acetate significantly increased the normalized area of EdU+ cells. Propionate and butyrate significantly decreased the normalized area of EdU+ cells compared to that of the control without the short chain fatty acid. See FIG. 8B. This is consistent with the behavior of mouse intestinal cells cultured as a monolayer on a collagen gel (see Wang et al., Cellular and Molecular Gastroenterology and Hepatology, 2017, 4, 165-182), mouse intestinal organoids within a Matrigel patty (see Kaiko et al., Cell, 2016, 165, 1708-1720) and tissue-cultured HT29 human colon cancer cells. See Gamet et al., International Journal of Cancer, 1992, 52, 286-289. In contrast, acetate significantly decreased ALP activity while propionate and butyrate significantly increased ALP activity relative to the control, See FIG. 8C. Butyrate and propionate significantly increased ALP activity, similar to the impact of these two short chain fatty acids when applied as a gradient to three-dimensional crypts formed from primary human colonic cells. See Wang et al., Cellular and Molecular Gastroenterology and Hepatology, 2018, 5, 113-130. Butyrate increased ALP activity significantly more than did Butyrate was the only short chain fatty acid to decrease the number of Hoechst 33342+ cells per crypt by about 17% (p<0.001) (see FIG. 8D) which is consistent with the previous observation that butyrate induces apoptosis in human colon cancer cell lines. See Ruemmele et al., Gut, 2003, 52, 94-100; Fung et al., Journal of Proteome Research, 2011, 10, 1860-1869: and Xu et al., Signal Transduction and Targeted Therapy, 2017, 2, 16035. These data demonstrate that the planar crypt arrays reproduce key intestinal epithelial cell responses to microbial metabolites.

Example 6

Formation of Planar Crypt for Human Intestinal Epithelial Model System

Figure 9:
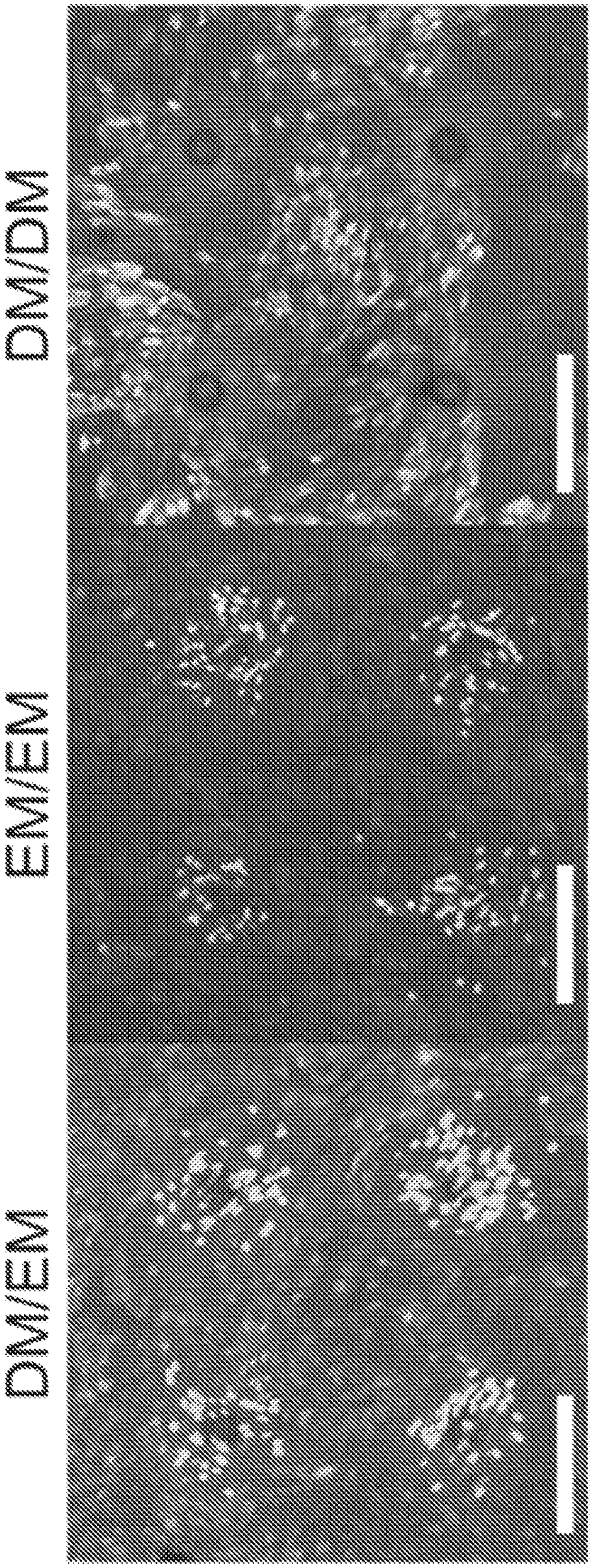
FIG. 9 is a set of three representative confocal fluorescence microscopy images of four crypts of human epithelial cells grown using an apparatus of the presently disclosed subject matter under three different media conditions: differentiation medium (DM) on the luminal side and expansion medium (EM) on the basal side (DM/EM, left), EM on both sides (EM/EM, center) and DM on both sides (DM/DM). The scale bar in the lower left of each image represents 200 micrometers (μm).

The same microdevice as described in Example 1 and used in Example 2 was used to create human planar crypt using primary human intestinal epithelial cells. Human primary epithelial cells were cultured in this platform for 4 days in the presence of the growth factors in the luminal and basal media. On day 4, the cells were further incubated for 4 days with 1) EM/EM condition where the growth factors were present both in the luminal and basal media, 2) DM/EM condition where the growth factors were present only in the basal medium and finally 3) DM/DM condition where growth factors were absent in both compartments. The media were changed every two days during the culture. On day 8, the cells were pulsed with EdU for 3 days, then subjected to the ALP assay for 30 min, and then fixed to label proliferative cells and colonocytes respectively. Goblet cells were detected by immunofluorescence using MUC2 antibody. EdU was detected by conjugating Cy5 fluorophore through click chemistry. FIG. 9 shows the cells on this platform with these three different media conditions. Only the cells in DM/EM condition showed both EdU+ proliferative cells and MUC2+ goblet cells. The EdU+ proliferative cells were highly populated over and near the holes creating proliferative zones.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for producing a planar tissue construct comprising a first epithelial cell population and a second epithelial cell population, the first epithelial cell population and the second epithelial cell population each comprising different cell populations, the method comprising:

(a) providing an apparatus, the apparatus comprising:
(i) a basal well comprising a first wall and at least one sidewall extending upwardly from the first wall; and
(ii) a luminal well held within the basal well, the luminal well comprising
(1) a planar second wall comprising a first region traversed by a plurality of microholes and a second region that is not traversed by the plurality of microholes,
(2) a planar porous layer for culture of epithelial cells overlaying the first region and the second region of the planar second wall, to form a first planar porous region and a second planar porous region, respectively, and
(3) at least one sidewall extending upwardly from the planar second wall, wherein the planar second wall comprises reduced porosity as compared to the planar porous layer;
(b) providing a basal culture media in the basal well and a luminal culture media in the luminal well, wherein the basal culture media is different from the luminal culture media;
(c) generating a gradient of growth factors from the basal culture media that extends from a center of the plurality of microholes outward in a planar manner;
(d) depositing epithelial cells on the first planar porous region and the second planar porous region;
(e) proliferating, differentiating, or both proliferating and differentiating the epithelial cells on the first planar porous region into the first epithelial cell population in response to the growth factors delivered via the plurality of microholes; and
(f) proliferating, differentiating, or both proliferating and differentiating the epithelial cells on the second planar porous region into the second epithelial cell population in response to the luminal culture media,
wherein the first epithelial cell population is different from the second epithelial cell population, and the first epithelial cell population and the second epithelial cell population proliferate, differentiate, or both proliferate and differentiate as a monolayer on the first planar porous region and the second planar porous region, respectively,
thereby producing the planar tissue construct.

2. The method of claim 1, wherein the first and second epithelial cell populations comprise primary epithelial cells.

3. The method of claim 1, wherein the basal culture media and/or the luminal culture media comprise one or more stimuli, wherein the one or more stimuli are each selected from the group consisting of a drug, a nutraceutical, a signaling molecule, a toxin, an inflammatory mediator, and a microbe-derived compound.

4. The method of claim 3, further comprising detecting or determining an effect of the one or more stimuli, optionally wherein the detecting or determining comprises comparing one or more of cell differentiation and cell proliferation after exposure to the one or more stimuli to one or more of cell differentiation and cell proliferation prior to exposure to the one or more stimuli and/or in a comparable tissue construct not exposed to the one or more stimuli.

5. The method of claim 1, further comprising providing an expansion media in the basal well and in the luminal well before providing the basal culture media in the basal well and the luminal culture media in the luminal well.

6. The method of claim 1, wherein the basal culture media is an expansion media, and the luminal culture media is a differentiation media.

7. The method of claim 1, wherein the basal culture media is a differentiation media, and the luminal culture media is an expansion media.

* * * * *